United States Patent
Dong et al.

(10) Patent No.: US 12,065,667 B2
(45) Date of Patent: Aug. 20, 2024

(54) MODIFIED CPF1 MRNA, MODIFIED GUIDE RNA, AND USES THEREOF

(71) Applicant: OHIO STATE INNOVATION FOUNDATION, Columbus, OH (US)

(72) Inventors: Yizhou Dong, Dublin, OH (US); Bin Li, Columbus, OH (US)

(73) Assignee: OHIO STATE INNOVATION FOUNDATION, Columbus, OH (US)

(*) Notice: Subject to any disclaimer, the term of this patent is extended or adjusted under 35 U.S.C. 154(b) by 1242 days.

(21) Appl. No.: 16/094,062

(22) PCT Filed: Apr. 14, 2017

(86) PCT No.: PCT/US2017/027762
§ 371 (c)(1),
(2) Date: Oct. 16, 2018

(87) PCT Pub. No.: WO2017/181107
PCT Pub. Date: Oct. 19, 2017

(65) Prior Publication Data
US 2020/0172935 A1      Jun. 4, 2020

Related U.S. Application Data

(60) Provisional application No. 62/400,843, filed on Sep. 28, 2016, provisional application No. 62/385,471, filed on Sep. 9, 2016, provisional application No. 62/328,741, filed on Apr. 28, 2016, provisional application No. 62/323,683, filed on Apr. 16, 2016.

(51) Int. Cl.
*C12N 15/67* (2006.01)
*C12N 9/22* (2006.01)
*C12N 15/10* (2006.01)
*C12N 15/85* (2006.01)
*C12N 15/90* (2006.01)

(52) U.S. Cl.
CPC ............. *C12N 15/907* (2013.01); *C12N 9/22* (2013.01); *C12N 15/102* (2013.01); *C12N 15/67* (2013.01); *C12N 15/85* (2013.01); *C12N 2310/315* (2013.01); *C12N 2310/321* (2013.01); *C12N 2310/322* (2013.01); *C12N 2310/335* (2013.01)

(58) Field of Classification Search
CPC ........ C12N 2310/315; C12N 2310/322; C12N 2310/335; C12N 15/85; C12N 9/22; C12N 15/907; C12N 2310/20
See application file for complete search history.

(56) References Cited

U.S. PATENT DOCUMENTS

2015/0275193 A1   10/2015   Angel et al.
2016/0068864 A1   3/2016   Charpentier et al.

OTHER PUBLICATIONS

Safari et al. (Cell Biosci, 2019 vol. 9:1-21).*

(Continued)

*Primary Examiner* — Terra C Gibbs
(74) *Attorney, Agent, or Firm* — Meunier Carlin & Curfman LLC

(57) ABSTRACT

The present disclosure generally relates to systems, methods and compositions for use in Clustered Regularly Interspaced Short Palindromic Repeats (CRISPR)-Cpf1 genome editing systems. Disclosed herein are modified Cpf1 mRNAs, modified guide RNAs, and combinations thereof, that confer increased levels of genome editing.

6 Claims, 51 Drawing Sheets

Specification includes a Sequence Listing.

(56) References Cited

OTHER PUBLICATIONS

Li et al. (Nat Biomed Eng. May 2017; 1(5): 0066, plus Supplementary Information).*
Li et al. (Nature Protocols, 2018 vol. 13:899-914, plus Supplementary Information).*
Basila et al. (PLoS ONE 12(11): e0188593, pp. 1-19).*
International Search Report and Written Opinion of the U.S. International Searching Authority. Application No. PCT/US2017/027762. Mailed Sep. 29, 2017. 16 pages.
Zetsche, Bernd, et al. "Cpf1 is a single RNA-guided endonuclease of a class 2 CRISPR-Cas system." Cell 163.3 (2015): 759-771.
Altschul et al. (1977) Gapped BLAST and PSI-BLAST: a new generation of protein database search programs. Nuc. Acids Res. 25:3389-3402.
Altschul et al. (1990) Basic local alignment search tool. J. Mol. Biol. 215:403-410.
Anderson, B. R., Muramatsu, H., Nallagatla, S. R., Bevilacqua, P. C., Sansing, L. H., Weissman, D., and Kariko, K. (2010) Incorporation of pseudouridine into mRNA enhances translation by diminishing PKR activation. Nucleic Acids Res. 38, 5884-5892.
Andries, O. et al. N(1)-methylpseudouridine-incorporated mRNA outperforms pseudouridine-incorporated mRNA by providing enhanced protein expression and reduced immunogenicity in mammalian cell lines and mice. J Control Release 217, 337-344 (2015).
Anguille, S., Smits, E. L., Lion, E., van Tendeloo, V. F., and Berneman, Z. N. (2014) Clinical use of dendritic cells for cancer therapy. Lancet Oncol. 15, e257-267.
Beaucage and Carruthers, Deoxynucleoside phosphoramidites-a new class of key intermediates for deoxypolynucleotide synthesis. Tetrahedron Lett., 22:1859-1862 (1981).
Bosley, K.S. et al. CRISPR germline engineering—the community speaks. Nat Biotechnol 33, 478-486 (2015).
Chen, B. et al. Dynamic imaging 5 of genomic loci in living human cells by an optimized CRISPR/Cas system. Cell 155, 1479-1491 (2013).
Cong, L. et al. Multiplex genome engineering using CRISPR/Cas systems. Science 339, 819-823 (2013).
Dang, Y. et al. Optimizing sgRNA structure to improve CRISPR-Cas9 knockout efficiency. Genome Biol 16, 280 (2015).
Dong, D. et al. The crystal structure of Cpf1 in complex with CRISPR RNA. Nature 532, 522-526 (2016).
Fonfara, I., Richter, H., Bratovic, M., Le Rhun, A. & Charpentier, E. The CRISPR associated DNA-cleaving enzyme Cpf1 also processes precursor CRISPR RNA. Nature 532, 517-521 (2016).
Hendel, A. et al. Chemically modified guide RNAs enhance CRISPR-Cas genome editing in human primary cells. Nat Biotechnol 33, 985-989 (2015).
Henikoff and Henikoff (1989) Amino acid substitution matrices from protein blocks. Proc. Natl. Acad. Sci. USA 89:10915.
Islam, M. A., Reesor, E. K., Xu, Y., Zope, H. R., Zetter, B. R., and Shi, J. (2015) Biomaterials for mRNA delivery. Biomater. Sci. 3, 1519-1533.
Jinek, M et al. A programmable dual-RNA-guided DNA endonuclease in adaptive bacterial immunity. Science 337, 816-821 (2012).
Kariko, K., Muramatsu, H., Keller, J. M., and Weissman, D. (2012) Increased erythropoiesis in mice injected with submicrogram quantities of pseudouridine-containing mRNA encoding erythropoietin. Mol. Ther. 20, 948-953.
Kariko, K., Muramatsu, H., Welsh, F. A., Ludwig, J., Kato, H., Akira, S., and Weissman, D. (2008) Incorporation of pseudouridine into mRNA yields superior nonimmunogenic vector with increased translational capacity and biological stability. Mol. Ther. 16, 1833-1840.
Kariko, K., Ni, H. P., Capodici, J., Lamphier, M., and Weissman, D. (2004) mRNA is an endogenous ligand for Toll-like receptor 3. J. Biol. Chem. 279, 12542-12550.
Karlin and Altschul (1993) Applications and statistics for multiple high-scoring segments in molecular sequences. Proc. Natl. Acad. Sci. USA 90:5873-5787.

Kauffman, K. J., Dorkin, J. R., Yang, J. H., Heartlein, M. W., DeRosa, F., Mir, F. F., Fenton, O. S., and Anderson, D. G. (2015) Optimization of lipid nanoparticle formulations for mRNA delivery in vivo with fractional factorial and definitive screening designs. Nano Lett. 15, 7300-7306.
Kim, D. et al. Genome-wide analysis reveals specificities of Cpf1 endonucleases in human cells. Nat Biotechnol 34, 863-868 (2016).
Kleinstiver, B.P. et al. Genome-wide specificities of CRISPR-Cas Cpf1 nucleases in human cells. Nat Biotechnol 34, 869-874 (2016).
Kleinstiver, B.P. et al. High-fidelity CRISPR-Cas9 nucleases with No. detectable genomewide off-target effects. Nature 529, 490-495 (2016).
Kormann, M. S., Hasenpusch, G., Aneja, M. K., Nica, G., Flemmer, A. W., Herber-Jonat, S., Huppmann, M., Mays, L. E., Illenyi, M., Schams, A., et al. (2011) Expression of therapeutic proteins after delivery of chemically modified mRNA in mice. Nat. Biotechnol. 29, 154-157.
Li, B., Luo, X. & Dong, Y. Effects of Chemically Modified Messenger RNA on Protein Expression. Bioconjug Chem 27, 849-853, (2016).
Li, B., Luo, X., Deng, B., Wang, J., McComb, D. W., Shi, Y., Gaensler, K. M., Tan ,X., Dunn, A. L., Kerlin, B. A., et al. (2015) An orthogonal array optimization of lipid-like nanoparticles for mRNA delivery in vivo. Nano Lett. 15, 8099-8107.
Makarova, K.S. et al. Evolution and classification of the CRISPR-Cas systems. Nat Rev Microbiol 9, 467-477 (2011).
Mali, P. et al. RNA-guided human genome engineering via Cas9. Science 339, 823-826 (2013).
Matteucci, et al., Synthesis of deoxyoligonucleotides on a polymer support. J. Am. Chem. Soc., 103:3185, 1981.
McIvor, R. S. (2011) Therapeutic delivery of mRNA: the medium is the message. Mol. Ther. 19, 822-823.
O'Hare, et al., Transformation of mouse fibroblasts to methotrexate resistance by a recombinant plasmid expressing a prokaryotic dihydrofolate reductase. Proc. Natl. Acad. Sci. USA., vol. 78(3), p. 1527-31, 1981.
Pascolo, S. (2008) Vaccination with messenger RNA (mRNA). Handb. Exp. Pharmacol. 221-235.
Pinello, L. et al. Analyzing CRISPR genome-editing experiments with CRISPResso. Nat Biotechnol 34, 695-697 (2016).
Rahdar, M. et al. Synthetic CRISPR RNA-Cas9-guided genome editing in human cells. Proc Natl Acad Sci U S A 112, E7110-7117 (2015).
Sahin, U., Kariko, K., and Tureci, O. (2014) mRNA-based therapeutics—developing a new class of drugs. Nat. Rev. Drug Discov. 13, 759-780.
Slaymaker, I.M et al. Rationally engineered Cas9 nucleases with improved specificity, Science 351, 84-88 (2016).
Takebe et al., SR alpha promoter: an efficient and versatile mammalian cDNA expression system composed of the simian virus 40 early promoter and the R-U5 segment of human T-cell leukemia virus type 1 long terminal repeat.. Mol. Cell. Biol., vol. 8(1), p. 466-472, 1988.
Tavernier, G., Andries, O., Demeester, J., Sanders, N. N., De Smedt, S. C., and Rejman, J. (2011) mRNA as gene therapeutic: how to control protein expression. J. Control Release 150, 238-247.
Thess, A., Grund, S., Mui, B. L., Hope, M. J., Baumhof, P., Fotin-Mleczek, M., and Schlake, T. (2015) Sequence-engineered mRNA without chemical nucleoside modifications enables an effective protein therapy in large animals. Mol. Ther. 23, 1456-1464.
Uchida, S., Kataoka, K., and Itaka, K. (2015) Screening of mRNA chemical modification to maximize protein expression with reduced immunogenicity. Pharmaceutics 7, 137-151.
Wang, J., Exline, C. M., DeClercq, J. J., Llewellyn, G. N., Hayward, S. B., Li, P. W., Shivak, D. A., Surosky, R. T., Gregory, P. D., Holmes, M. C., et al. (2015) Homology-driven genome editing in hematopoietic stem and progenitor cells using ZFN mRNA and AAV6 donors. Nat. Biotechnol. 33, 1256-1263.
Watts, J.K., Deleavey, G.F. & Damha, M.J. Chemically modified siRNA: tools and applications. Drug Discov Today 13, 842-855 (2008).
Weissman, D., and Kariko, K. (2015) mRNA: fulfilling the promise of gene therapy. Mol. Ther. 23, 1416-1417.

(56) References Cited

OTHER PUBLICATIONS

Yamano, T. et al. Crystal Structure of Cpf1 in Complex with Guide RNA and Target DNA. Cell 165, 949-962 (2016).

Zangi, L., Lui, K. O., von Gise, A., Ma, Q., Ebina, W., Ptaszek, L. M., Spater, D., Xu, H., Tabebordbar, M., Gorbatov, R., et al. (2013) Modified mRNA directs the fate of heart progenitor cells and induces vascular regeneration after myocardial infarction. Nat. Biotechnol. 31, 898-907.

Zhao, Y., Moon, E., Carpenito, C., Paulos, C. M., Liu, X., Brennan, A. L., Chew, A., Carroll, R. G., Scholler, J., Levine, B. L., et al. (2010) Multiple injections of electroporated autologous T cells expressing a chimeric antigen receptor mediate regression of human disseminated tumor. Cancer Res. 70, 9053-9061.

International Preliminary Report on Patentability issued for Application No. PCT/US2017/027762, dated Oct. 25, 2018, 11 pages.

\* cited by examiner

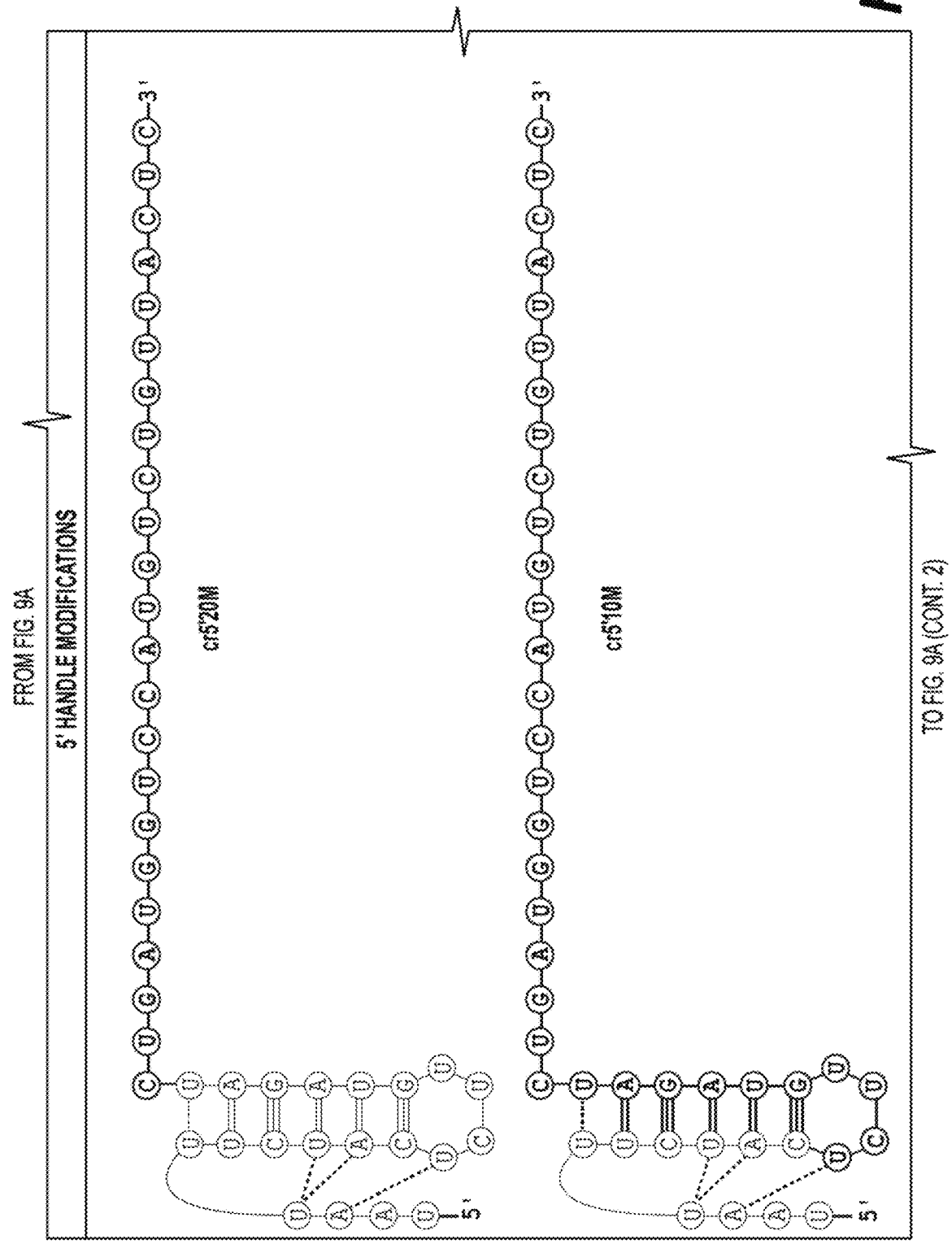

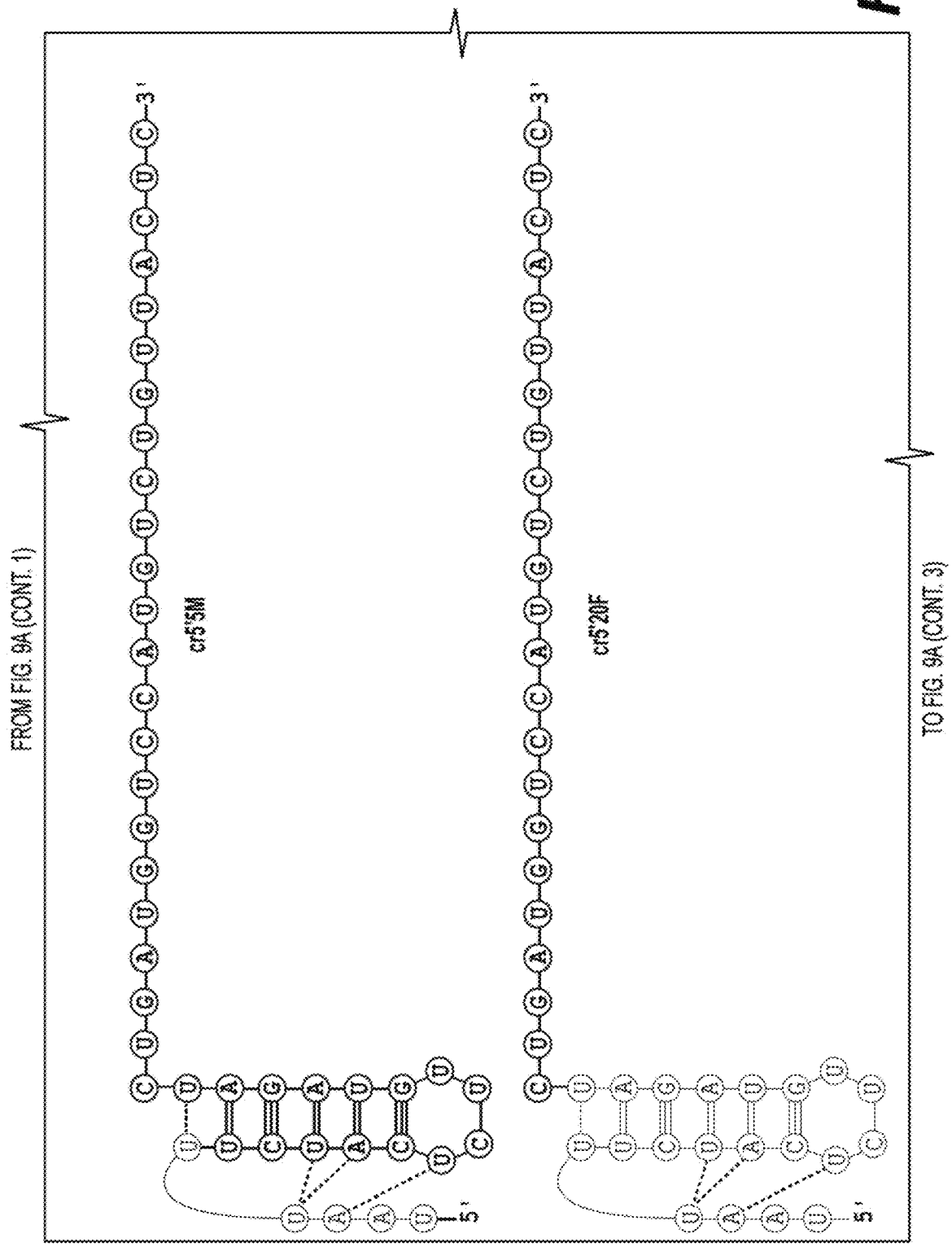
FIG. 9A (CONT. 2)

FIG. 9A (CONT. 3)

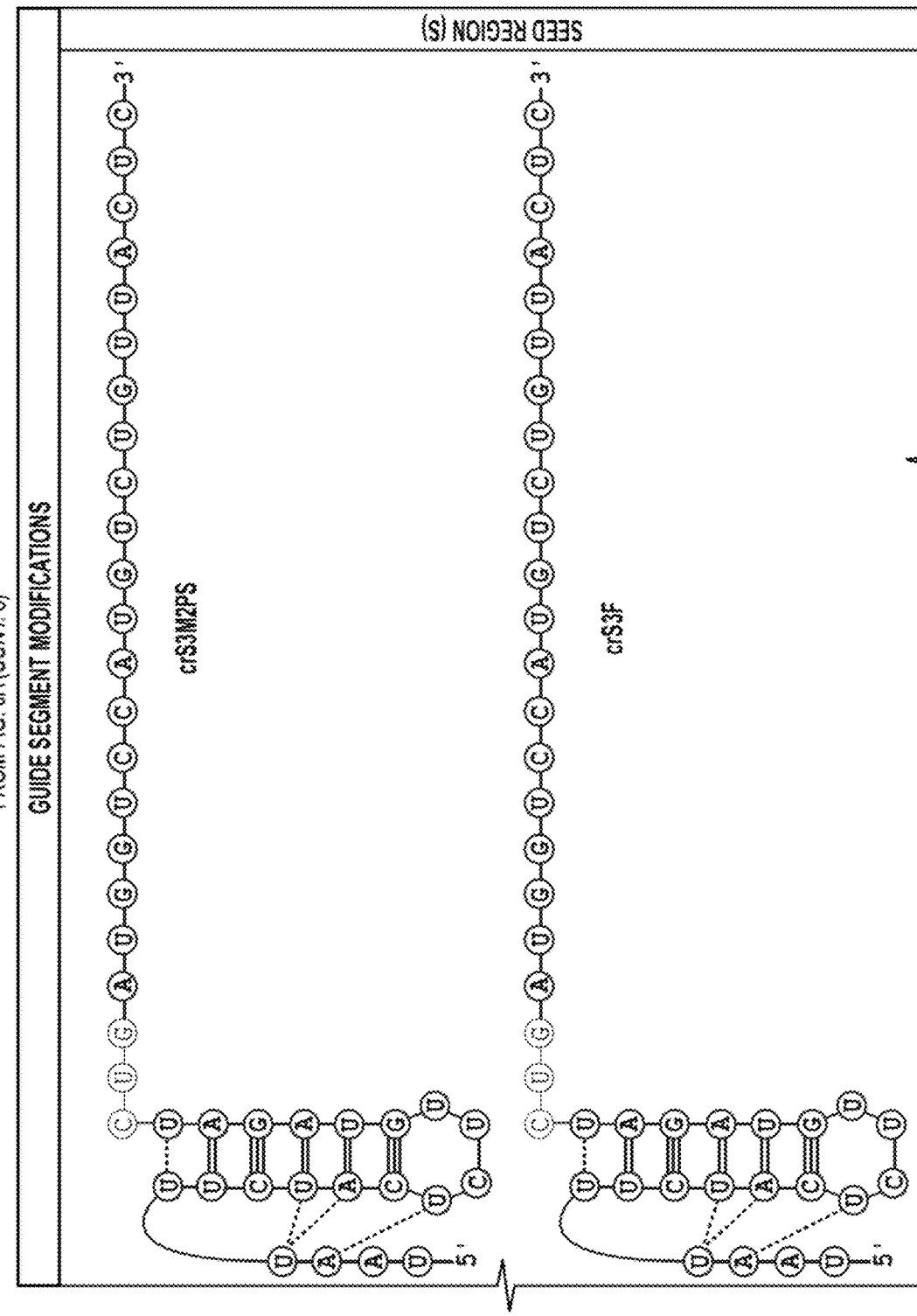

FIG. 9A (CONT. 5)

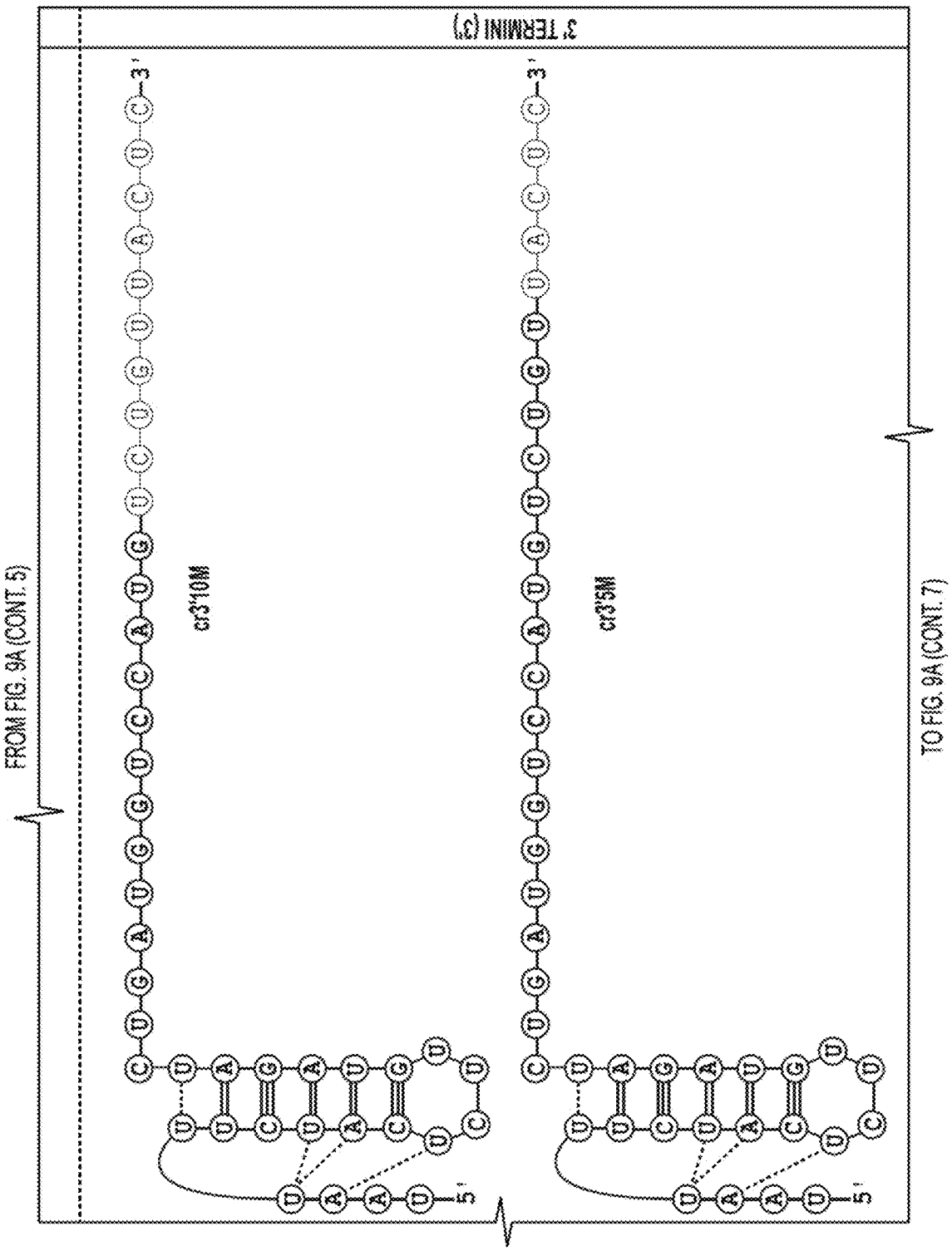
FIG. 9A (CONT. 6)

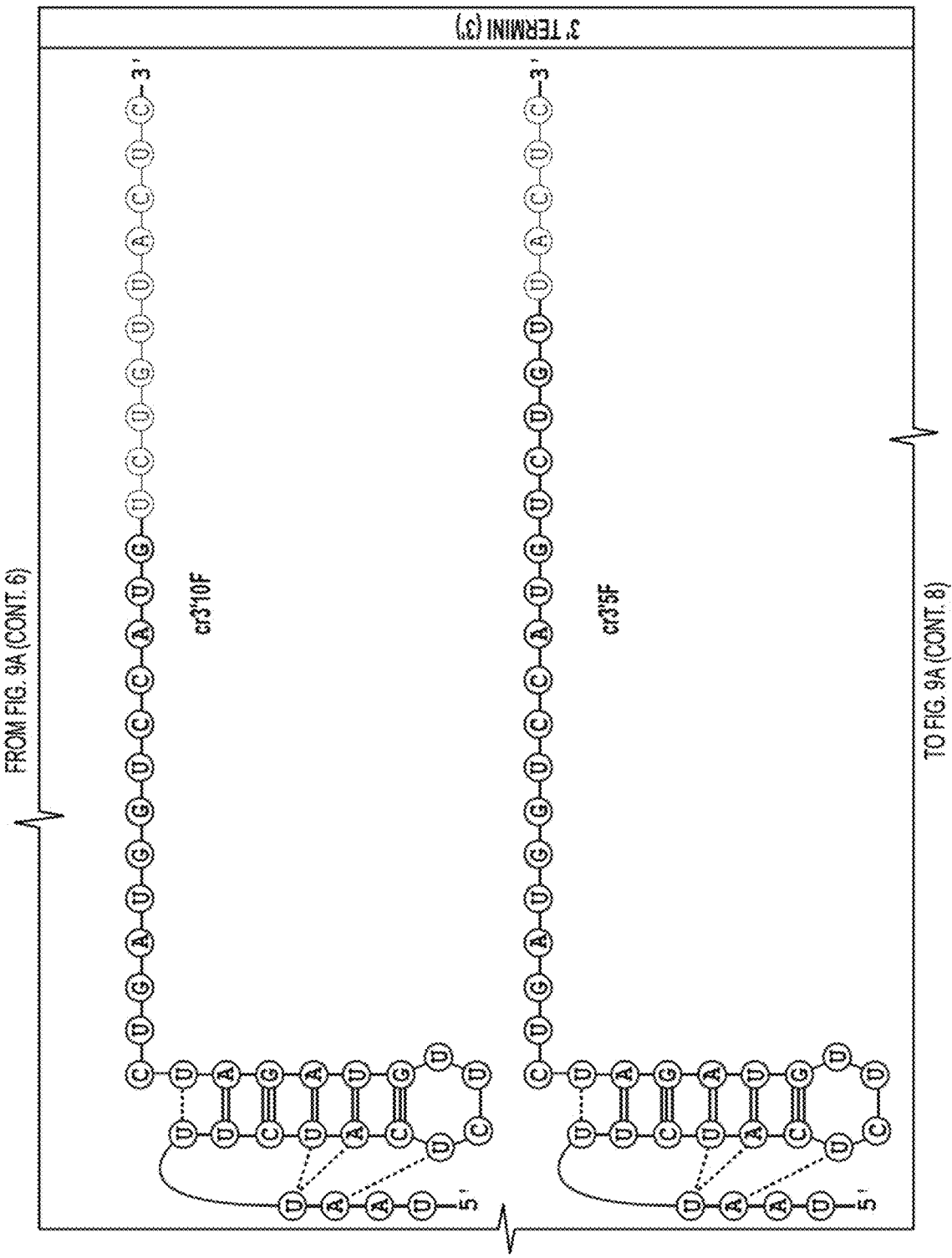
FIG. 9A (CONT. 7)

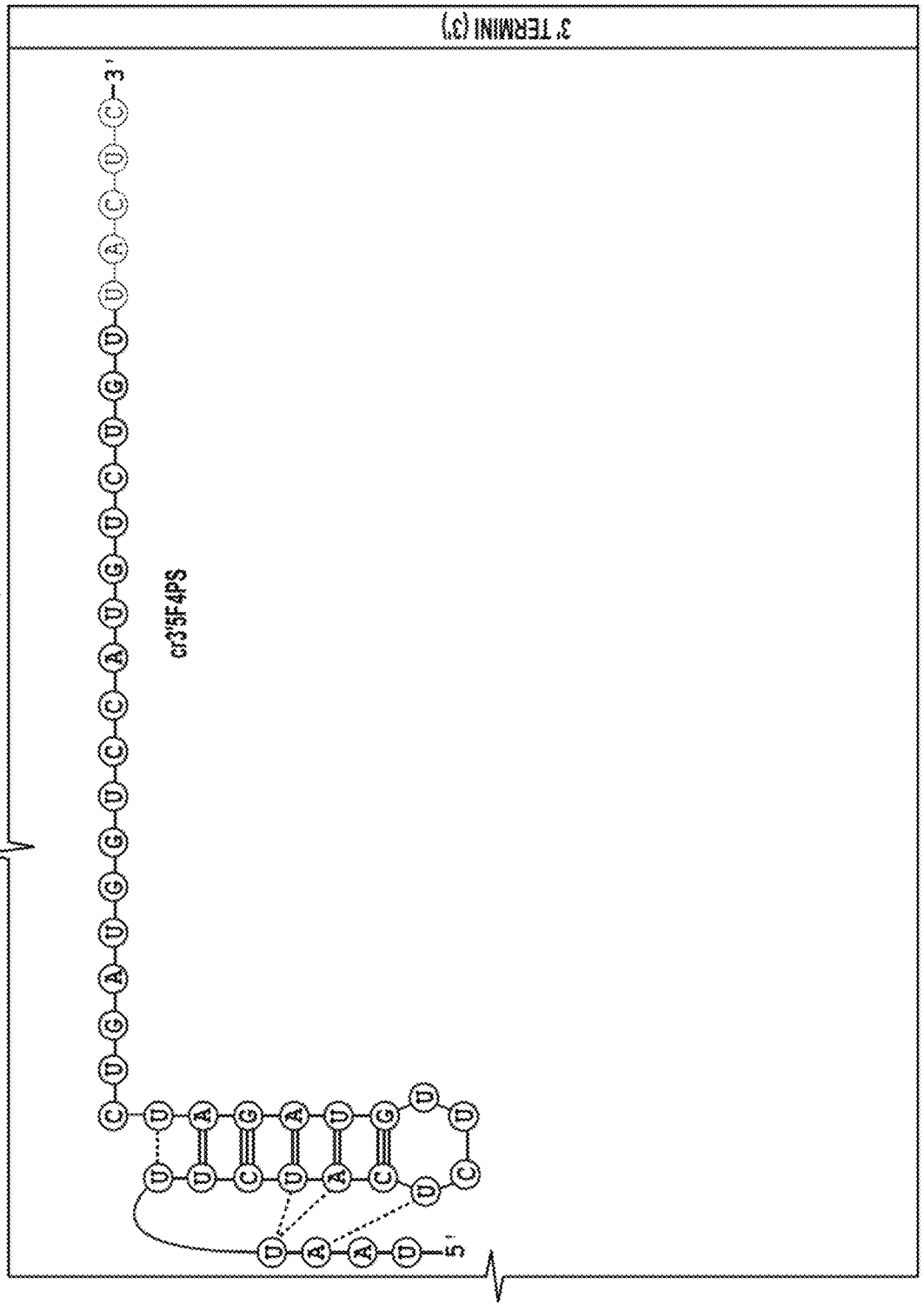
FIG. 9A (CONT. 8)

c

*FANCF-2* Locus: >NC_000011.10, GRCh38.p7 d

*DNMT1-3* Locus: >NC_000019.10, GRCh38.p7

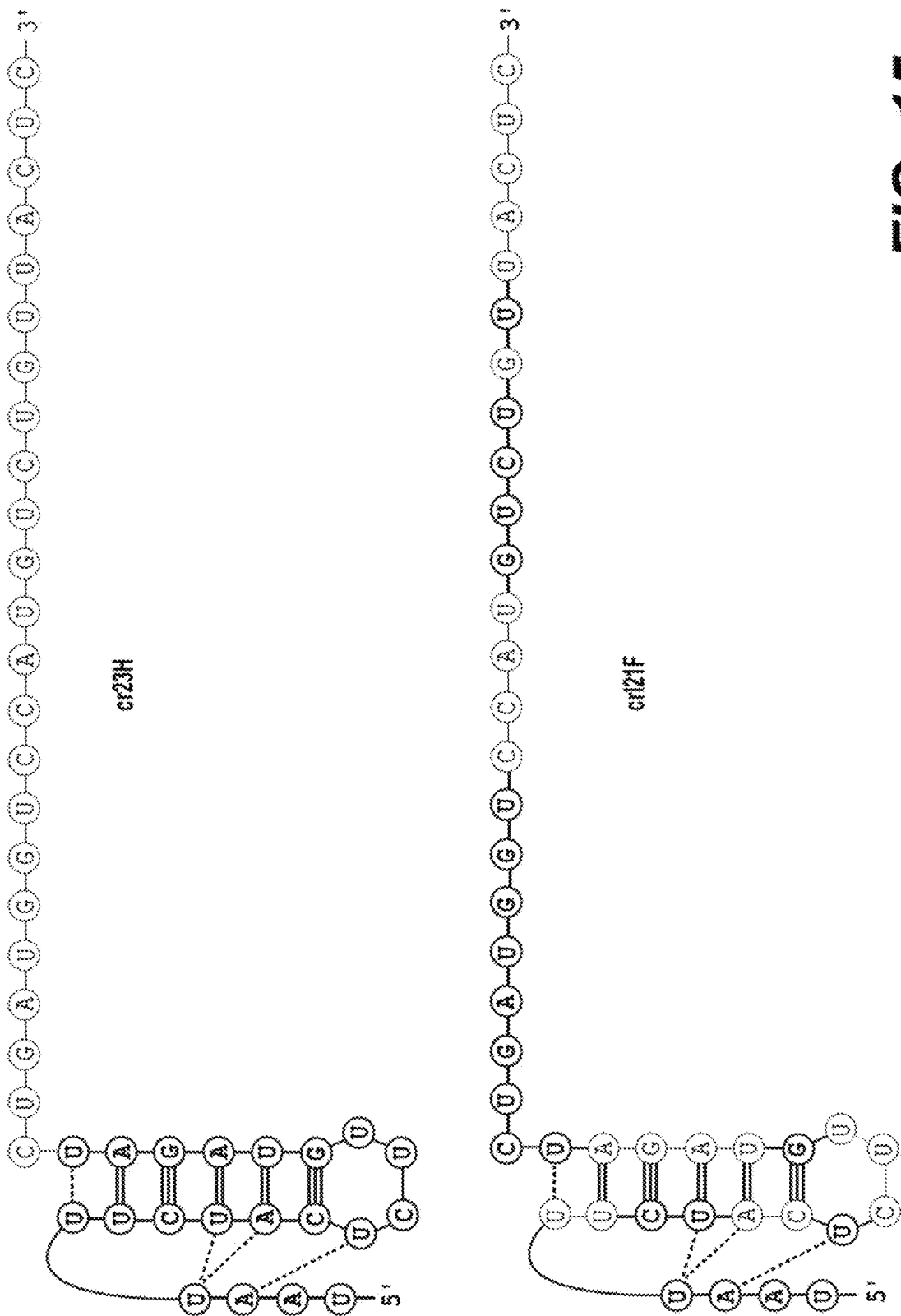
FIG. 15 (CONT. 1)

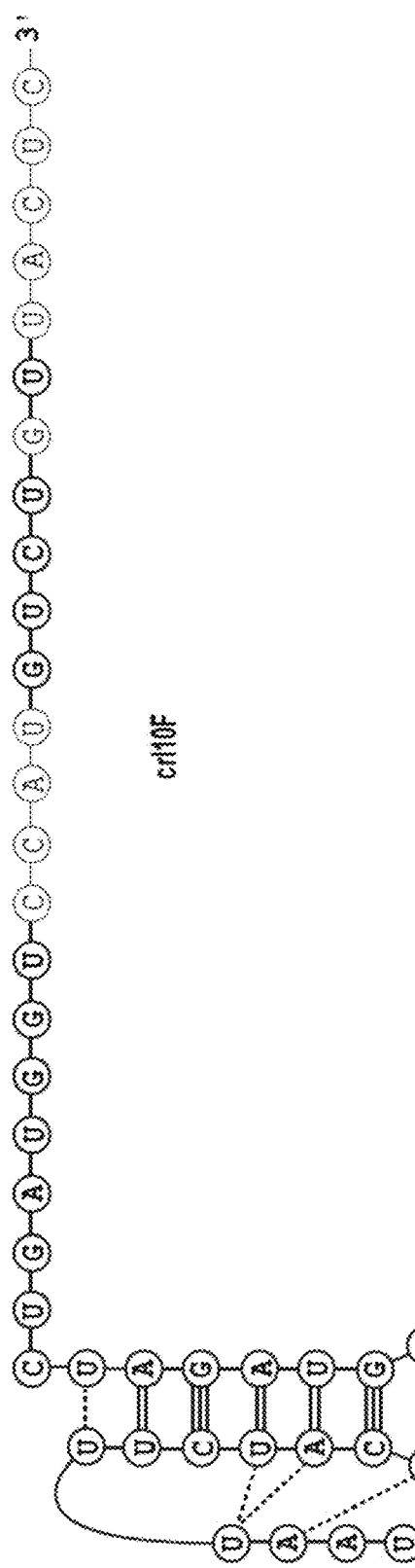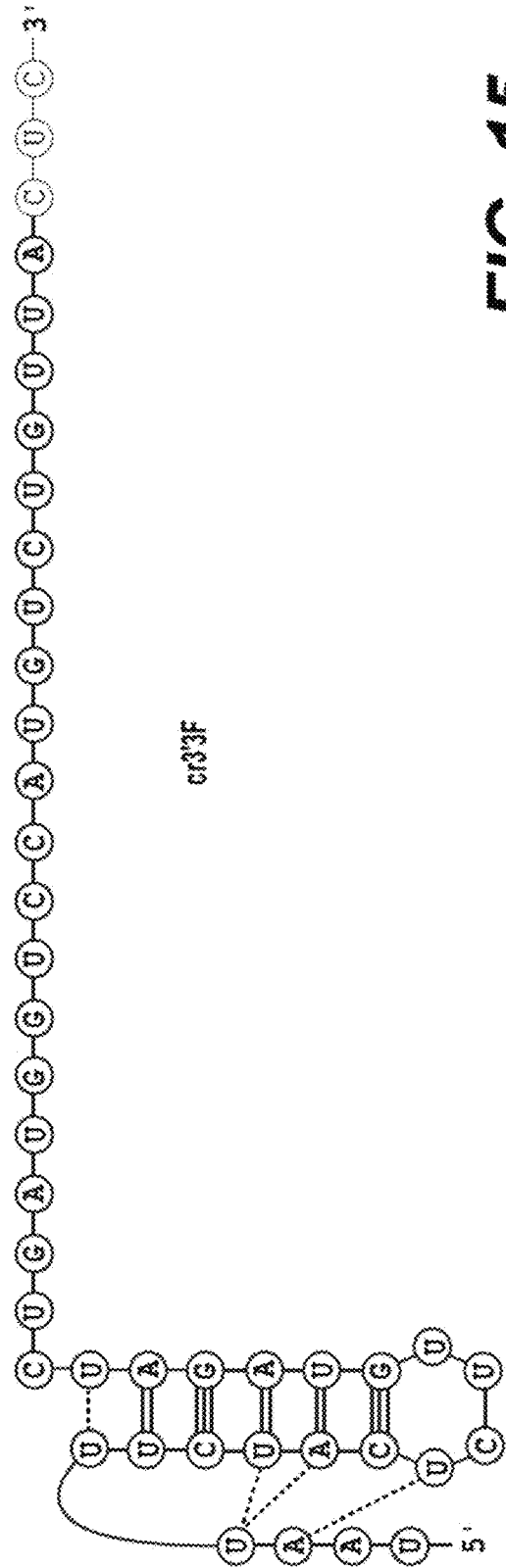
FIG. 15 (CONT. 2)

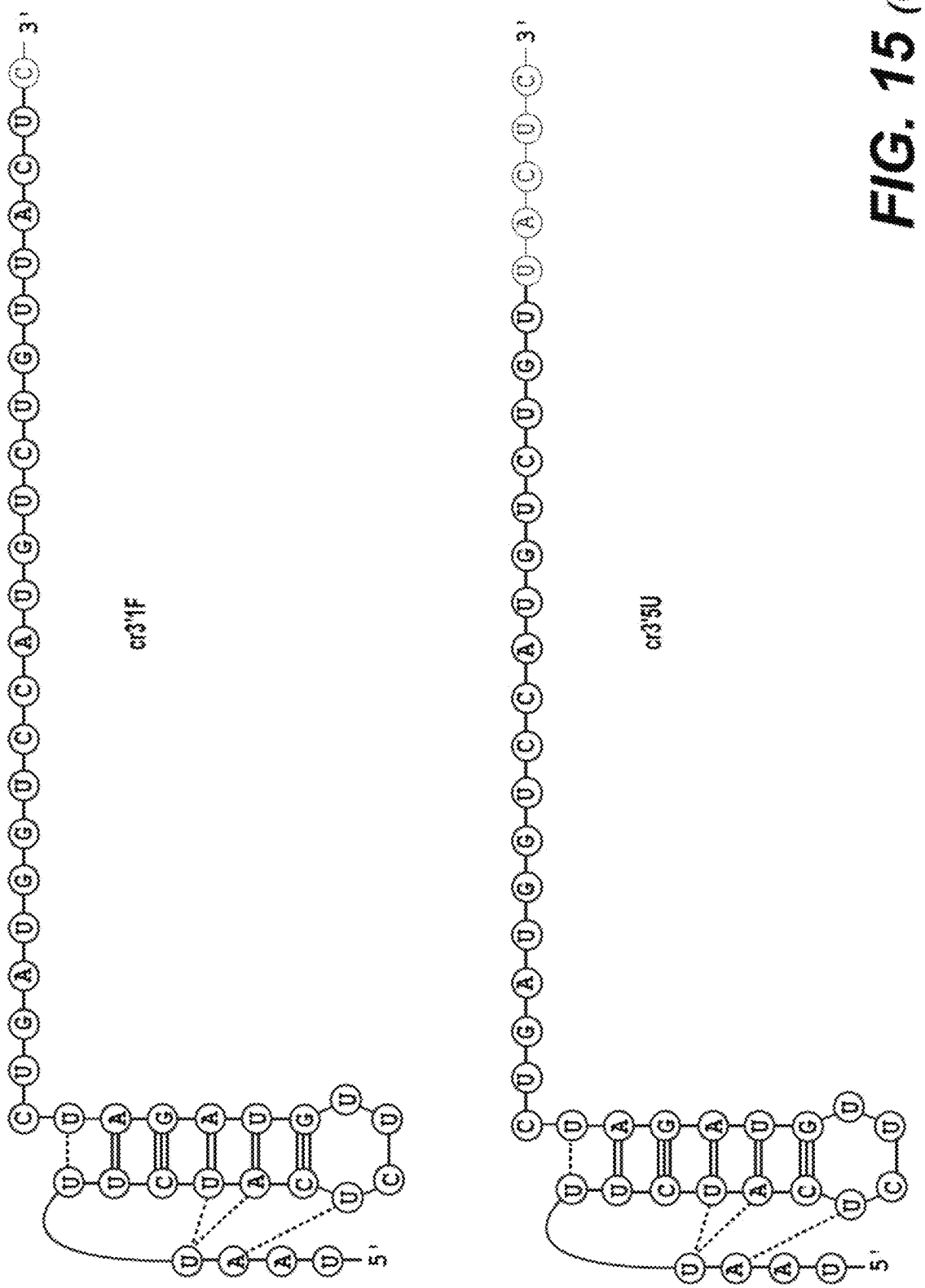
FIG. 15 (CONT. 3)

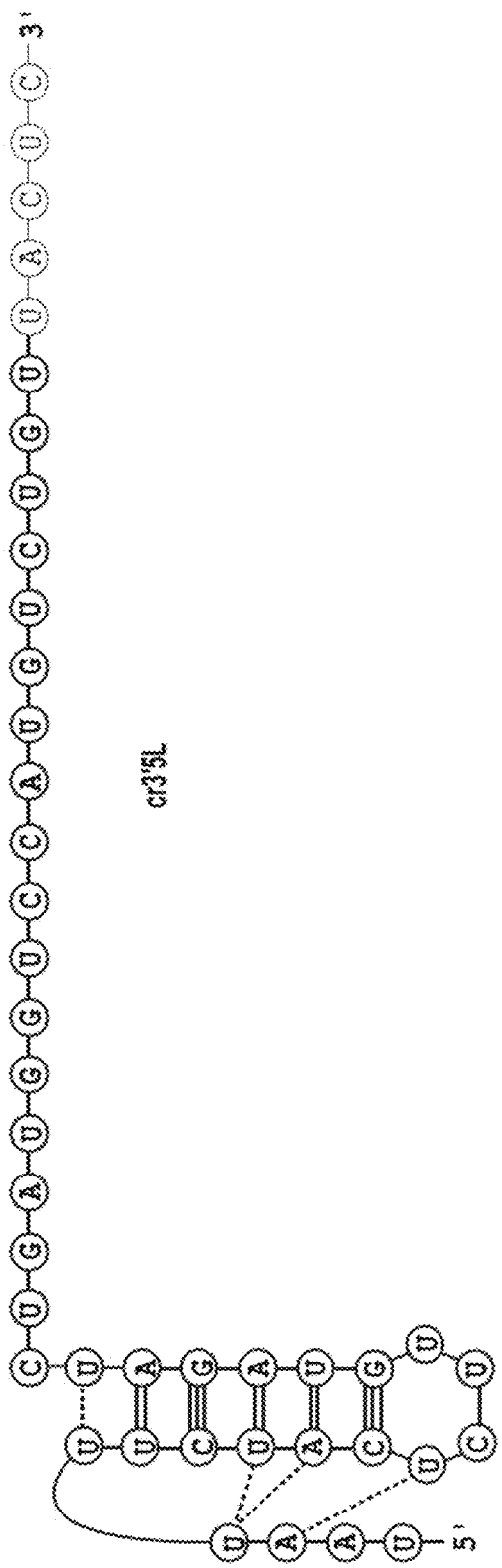
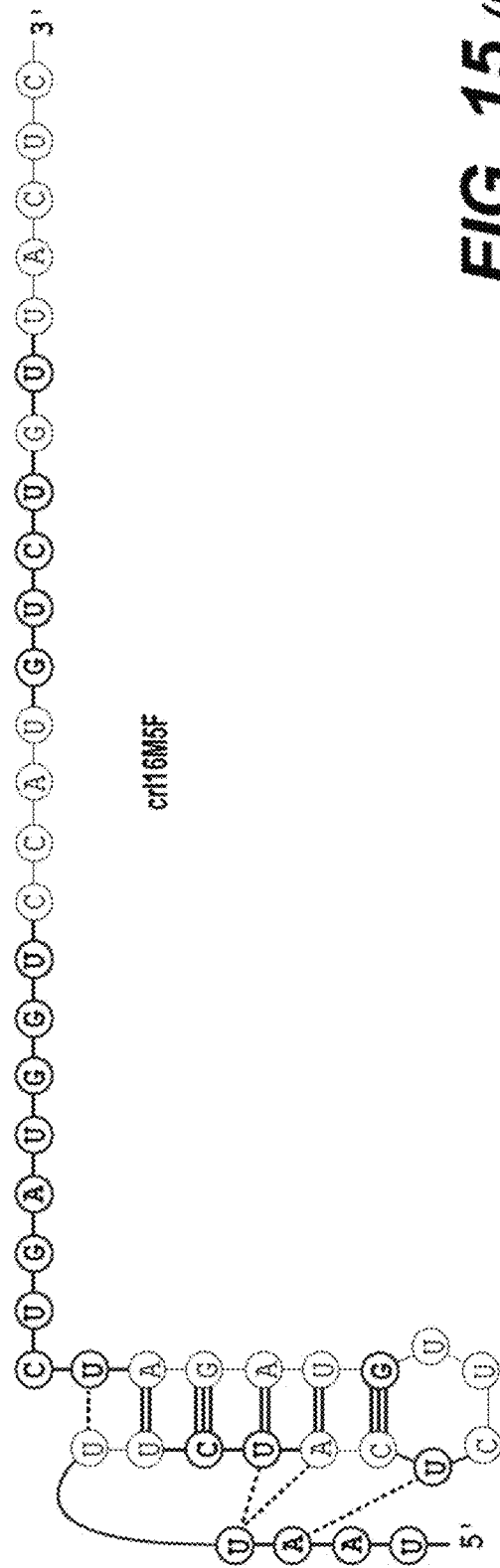
FIG. 15 (CONT. 4)

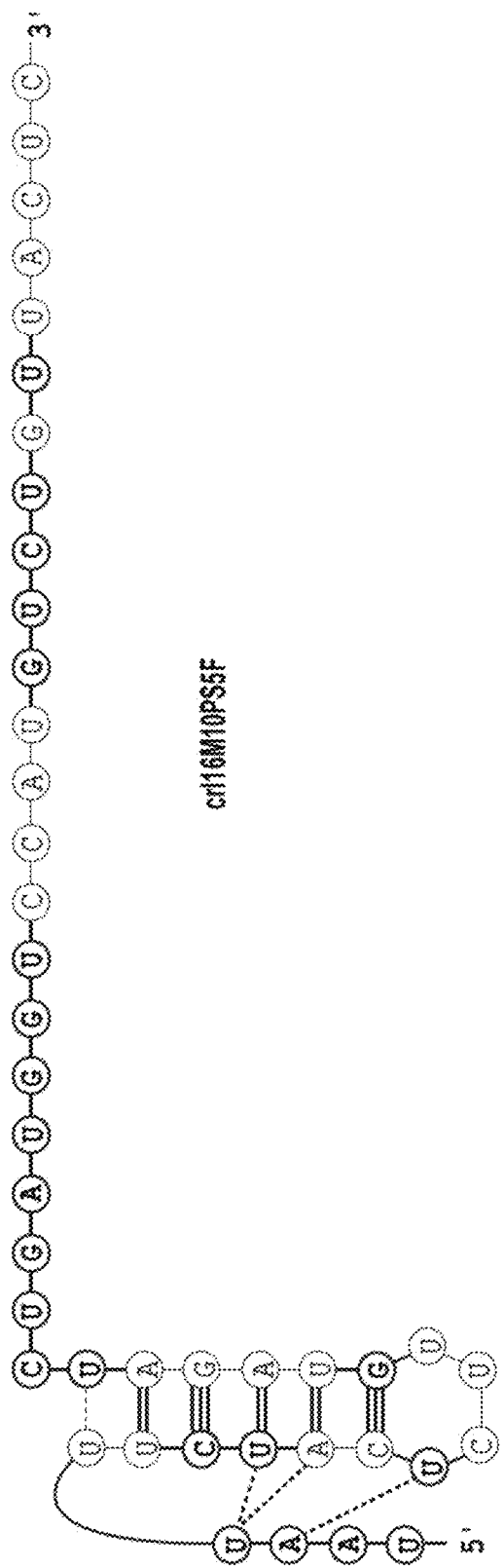
FIG. 15 (CONT. 5)

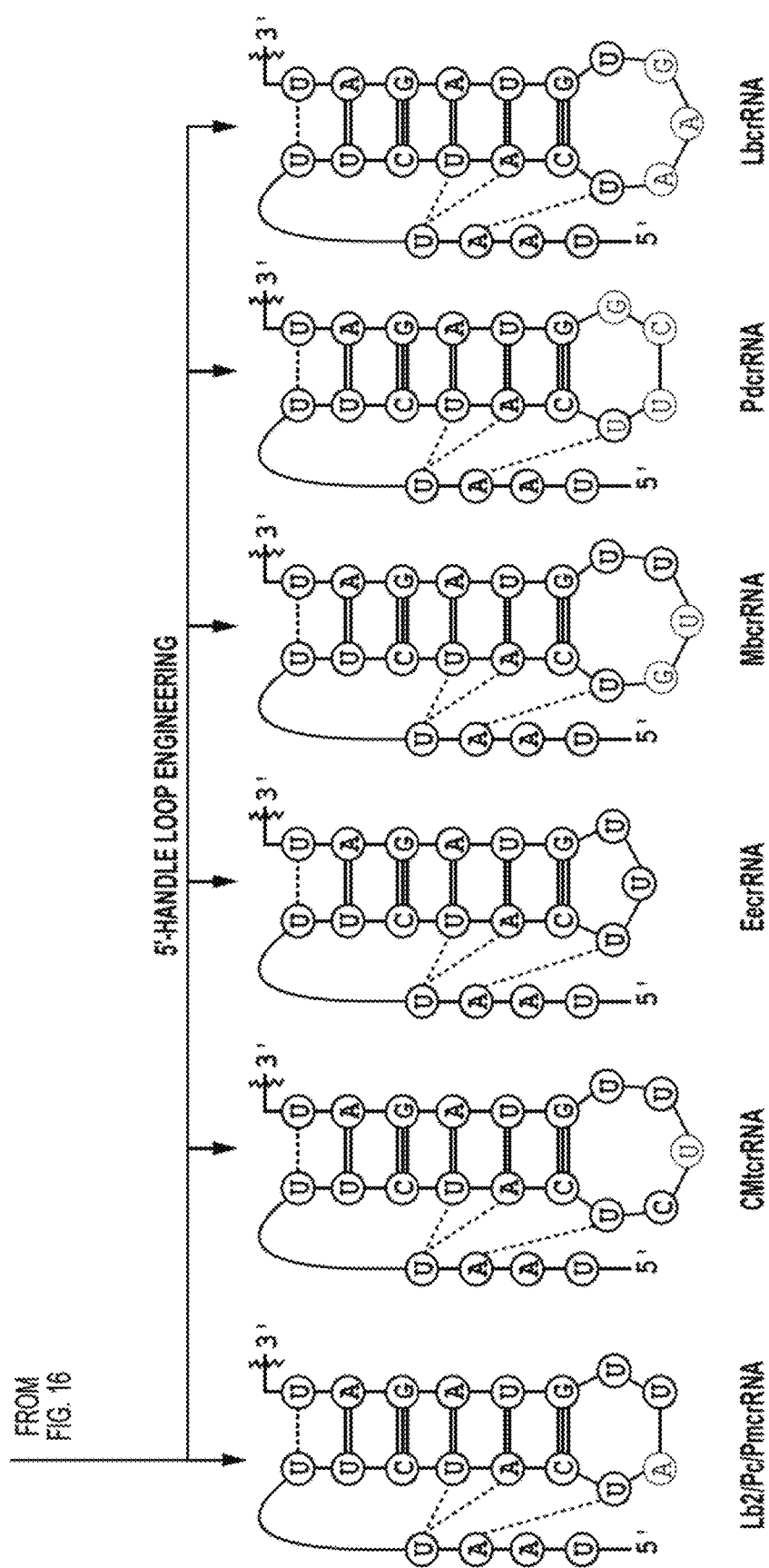
FIG. 16 (CONT. 1)

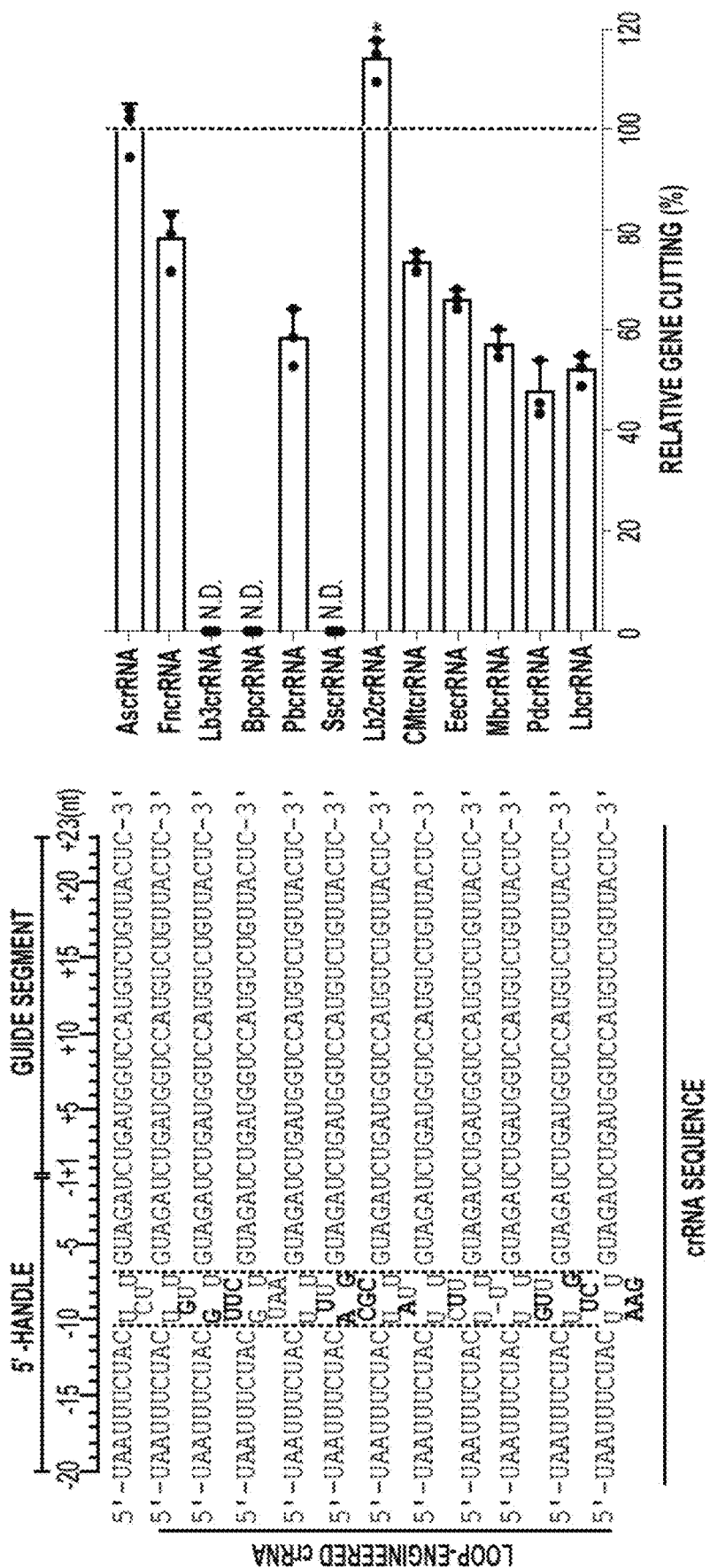
FIG. 16 (CONT. 2)

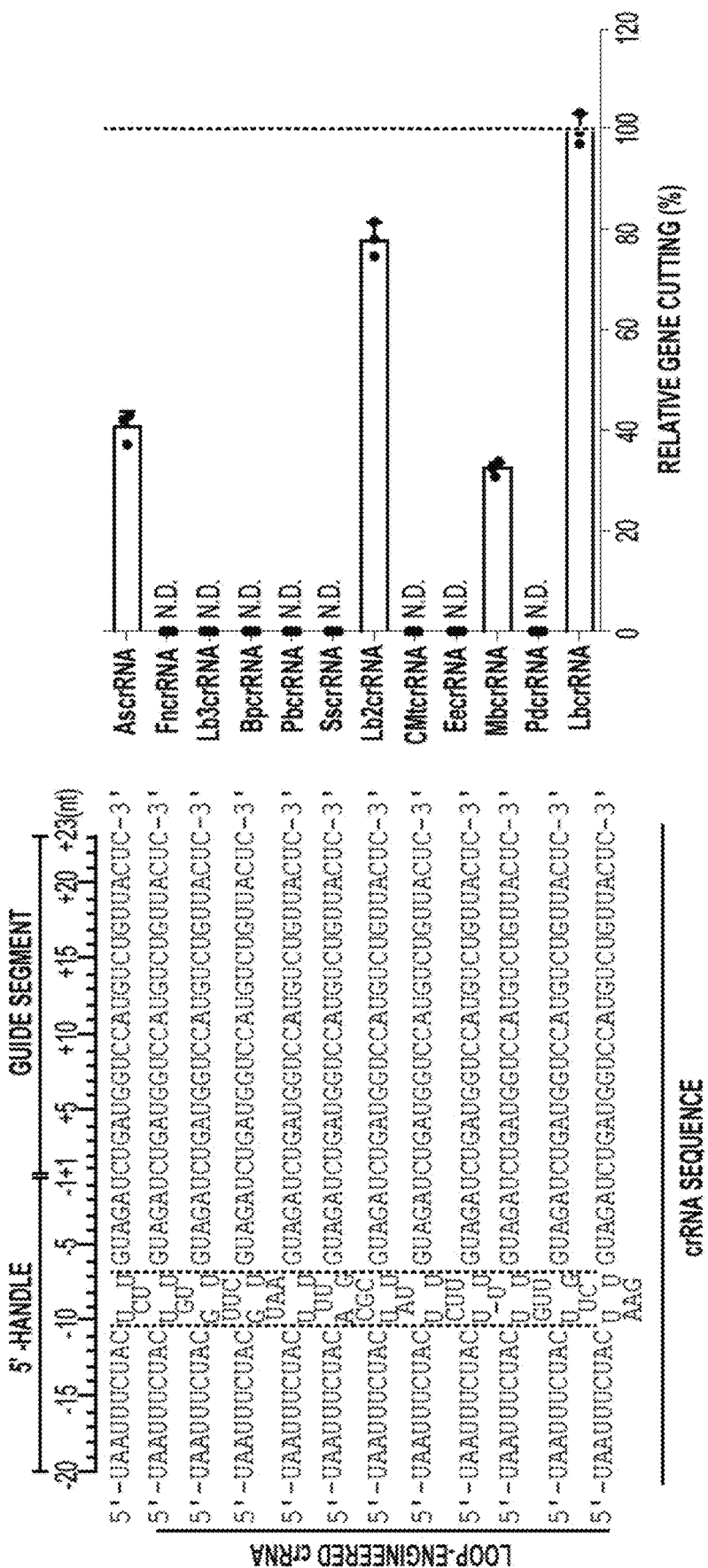
FIG. 16 (CONT. 3)

| No. | AscrRNA | Modification pattern (5'- to -3') | M.W. | |
|---|---|---|---|---|
| | | | Calcd. | Found |
| Chemically modified crRNAs targeting *DNMT1-3* locus | | | | |
| WT | crWT | UAAUUCUACUCUUGUAGAUCUGAUGGUCCAUGUCUGUUACUC (SEQ ID NO:3) | 13552.5 | 13552.2 |
| 1 | cr42PS | UAAUUCUACUCUUGUAGAUCUGAUGGUCCAUGUCUGUUACUC (SEQ ID NO:11) | 14227.0 | 14226.1 |
| 2 | cr5'&'3F2PS | UAAUUCUACUCUUGUAGAUCUGAUGGUCCAUGUCUGUUACUC (SEQ ID NO:12) | 13628.7 | 13627.6 |
| 3 | cr5'20M | UAAUUCUACUCUUGUAGAUCUGAUGGUCCAUGUCUGUUACUC (SEQ ID NO:13) | 13832.5 | 13832.1 |
| 4 | cr5'10M | UAAUUCUACUCUUGUAGAUCUGAUGGUCCAUGUCUGUUACUC (SEQ ID NO:14) | 13692.5 | 13691.8 |
| 5 | cr5'5M | UAAUUCUACUCUUGUAGAUCUGAUGGUCCAUGUCUGUUACUC (SEQ ID NO:15) | 13622.5 | 13621.5 |
| 6 | cr5'20F | UAAUUCUACUCUUGUAGAUCUGAUGGUCCAUGUCUGUUACUC (SEQ ID NO:16) | 13592.5 | 13590.6 |
| 7 | cr5'10F | UAAUUCUACUCUUGUAGAUCUGAUGGUCCAUGUCUGUUACUC (SEQ ID NO:17) | 13572.5 | 13570.7 |
| 8 | cr5'5F | UAAUUCUACUCUUGUAGAUCUGAUGGUCCAUGUCUGUUACUC (SEQ ID NO:18) | 13562.5 | 13560.9 |
| 9 | crS3M3PS | UAAUUCUACUCUUGUAGAUCUGAUGGUCCAUGUCUGUUACUC (SEQ ID NO:19) | 13642.7 | 13643.4 |
| 10 | crS3F | UAAUUCUACUCUUGUAGAUCUGAUGGUCCAUGUCUGUUACUC (SEQ ID NO:20) | 13558.5 | 13557.9 |
| 11 | crS2F | UAAUUCUACUCUUGUAGAUCUGAUGGUCCAUGUCUGUUACUC (SEQ ID NO:21) | 13556.5 | 13557.4 |
| 12 | crS1F | UAAUUCUACUCUUGUAGAUCUGAUGGUCCAUGUCUGUUACUC (SEQ ID NO:22) | 13554.5 | 13553.6 |
| 13 | cr3'10M | UAAUUCUACUCUUGUAGAUCUGAUGGUCCAUGUCUGUUACUC (SEQ ID NO:23) | 13692.5 | 13691.2 |
| 14 | cr3'5M | UAAUUCUACUCUUGUAGAUCUGAUGGUCCAUGUCUGUUACUC (SEQ ID NO:24) | 13622.5 | 13621.2 |
| 15 | cr3'10F | UAAUUCUACUCUUGUAGAUCUGAUGGUCCAUGUCUGUUACUC (SEQ ID NO:25) | 13572.5 | 13572.0 |
| 16 | cr3'5F | UAAUUCUACUCUUGUAGAUCUGAUGGUCCAUGUCUGUUACUC (SEQ ID NO:26) | 13562.5 | 13561.4 |
| 17 | cr3'5F4PS | UAAUUCUACUCUUGUAGAUCUGAUGGUCCAUGUCUGUUACUC (SEQ ID NO:27) | 13626.7 | 13625.8 |
| 18 | cr3'5U | UAAUUCUACUCUUGUAGAUCUGAUGGUCCAUGUCUGUUACUC (SEQ ID NO:28) | 13626.7 | 13625.8 |
| 19 | cr3'5L | UAAUUCUACUCUUGUAGAUCUGAUGGUCCAUGUCUGUUACUC (SEQ ID NO:29) | 13626.7 | 13625.8 |

*FIG. 19*

| | | | | |
|---|---|---|---|---|
| 20 | crI21F | UAAU*UUCUACUCUUGUAGA*UCUGAUGG UCCAUGUCUGUUACUC (SEQ ID NO:30) | 13594.5 | 13594.2 |
| 21 | crI16M5F | UAAU*UU*CU*A*CU*C*UU*G*UAGAUCUGAUGG UCCAUGUCUGU*UACUC* (SEQ ID NO:31) | 13786.5 | 13783.7 |
| 22 | crI16M10PS5F | UAAU*UU*CU*A*CU*C*UU*G*UAGAUCUGAUGG U*CCAU*GUCU*G*U*UACUC* (SEQ ID NO:32) | 13947.1 | 13944.2 |
| **Stem-engineered crRNAs targeting *DNMT1-3* locus** | | | | |
| 23 | crSplit-L | UAAUUCUACUC (SEQ ID NO:33) | 3678.5 | 3677.8 |
| | crSplit-R | UUGUAGAUCUGAUGGUCCAUGUCUGUU ACUC (SEQ ID NO:34) | 9812.1 | 9811.4 |
| 24 | crDel2 | UAAUU-CUACUCUUGUAG-UCGAUGG UCCAUGUCUGUUACUC (SEQ ID NO:35) | 12917.1 | 12916.2 |
| 25 | crDel4 | UAAUUUCU--UCUU---- AGAUCUGAUGGUC CAUGUCUGUUACUC (SEQ ID NO:36) | 12266.7 | 12266.4 |
| 26 | crDel8 | UAAUUU-----UCUU----AUCUGAUGGUCCA UGUCUGUUACUC (SEQ ID NO:37) | 10980.9 | 10980.9 |
| 27 | crIns4 | UAAUUCUAC*A*CUCUUG*U*GUAGAUCUG AUGGUCCAUGUCUGUUACUC (SEQ ID NO:38) | 14838.3 | 14837.7 |
| 28 | crIns4' | UAAUUCUAC*UC*UCUUG*U*GUAGAUCUG AUGGUCCAUGUCUGUUACUC (SEQ ID NO:39) | 14815.3 | 14813.5 |
| 29 | crIns6' | UAAUUCUAC*UGC*UCUUG*CU*GUAGAUC UGAUGGUCCAUGUCUGUUACUC (SEQ ID NO:40) | 15465.6 | 15463.9 |
| 30 | crIns8 | UAAUUCUAC*ACAC*UCUUG*UGUG*UAGA UCUGAUGGUCCAUGUCUGUUACUC (SEQ ID NO:41) | 16124.1 | 16123.5 |
| 31 | crIns12 | UAAUUCUAC*ACACAC*UCUUG*UGUGUG* UAGAUCUGAUGGUCCAUGUCUGUUACU C (SEQ ID NO:42) | 17409.8 | 17408.7 |
| Loop-engineered crRNAs targeting DNMT1-3 locus | | | | |
| 32 | FncrRNA | UAAUUCUAC*U*GUUGUAGAUCUGAUGG UCCAUGUCUGUUACUC (SEQ ID NO:43) | 13592.5 | 13593.0 |
| 33 | Lb3crRNA | UAAUUCUAC*G*UU*C*UGUAGAUCUGAUG GUCCAUGUCUGUUACUC (SEQ ID NO:44) | 13897.7 | 13898.2 |
| 34 | BpcrRNA | UAAUUCUAC*GUAA*UGUAGAUCUGAUG GUCCAUGUCUGUUACUC (SEQ ID NO:45) | 13944.7 | 13945.6 |
| 35 | Pb/Pe/LicrRNA | UAAUUCUAC*UUU*UGUAGAUCUGAUGG UCCAUGUCUGUUACUC (SEQ ID NO:46) | 13553.5 | 13553.6 |
| 36 | SscrRNA | UAAUUCUAC*ACGCG*GUAGAUCUGAUG GUCCAUGUCUGUUACUC (SEQ ID NO:47) | 13958.7 | 13959.3 |
| 37 | Lb2/Pc/PmcrRNA | UAAUUCUACU*A*UUGUAGAUCUGAUGG UCCAUGUCUGUUACUC (SEQ ID NO:48) | 13576.5 | 13577.3 |

*FIG. 19 (CONT. 1)*

| 38 | CMtcrRNA | UAAUUCUACUC*U*UGUAGAUCUGAUG GUCCAUGUCUGUUACUC (SEQ ID NO:49) | 13858.7 | 13859.1 |
| 39 | EecrRNA | UAAUUCUACU-UUGUAGAUCUGAUG GUCCAUGUCUGUUACUC (SEQ ID NO:50) | 13247.3 | 13247.4 |
| 40 | MbcrRNA | UAAUUCUACUG*U*UGUAGAUCUGAUG GUCCAUGUCUGUUACUC (SEQ ID NO:51) | 13898.7 | 13898.6 |
| 41 | PdcrRNA | UAAUUCUACU*UC*GGUAGAUCUGAUGG UCCAUGUCUGUUACUC (SEQ ID NO:52) | 13591.5 | 13592.4 |
| 42 | LbcrRNA | AAUUCUACU*AA*GUGUAGAUCUGAUGG UCCAUGUCUGUUACUC (SEQ ID NO:53) | 13638.5 | 13637.2 |
| **Chemically modified crRNAs targeting *AAVS1* locus** | | | | |
| WT | crWT | UAAUUCUACUCUUGUAGAUCUUACGA UGGAGCCAGAGAGGAU (SEQ ID NO:9) | 13763.5 | 13763.2 |
| 1 | cr3'5F | UAAUUCUACUCUUGUAGAUCUUACGA UGGAGCCAGAGAGGAU (SEQ ID NO:54) | 13773.5 | 13772.2 |
| **Chemically modified crRNAs targeting *FANCF-2* locus** | | | | |
| WT | crWT | UAAUUCUACUCUUGUAGAUGUCGGCA UGGCCCCAUUCGCACG (SEQ ID NO:10) | 13627.4 | 13625.6 |
| 1 | cr3'5F | UAAUUCUACUCUUGUAGAUGUCGGCA UGGCCCCAUUCGCACG (SEQ ID NO:55) | 13637.4 | 13635.6 |

| No. | LbcrRNA | Modification pattern (5'- to -3') | M.W. | |
|---|---|---|---|---|
| Chemically modified crRNAs targeting DNMT1-3 locus | | | Calcd. | Found |
| WT | crWT | AAUUCUACUAAGUGUAGAUCUGAUGG UCCAUGUCUGUUACUC (SEQ ID NO:8) | 13638.5 | 13637.2 |
| 1 | cr3'5F | AAUUCUACUAAGUGUAGAUCUGAUGG UCCAUGUCUGUUACUC (SEQ ID NO:56) | 13648.5 | 13648.0 |

Unmodified nucleotides are shown in black. Full-length PS modifications are underlined. 2'-*O*-methyl modifications are italized. 2'-F modifications are shaded. 2'-*O*-methyl combined with PS modifications are italicized and underlined. 2'-F combined with PS modifications are in shaded and underlined. Unlocked nucleotides are shown in bold. Locked nucleotides are shown in a box. A dash denotes deleted nucleotides. (This applies to all sequences other than sequences 23-42 in the table above).
Underlined letters for sequences 23-31 denotes inserted nucleotides. Underlined letters in the loop for sequences 32-42 above denotes nucleotides difference between AscrRNA and other crRNAs.

| No. | crRNA | Modification pattern (5'- to -3') | M.W. | |
|---|---|---|---|---|
| Chemically modified crRNAs targeting DNMT1-3 locus | | | Calcd. | Found |
| WT | crWT | UAAUUCUACUCUUGUAGAUCUGAUGG UCCAUGUCUGUUACUC (SEQ ID NO:3) | 13552.5 | 13552.2 |
| 1 | cr16M5F | UAAU*UU*CUACUC*UU*GU*AG*AUCUGAUGG | 13786.5 | 13783.7 |

*FIG. 19 (CONT. 2)*

| | | UCCA*U*GUCUGU*U*A*C*U*C* (SEQ ID NO:57) | | |
|---|---|---|---|---|
| 2 | cr16M10PS5F | UAAU*UU*CU*A*CU*CUU*GU*AGA*UCUGAUGG UCCA*U*GUCUGU*U*A*C*U*C (SEQ ID NO:58) | 13947.1 | 13944.2 |
| 3 | cr10PS5F | UAAU*UU*CU*A*CU*CUU*GU*AGA*UCUGAUGG UCCAUGUCUGU*U*A*C*U*C (SEQ ID NO:59) | 13723.1 | 13719.3 |
| 4 | crI21F | UAAU*UU*CU*A*CU*CUU*GU*AGA*UCUGAUGG UCC*A*UGUCUGU*U*A*C*U*C (SEQ ID NO:60) | 13594.5 | 13594.2 |
| 5 | crI10F | UAAUUUCUACUCUUGUAGAUCUGAUGG UCC*A*UGUCUGU*U*A*C*U*C (SEQ ID NO:61) | 13572.5 | 13572.5 |
| 6 | crI3F | UAAUUUCUACUCUUGUAGAUCUGAUGG UCCAUGUCUGU*U*A*C*U*C (SEQ ID NO:62) | 13558.5 | 13557.6 |
| 7 | crI1F | UAAUUUCUACUCUUGUAGAUCUGAUGG UCCAUGUCUGUUAC*U*C (SEQ ID NO:63) | 13554.5 | 13553.8 |
| 8 | cr21H | UAAUuuCUacUcuuGuagaUCUGAUGGUccau GUCUgUuacuc (SEQ ID NO:64) | 13328.5 | 13328.9 |
| 9 | cr10H | UAAUUUCUACUCUUGUAGAUCUGAUGG UccauGUCUgUuacuc (SEQ ID NO:65) | 13450.5 | 13450.2 |
| 10 | cr5H | UAAUUUCUACUCUUGUAGAUCUGAUGG UCCAUGUCUGUuacuc (SEQ ID NO:66) | 13500.5 | 13500.3 |
| 11 | Ψ-crRNA | UAAUUUCUACUCUUGUAGAUCUGAUGG UCCAUGUCUGUUACUC (SEQ ID NO:67) | | |
| 12 | 5meC-crRNA | UAAUUUCUACUCUUGUAGAUCUGAUG GUCCAUGUCUGUUACUC (SEQ ID NO:68) | | |
| 13 | 5moU-crRNA | UAAUUUCUACUCUUGUAGAUCUGAUGG UCCAUGUCUGUUACUC (SEQ ID NO:69) | | |
| 14 | m1A-crRNA | UAAUUUCUACUCUUGUAGAUCUGAUGG UCCAUGUCUGUUACUC (SEQ ID NO:70) | | |
| 15 | cr7PS21F | UAAU*UU*CU*A*CU*UU*GU*AGA*UCUGAUGG U*CC*A*U*GUCUGU*U*A*C*U*C (SEQ ID NO:71) | | |
| 16 | cr3PS21F | UAAU*UU*CU*A*CU*UU*GU*AGA*UCUGAUGG U*CC*A*U*GUCUGU*U*A*C*U*C (SEQ ID NO:72) | | |
| 17 | cr5'5F+5F | UAAUUUCUACUCUUGUAGAUCUGAUGG UCCAUGUCUGUUACUCGCCUG (SEQ ID NO:73) | | |

*FIG. 19 (CONT. 3)*

| Locus | Genome | Location | Protospacer(5'-3') | Mismatch (bp) | Strand |
|---|---|---|---|---|---|
| DNMT1-3 On target | Homo sapiens | NC_000019.10 | TTTCCTGATGGTCCATG TCTGTTACTC (SEQ ID NO:74) | 0 | - |
| DNMT1-3 OT1 | Homo sapiens | NC_000007.14 | TTTCCTGCTGGTCCATG TCTAATACTC (SEQ ID NO:75) | 3 | - |
| DNMT1-3 OT2 | Homo sapiens | NC_000016.10 | TTTTCTGATGGTCCATA CCTGTTACAC (SEQ ID NO:76) | 3 | + |
| DNMT1-3 OT3 | Homo sapiens | NC_000011.10 | TTTTCTTATTGTACATG TCTGTAACTC (SEQ ID NO:77) | 4 | - |
| DNMT1-3 OT4 | Homo sapiens | NC_000023.11 | TTTCCTGATGGTCCACA CCTGTTACAC (SEQ ID NO:78) | 4 | + |
| AAVS1 On target | Homo sapiens | NC_000019.10 | TTTGCTTACGATGGAGC CAGAGAGGAT (SEQ ID NO:79) | 0 | - |
| FANCF-2 On target | Homo sapiens | NC_000011.10 | TTTGGTCGGCATGGCCC CATTCGCACG (SEQ ID NO:80) | 0 | - |

| Locus | Forward primer | Reverse primer | Amplicon (bp) | Predicted fragment (bp) |
|---|---|---|---|---|
| DNMT1-3 On target | CTGGGACTCAGGCG GGTCAC (SEQ ID NO:81) | CCTCAGCCAGAAG TCCCGTGC (SEQ ID NO:82) | 827 | 358 + 469 |
| DNMT1-3 OT1 | AGGAAAGCCATGCC AGAGACTCA (SEQ ID NO:83) | CACCGCCACTCTG TTTCCAAG (SEQ ID NO:84) | 800 | 341 + 459 |
| DNMT1-3 OT2 | GTTGGGACATGAAG GTCAAGTGTG (SEQ ID NO:85) | TTTGTCTCCTGTTG CCTTCAGGCC (SEQ ID NO:86) | 788 | 296 + 492 |
| DNMT1-3 OT3 | GAGGCATAGCAAGG TCATGCCTTT (SEQ ID NO:87) | TGCTTCCCTTGGTG GAGCTG (SEQ ID NO:88) | 923 | 424 + 499 |
| DNMT1-3 OT4 | TTTCCATGTAGGCCC ATGCCC (SEQ ID NO:89) | CCAGGTTACCAGC AACAGATCTC (SEQ ID NO:90) | 800 | 313 + 487 |

*FIG. 20*

| AAVS1 On target | GGGCTGGCTACTGGC CTTAT (SEQ ID NO:91) | ATGGCATCTTCCA GGGGTCC (SEQ ID NO:92) | 700 | 314 + 386 |
| --- | --- | --- | --- | --- |
| FANCF-2 On target | AGCTCCGCCTGGGTC TTCAT (SEQ ID NO:93) | GCGGAGACGTTCA TGACTGG (SEQ ID NO:94) | 800 | 341 + 459 |
| PAM is in bold; Mismatched bases are underlined. | | | | |

*FIG. 20 (CONT. 2)*

| Locus | Forward Primer for 1st stage PCR | Reverse Primer for 1st stage PCR |
|---|---|---|
| DNMT1-3 On target | TCGTCGGCAGCGTCAGATGTGTATAAGAGACAGTCCCTCACTCCTGCTCGGTGAA (SEQ ID NO:95) | GTCTCGTGGGCTCGGAGATGTGTATAAGAGACAGAAGTCACTCTGGGGAACACGCC (SEQ ID NO:96) |
| DNMT1-3 OT1 | TCGTCGGCAGCGTCAGATGTGTATAAGAGACAGACCTTTTGGGCGTGGAGAAGGG (SEQ ID NO:97) | GTCTCGTGGGCTCGGAGATGTGTATAAGAGACAGGGGAGGGGGTCAGCATGAAAGG (SEQ ID NO:98) |
| DNMT1-3 OT2 | TCGTCGGCAGCGTCAGATGTGTATAAGAGACAGCTCCCCACCCCCTAGGAAAGT (SEQ ID NO:99) | GTCTCGTGGGCTCGGAGATGTGTATAAGAGACAGCCCTTTCTGGTGGAGTGTCCCC (SEQ ID NO:100) |
| DNMT1-3 OT3 | TCGTCGGCAGCGTCAGATGTGTATAAGAGACAGTGAAGGTATAGGAGAGGTTTTGGGCT (SEQ ID NO:101) | GTCTCGTGGGCTCGGAGATGTGTATAAGAGACAGAGACGACCTTAGATGGAGTGTTGTGT (SEQ ID NO:102) |
| DNMT1-3 OT4 | TCGTCGGCAGCGTCAGATGTGTATAAGAGACAGTGCCAGTGGAAGGAGGGAGTGT (SEQ ID NO:103) | GTCTCGTGGGCTCGGAGATGTGTATAAGAGACAGTGCCCAGGAAGTTGCTTCTCCC (SEQ ID NO:104) |

*FIG. 21*

MODIFIED CPF1 MRNA, MODIFIED GUIDE RNA, AND USES THEREOF

CROSS REFERENCE TO RELATED APPLICATIONS

This application is a national stage application filed under 35 U.S.C. § 371 of PCT/US2017/027762 filed Apr. 14, 2017, which claims the benefit of U.S. Provisional Patent Application Ser. No. 62/323,683, filed Apr. 16, 2016, U.S. Provisional Patent Application Ser. No. 62/328,741, filed Apr. 28, 2016, U.S. Provisional Patent Application Ser. No. 62/385,471, filed Sep. 9, 2016, and U.S. Provisional Patent Application Ser. No. 62/400,843, filed Sep. 28, 2016, each of which are expressly incorporated herein by reference.

STATEMENT REGARDING FEDERALLY SPONSORED RESEARCH

This invention was made with Government Support under Grant No. 1R01HL136652 awarded by the National Heart, Lung, and Blood Institute. The Government has certain rights to the invention.

FIELD OF THE INVENTION

The present disclosure generally relates to systems, methods and compositions for use in Clustered Regularly Interspaced Short Palindromic Repeats (CRISPR)-Cpf1 genome editing systems. Disclosed herein are modified Cpf1 mRNAs, modified guide RNAs, and combinations thereof, that confer increased levels of genome editing.

BACKGROUND

The bacterial type II CRISPR-Cas9 genome editing method has recently received a great deal of interest in the field of genome engineering. The co-expression of a single Cas9 protein isolated from *Streptococcus pyogenes* with a chimeric single guide RNA (sgRNA) can precisely create double stranded breaks (DSBs) in a genome. The Cas9 protein is directed to a precise DNA sequence in the genome by a twenty nucleotide target sequence present in the sgRNA, which guides the Cas9 protein to create the DSB. The presence of a double-stranded break in genomic DNA dramatically increases the rate of homologous recombination.

Recently, an additional genome editing system, termed the CRISPR-Cpf1 system, was identified (Zetsche, B. et al. Cpf1 is a single RNA-guided endonuclease of a class 2 CRISPR-Cas system. Cell. 2015 Oct. 22; 163(3):759-71). Cpf1 cleaves DNA in a staggered pattern and leaves sticky ends, as compared to the cleaved blunt DNA ends left by the Cas9 enzyme. In addition, Cpf1 only requires one guide RNA rather than the two (tracrRNA and crRNA) needed by Cas9 for cleavage (or a chimeric single guide RNA). However, gene editing frequencies are still very low, and thus new methods are needed to improve the efficiency of the CRISPR-Cpf1 gene editing system.

Messenger RNAs (mRNAs) encoding functional proteins have demonstrated their therapeutic potential in fundamental and clinical studies. For example, immunotherapy with mRNA-electroporated dendritic cell provided therapeutic benefit in several cancer clinical trials. mRNAs were also utilized to produce chimeric antigen receptors in T cells for adoptive T-cell therapy, to express functional proteins for protein replacement therapy, and most recently, to make nucleases for gene engineering. Although there have been significant advances in mRNA-based therapeutics in the past decade, instability and immunogenicity of mRNA hinders its therapeutic application in humans.

The systems, methods, and compositions disclosed herein address these and other needs.

SUMMARY

Disclosed herein are systems, methods, and compositions that utilize modified Cpf1 mRNAs, modified guide RNAs, and combinations thereof. These modified RNAs can be used in the CRISPR-Cpf1 genome editing system. These modified Cpf1 mRNAs and modified guide RNAs can incorporate a number of chemical changes to the nucleotides, including changes to the nucleobase, the ribose sugar, and/or the phosphodiester linkage; or these changes can include insertions or deletions into the guide RNA sequence. These modified Cpf1 mRNAs, modified guide RNAs, and combinations thereof, can improve efficiency of the CRISPR/Cpf1 genome editing system, reduce off-target effects, reduce toxicity, increase Cpf1 protein levels, increase Cpf1 nuclease activity, increase guide RNA stability, and/or increase Cpf1 mRNA stability.

In one aspect, disclosed herein is a genome editing system comprising:
  a) a guide RNA that hybridizes with a target sequence of a DNA molecule in a eukaryotic cell that contains the DNA molecule, and
  b) an mRNA encoding a Cpf1 protein;
  wherein the mRNA encoding a Cpf1 protein comprises at least one chemically modified nucleotide.

In one embodiment, the guide RNA hybridizes with the target sequence and the Cpf1 protein cleaves the DNA molecule.

In one embodiment, the at least one chemically modified nucleotide confers increased Cpf1 nuclease activity, increased Cpf1 protein levels, decreased off-target effects, reduced toxicity, and/or increased Cpf1 mRNA stability as compared to a corresponding mRNA encoding a Cpf1 protein not having the chemically modified nucleotide. In one aspect, disclosed herein is a genome editing system comprising:
  a) a guide RNA that hybridizes with a target sequence of a DNA molecule in a eukaryotic cell that contains the DNA molecule, and
  b) an mRNA encoding a Cpf1 protein;
  wherein the guide RNA comprises at least one chemically modified nucleotide; and
  wherein the mRNA encoding a Cpf1 protein comprises at least one chemically modified nucleotide.

In one aspect, disclosed herein is a genome editing system comprising:
  a) a guide RNA that hybridizes with a target sequence of a DNA molecule in a eukaryotic cell that contains the DNA molecule, and
  b) a DNA vector comprising a regulatory element operable in a eukaryotic cell operably linked to a nucleotide sequence encoding a Cpf1 protein; an mRNA encoding a Cpf1 protein; or a Cpf1 protein;
  wherein the guide RNA comprises at least one chemically modified nucleotide.

In another aspect, provided herein is a method of RNA-guided genome editing, the method comprising:
introducing into a cell of the subject:
a) a guide RNA that hybridizes with a target sequence of a DNA molecule in a eukaryotic cell that contains the DNA molecule, and
b) an mRNA encoding a Cpf1 protein;
wherein the guide RNA comprises at least one chemically modified nucleotide;
wherein the mRNA encoding a Cpf1 protein comprises at least one chemically modified nucleotide; and
wherein the guide RNA hybridizes with the target sequence and the Cpf1 protein cleaves the DNA molecule.

In another aspect, provided herein is a method of RNA-guided genome editing, the method comprising:
introducing into a cell of the subject:
a) a guide RNA that hybridizes with a target sequence of a DNA molecule in a eukaryotic cell that contains the DNA molecule, and
b) an mRNA encoding a Cpf1 protein;
wherein the mRNA encoding a Cpf1 protein comprises at least one chemically modified nucleotide; and
wherein the guide RNA hybridizes with the target sequence and the Cpf1 protein cleaves the DNA molecule.

In another aspect, provided herein is a method of RNA-guided genome editing, the method comprising:
introducing into a cell of the subject:
a) a guide RNA that hybridizes with a target sequence of a DNA molecule in a eukaryotic cell that contains the DNA molecule, and
b) a DNA vector comprising a regulatory element operable in a eukaryotic cell operably linked to a nucleotide sequence encoding a Cpf1 protein; an mRNA encoding a Cpf1 protein; or a Cpf1 protein;
wherein the guide RNA comprises at least one chemically modified nucleotide; and
wherein the guide RNA hybridizes with the target sequence and the Cpf1 protein cleaves the DNA molecule.

In another aspect, provided herein is a method of increasing Cpf1 protein levels in a cell, the method comprising:
introducing into a cell of the subject:
a) a guide RNA that hybridizes with a target sequence of a DNA molecule in a eukaryotic cell that contains the DNA molecule, and
b) an mRNA encoding a Cpf1 protein;
wherein the mRNA encoding a Cpf1 protein comprises at least one chemically modified nucleotide, and
wherein the at least one chemically modified nucleotide confers increased Cpf1 protein levels as compared to a corresponding mRNA encoding a Cpf1 protein not having the chemically modified nucleotide.

In a further aspect, provided herein is a method of increasing Cpf1 nuclease activity in a cell, the method comprising:
introducing into a cell of the subject:
a) a guide RNA that hybridizes with a target sequence of a DNA molecule in a eukaryotic cell that contains the DNA molecule, and
b) an mRNA encoding a Cpf1 protein;
wherein the mRNA encoding a Cpf1 protein comprises at least one chemically modified nucleotide, and
wherein the at least one chemically modified nucleotide confers increased Cpf1 nuclease activity as compared to a corresponding mRNA encoding a Cpf1 protein not having the chemically modified nucleotide.

In another aspect, provided herein is a method of reducing toxicity of RNA-guided genome editing in a cell, the method comprising:
introducing into a cell of the subject:
a) a guide RNA that hybridizes with a target sequence of a DNA molecule in a eukaryotic cell that contains the DNA molecule, and
b) an mRNA encoding a Cpf1 protein;
wherein the mRNA encoding a Cpf1 protein comprises at least one chemically modified nucleotide, and
wherein the at least one chemically modified nucleotide confers reduced toxicity as compared to a corresponding mRNA encoding a Cpf1 protein not having the chemically modified nucleotide.

In one aspect, disclosed herein is a genome editing system comprising:
a) a guide RNA that hybridizes with a target sequence of a DNA molecule in a eukaryotic cell that contains the DNA molecule, and
b) a DNA vector comprising a regulatory element operable in a eukaryotic cell operably linked to a nucleotide sequence encoding a Cpf1 protein; an mRNA encoding a Cpf1 protein; or a Cpf1 protein;
wherein the guide RNA comprises at least one chemically modified nucleotide, and
wherein the guide RNA hybridizes with the target sequence and the Cpf1 protein cleaves the DNA molecule.

In one embodiment, the at least one chemically modified nucleotide confers increased Cpf1 nuclease activity, decreased off-target effects, reduces toxicity, and/or increased guide RNA stability as compared to a corresponding guide RNA not having the chemical modification.

In another aspect, provided herein is a method of increasing the efficiency of RNA-guided genome editing in a cell, the method comprising:
introducing into a cell of the subject:
a) a guide RNA that hybridizes with a target sequence of a DNA molecule in a eukaryotic cell that contains the DNA molecule, and
b) a DNA vector comprising a regulatory element operable in a eukaryotic cell operably linked to a nucleotide sequence encoding a Cpf1 protein; an mRNA encoding a Cpf1 protein; or a Cpf1 protein;
wherein the guide RNA comprises at least one chemically modified nucleotide, and
wherein the at least one chemically modified nucleotide confers increased Cpf1 nuclease activity as compared to a corresponding guide RNA not having the chemical modification.

In a further aspect, provided herein is a method of decreasing the off-target effects of RNA-guided genome editing in a cell, the method comprising:
introducing into a cell of the subject:
a) a guide RNA that hybridizes with a target sequence of a DNA molecule in a eukaryotic cell that contains the DNA molecule, and
b) a DNA vector comprising a regulatory element operable in a eukaryotic cell operably linked to a nucleotide sequence encoding a Cpf1 protein;
wherein the guide RNA comprises at least one chemically modified nucleotide, and wherein the at least one chemically modified nucleotide confers decreased off-target effects as compared to a corresponding guide RNA not having the chemical modification.

In another aspect, provided herein is a method of reducing toxicity of RNA-guided genome editing in a cell, the method comprising:
introducing into a cell of the subject:
a) a guide RNA that hybridizes with a target sequence of a DNA molecule in a eukaryotic cell that contains the DNA molecule, and
b) a DNA vector comprising a regulatory element operable in a eukaryotic cell operably linked to a nucleotide sequence encoding a Cpf1 protein; an mRNA encoding a Cpf1 protein; or a Cpf1 protein;
wherein the guide RNA comprises at least one chemically modified nucleotide, and
wherein the at least one chemically modified nucleotide confers reducing toxicity as compared to a corresponding guide RNA not having the chemical modification.

BRIEF DESCRIPTION OF THE DRAWINGS

The accompanying figures, which are incorporated in and constitute a part of this specification, illustrate several aspects described below.

FIG. 1 depicts SEQ ID NOs: 3 and 74.

(FIG. 3A) A schematic showing examples of chemical changes to the chemically modified nucleotides utilized for Cpf1 mRNAs. (FIG. 3B) A panel showing examples of chemically modified phosphodiester linkages for the chemically modified nucleotides utilized for Cpf1 mRNAs. Boxed phosphodiester linkage shows the natural unit. (FIG. 3C) A panel showing examples of chemically modified ribose sugar moieties for the chemically modified nucleotides utilized for Cpf1 mRNAs. Boxed riboseshows the natural unit. (FIG. 3D) A panel showing examples of chemically modified nucleobases for the chemically modified nucleotides utilized for Cpf1 mRNAs.

(FIG. 5A) Translation at 30° C. Fold change was normalized by the unmodified FLuc mRNA. (FIG. 5B) Translation at 37° C. Fold change was normalized by the unmodified FLuc mRNA; the inserted figure denoted the Pearson correlation analysis for translation at 30 and 37° C. in the rabbit reticulocyte lysate system.

(FIG. 9A) A panel of chemically modified crRNAs tested in this study. Full-length PS modifications, 2'-O-methyl modifications, 2'-F modifications, 2'-O-methyl combined with PS modifications, and 2'-F combined with PS modifications are shown. (FIG. 9B) Stem engineering of crRNAs. Deleted bases and inserted bases are highlighted. The length of the stem duplex was altered by deletion or insertion of nucleotides. For crSplit, the pseudoknot-like structure was formed by hybridization of two arms of the direct repeat. (FIG. 9C, FIG. 9D) Gene cutting efficiency using modified crRNAs (FIG. 9C) and 5'-handle rearranged crRNAs (FIG. 9D). Unlock and locked nucleotides are shown. The dotted line denotes deleted nt. Lowercase denotes inserted nt. "T" sign in FIG. 9d left panel denotes the split site. Indel (%) was determined by the T7E1 cleavage assay, normalized to that of crWT of each independent experiment. (FIG. 9E) Gene cutting efficiency using chemically modified Cpf1 mRNA. Relative gene cutting efficiency was normalized to indel percentage of the treatment with crWT and plasmid encoding Cpf1. FIG. 9A depicts SEQ ID NOs: 11-27; FIG. 9B depicts part of SEQ ID NOs: 3 and 33-42; FIG. 9C depicts SEQ ID NOs: 3 and 11-29; and FIG. 9D depicts SEQ ID NOs: 3 and 33-42.

(FIG. 11A) (SEQ ID NOs: 74-78). Indel at on-target and predicted top four off-target sites analyzed by deep sequencing at genomic on- and off-target locus. Indel was plotted as the mean of three biological replicates. (FIG. 11B) Representative top ten high-frequent on-target mutagenesis aligned to the target site of DNMT1-3 induced by crWT+AsCpf1 plasmid (top) and cr3'5F+AsCpf1 mRNA (bottom). The unmodified sequence of DNMT1-3 (SEQ ID NO: 74) was termed as 'WT' at the top. Deletions were marked as dotted lines. Numbers on the left referred to the size of deletions. The read ratio of each mutated site was listed on the right side. (FIG. 11C) Plot of representative mutations (insertions, deletions, and substitutions). Size distribution (top panel) and position distribution (bottom panel) of all reads for crWT+AsCpf1 plasmid (left panel) and cr3'5F+Cpf1 mRNA (right panel).

FIG. 15 depicts various modifications to SEQ ID NO: 3.

FIG. 16 includes SEQ ID NOs: 3 and 43-53.

FIG. 19. Engineered crRNAs and their mass spectrometry data. Unmodified nucleotides are shown in black. PS modifications are underlined. 2' O methyl modifications are shown in italics. 2' F modifications are shaded. 2' O methyl combined with PS modifications are underlined and italicized. 2'F combined with PS modifications are shaded and underlined. Lowercase denotes DNA base. For Ψ crRNA, 5meC crRNA, 5moU crRNA and m1A crRNA, correspondent modified nucleotides are in bold (FIG. 15 and FIG. 17). The gene cutting efficiency of these chemically modified cleavage assay and the results are shown in FIG. 18.

FIG. 20. A list of genomic locus and primers used for T7E1 assay. PAM is in bold; Mismatched bases are underlined.

FIG. 21. List of primers used for targeted for target deep sequencing. Shaded nucleotides indicate the Illumina overhang adapter sequences.

DETAILED DESCRIPTION OF THE INVENTION

Figure 1:
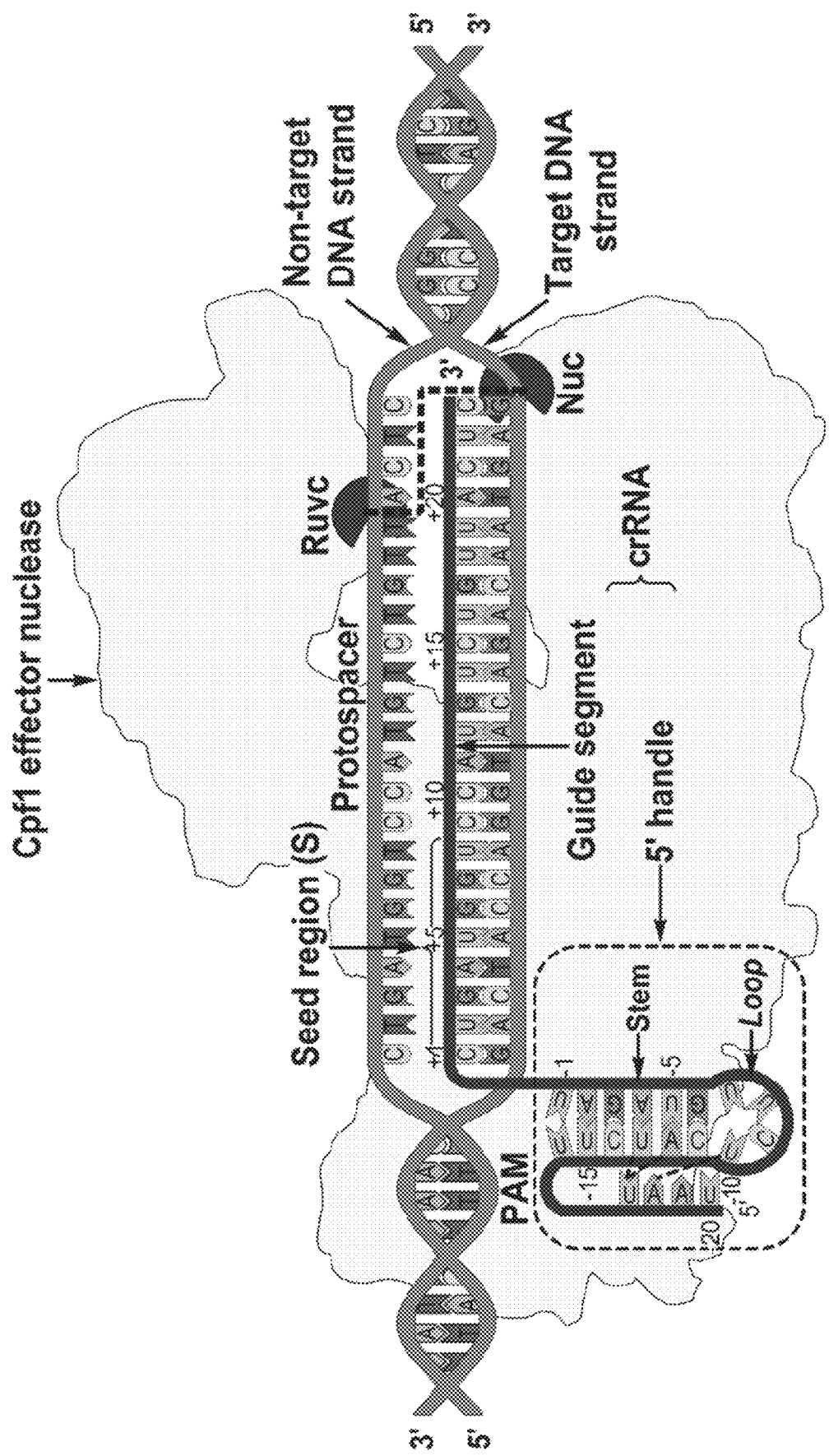
FIG. 1. Schematic illustration of AsCpf1-crRNA-target DNA complex and their terminology. crRNA is composed of a 5' handle (in a pseudoknot structure) and a guide segment (consists of a seed region and 3'-termini).

Disclosed herein are systems, methods, and compositions that utilize modified Cpf1 mRNAs, modified guide RNAs, and combinations thereof. These modified RNAs can be used in the CRISPR-Cpf1 genome editing system. These modified Cpf1 mRNAs and modified guide RNAs can incorporate a number of chemical changes to the nucleotides, including changes to the nucleobase, the ribose sugar, and/or the phosphodiester linkage; or these changes can include insertions or deletions into the guide RNA sequence. These modified Cpf1 mRNAs, modified guide RNAs, and combinations thereof, can improve efficiency of the CRISPR/Cpf1 genome editing system, reduce off-target effects, reduce toxicity, increase Cpf1 protein levels, increase Cpf1 nuclease activity, increase guide RNA stability, and/or increase Cpf1 mRNA stability.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used herein, the article "a," "an," and "the" means "at least one," unless the context in which the article is used clearly indicates otherwise.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.*, 22:1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The term "polynucleotide" refers to a single or double stranded polymer composed of nucleotide monomers. In some embodiments, the polynucleotide is composed of nucleotide monomers of generally greater than 100 nucleotides in length and up to about 8,000 or more nucleotides in length.

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "target" refers to a molecule that has an affinity for a given probe. Targets may be naturally-occurring or man-made molecules. Also, they can be employed in their unaltered state or as aggregates with other species.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-US' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

The term "nucleobase" refers to the part of a nucleotide that bears the Watson/Crick base-pairing functionality. The most common naturally-occurring nucleobases, adenine (A), guanine (G), uracil (U), cytosine (C), and thymine (T) bear the hydrogen-bonding functionality that binds one nucleic acid strand to another in a sequence specific manner.

As used throughout, by a "subject" (or a "host") is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human.

The terms "guide RNA", "gRNA", "CRISPR RNA", or "crRNA" are used interchangeably throughout the specification. This crRNA (or guide RNA) consists of a 5'-handle and a guide segment. Cpf1 protein interacts with the pseudoknot structure formed by the 5'-handle of crRNA (or guide RNA). The guide segment possesses complementary binding with the target DNA sequences.

Genome Editing Systems

In one aspect, disclosed herein is a genome editing system comprising:
a) a guide RNA that hybridizes with a target sequence of a DNA molecule in a eukaryotic cell that contains the DNA molecule, and
b) an mRNA encoding a Cpf1 protein;
wherein the mRNA encoding a Cpf1 protein comprises at least one chemically modified nucleotide, and
wherein the guide RNA hybridizes with the target sequence and the Cpf1 protein cleaves the DNA molecule.

In one aspect, disclosed herein is a genome editing system comprising:
a) a guide RNA that hybridizes with a target sequence of a DNA molecule in a eukaryotic cell that contains the DNA molecule, and
b) a DNA vector comprising a regulatory element operable in a eukaryotic cell operably linked to a nucleotide sequence encoding a Cpf1 protein; an mRNA encoding a Cpf1 protein; or a Cpf1 protein;
wherein the guide RNA comprises at least one chemically modified nucleotide, and
wherein the guide RNA hybridizes with the target sequence and the Cpf1 protein cleaves the DNA molecule.

In one aspect, disclosed herein is a genome editing system comprising:
a) a guide RNA that hybridizes with a target sequence of a DNA molecule in a eukaryotic cell that contains the DNA molecule, and
b) a DNA vector comprising a regulatory element operable in a eukaryotic cell operably linked to a nucleotide sequence encoding a Cpf1 protein;
wherein the guide RNA comprises at least one chemically modified nucleotide, and
wherein the guide RNA hybridizes with the target sequence and the Cpf1 protein cleaves the DNA molecule.

In one aspect, disclosed herein is a genome editing system comprising:
a) a guide RNA that hybridizes with a target sequence of a DNA molecule in a eukaryotic cell that contains the DNA molecule, and
b) an mRNA encoding a Cpf1 protein, wherein the guide RNA comprises at least one chemically modified nucleotide, and
wherein the guide RNA hybridizes with the target sequence and the Cpf1 protein cleaves the DNA molecule.

In one aspect, disclosed herein is a genome editing system comprising:
a) a guide RNA that hybridizes with a target sequence of a DNA molecule in a eukaryotic cell that contains the DNA molecule, and
b) a Cpf1 protein,
wherein the guide RNA comprises at least one chemically modified nucleotide, and
wherein the guide RNA hybridizes with the target sequence and the Cpf1 protein cleaves the DNA molecule.

In one embodiment, the at least one chemically modified nucleotide confers increased Cpf1 nuclease activity, decreased off-target effects, and/or increased guide RNA stability as compared to a corresponding guide RNA not having the chemical modification.

In one aspect, disclosed herein is a genome editing system comprising:
a) a guide RNA that hybridizes with a target sequence of a DNA molecule in a eukaryotic cell that contains the DNA molecule, and
b) an mRNA encoding a Cpf1 protein;
wherein the guide RNA comprises at least one chemically modified nucleotide; and
wherein the mRNA encoding a Cpf1 protein comprises at least one chemically modified nucleotide.

In one aspect, disclosed herein is a genome editing system comprising:
a) a guide RNA that hybridizes with a target sequence of a DNA molecule in a eukaryotic cell that contains the DNA molecule, and
b) a DNA vector comprising a regulatory element operable in a eukaryotic cell operably linked to a nucleotide sequence encoding a Cpf1 protein; an mRNA encoding a Cpf1 protein; or a Cpf1 protein;
wherein the guide RNA comprises at least one chemically modified nucleotide.

In one aspect, disclosed herein is a nucleic acid comprising:
an mRNA encoding a Cpf1 protein;
wherein the mRNA encoding a Cpf1 protein comprises at least one chemically modified nucleotide.

In one embodiment, the at least one chemically modified nucleotide confers increased Cpf1 nuclease activity, increased Cpf1 protein levels, increased Cpf1 translation, decreased off-target effects, reduced toxicity, and/or increased Cpf1 mRNA stability as compared to a corresponding mRNA encoding a Cpf1 protein not having the chemically modified nucleotide.

In one embodiment, the mRNA encoding a Cpf1 protein is encoded by the DNA sequence SEQ ID NO:1, wherein the mRNA encoding a Cpf1 protein comprises at least one chemically modified nucleotide. In one embodiment, the mRNA encoding a Cpf1 protein is encoded by a nucleic acid which is at least 50%, at least 60%, at least 75%, at least 80%, at least 85%, at least 90%, at least 95%, at least 97.5%, or at least 99% identical to the DNA sequence SEQ ID NO:1.

In one embodiment, the mRNA encoding a Cpf1 protein is encoded by the DNA sequence SEQ ID NO:2, wherein the mRNA encoding a Cpf1 protein comprises at least one chemically modified nucleotide. In one embodiment, the mRNA encoding a Cpf1 protein is encoded by a nucleic acid which is at least 50%, at least 60%, at least 75%, at least 80%, at least 85%, at least 90%, at least 95%, at least 97.5%, or at least 99% identical to the DNA sequence SEQ ID NO:2.

In some embodiments, the at least one chemically modified nucleotide comprises a chemically modified nucleobase, a chemically modified ribose, a chemically modified phosphodiester linkage, or a combination thereof.

In some embodiments, the mRNA encoding a Cpf1 protein comprises at least one chemically modified nucleotide selected from a chemically modified nucleobase, a chemically modified ribose, a chemically modified phosphodiester linkage, or a combination thereof.

In some embodiments, the guide RNA comprises at least one chemically modified nucleotide selected from a chemically modified nucleobase, a chemically modified ribose, a chemically modified phosphodiester linkage, or a combination thereof.

In some embodiments, the mRNA encoding a Cpf1 protein comprises at least one chemically modified nucleotide selected from a chemically modified nucleobase, a chemically modified ribose, a chemically modified phosphodiester linkage, or a combination thereof; and the guide RNA comprises at least one chemically modified nucleotide selected from a chemically modified nucleobase, a chemically modified ribose, a chemically modified phosphodiester linkage, or a combination thereof.

In some embodiments, the mRNA encoding a Cpf1 protein comprises a chemically modified nucleobase and the guide RNA comprises a chemically modified ribose.

In some embodiments, the mRNA encoding a Cpf1 protein comprises a pseudouridine ($\Psi$) and the guide RNA comprises a chemically modified ribose.

In some embodiments, the mRNA encoding a Cpf1 protein comprises a chemically modified nucleobase and the guide RNA comprises a 2'-Fluoro (2'-F).

In some embodiments, the mRNA encoding a Cpf1 protein comprises a pseudouridine ($\Psi$) and the guide RNA comprises a 2'-Fluoro (2'-F).

In some embodiments, the chemically modified nucleotides in the mRNA encoding a Cpf1 protein and the chemically modified nucleotides in the guide RNA can be the same type of modification. In some embodiments, the chemically modified nucleotides in the mRNA encoding a Cpf1 protein can be different than the chemically modified nucleotides in the guide RNA.

In one aspect, disclosed herein is a genome editing system comprising:
  a) an engineered guide RNA that hybridizes with a target sequence of a DNA molecule in a eukaryotic cell that contains the DNA molecule, and
  b) a DNA vector comprising a regulatory element operable in a eukaryotic cell operably linked to a nucleotide sequence encoding a Cpf1 protein; an mRNA encoding a Cpf1 protein; or a Cpf1 protein;
  wherein the engineered guide RNA comprises at least one nucleotide insertion or deletion.

In one aspect, disclosed herein is a genome editing system comprising:
  a) an engineered guide RNA that hybridizes with a target sequence of a DNA molecule in a eukaryotic cell that contains the DNA molecule, and
  b) an mRNA encoding a Cpf1 protein;
  wherein the engineered guide RNA comprises at least one nucleotide insertion or deletion; and
  wherein the mRNA encoding a Cpf1 protein comprises at least one chemically modified nucleotide.

In some embodiments, the engineered guide RNA comprises at least one nucleotide insertion. In some embodiments, the engineered guide RNA comprises at least four nucleotide insertions. In some embodiments, the engineered guide RNA comprises from four to twelve nucleotide insertions.

In some embodiments, the engineered guide RNA comprises at least one nucleotide deletion. In some embodiments, the engineered guide RNA comprises at least two nucleotide deletion. In some embodiments, the engineered guide RNA comprises from two to eight nucleotide deletion.

In one embodiment, the guide RNA is split into at least two RNAs. In one embodiment, the guide RNA is split at the stem loop into two RNAs.

Methods

In one aspect, provided herein is a method of RNA-guided genome editing, the method comprising:
  introducing into a cell of the subject:
  a) a guide RNA that hybridizes with a target sequence of a DNA molecule in a eukaryotic cell that contains the DNA molecule, and
  b) an mRNA encoding a Cpf1 protein;
  wherein the mRNA encoding a Cpf1 protein comprises at least one chemically modified nucleotide; and
  wherein the guide RNA hybridizes with the target sequence and the Cpf1 protein cleaves the DNA molecule.

In another aspect, provided herein is a method of RNA-guided genome editing, the method comprising:
  introducing into a cell of the subject:
  a) a guide RNA that hybridizes with a target sequence of a DNA molecule in a eukaryotic cell that contains the DNA molecule, and
  b) an mRNA encoding a Cpf1 protein;
  wherein the guide RNA comprises at least one chemically modified nucleotide;
  wherein the mRNA encoding a Cpf1 protein comprises at least one chemically modified nucleotide; and
  wherein the guide RNA hybridizes with the target sequence and the Cpf1 protein cleaves the DNA molecule.

In another aspect, provided herein is a method of RNA-guided genome editing, the method comprising:
  introducing into a cell of the subject:
  a) a guide RNA that hybridizes with a target sequence of a DNA molecule in a eukaryotic cell that contains the DNA molecule, and
  b) a DNA vector comprising a regulatory element operable in a eukaryotic cell operably linked to a nucleotide sequence encoding a Cpf1 protein; an mRNA encoding a Cpf1 protein; or a Cpf1 protein;
  wherein the guide RNA comprises at least one chemically modified nucleotide; and
  wherein the guide RNA hybridizes with the target sequence and the Cpf1 protein cleaves the DNA molecule.

In another aspect, provided herein is a method of increasing Cpf1 protein levels in a cell, the method comprising:
  introducing into a cell of the subject:
  a) a guide RNA that hybridizes with a target sequence of a DNA molecule in a eukaryotic cell that contains the DNA molecule, and
  b) an mRNA encoding a Cpf1 protein;
  wherein the mRNA encoding a Cpf1 protein comprises at least one chemically modified nucleotide, and
  wherein the at least one chemically modified nucleotide confers increased Cpf1 protein levels as compared to a corresponding mRNA encoding a Cpf1 protein not having the chemically modified nucleotide.

In another aspect, provided herein is a method of increasing Cpf1 protein levels in a cell, the method comprising:
  introducing into a cell of the subject:
  an mRNA encoding a Cpf1 protein;
  wherein the mRNA encoding a Cpf1 protein comprises at least one chemically modified nucleotide, and
  wherein the at least one chemically modified nucleotide confers increased Cpf1 protein levels as compared to a corresponding mRNA encoding a Cpf1 protein not having the chemically modified nucleotide.

In some embodiments, the method further comprises: introducing into a cell of the subject a guide RNA that hybridizes with a target sequence of a DNA molecule in a eukaryotic cell that contains the DNA molecule.

In a further aspect, provided herein is a method of increasing Cpf1 nuclease activity in a cell, the method comprising:
  introducing into a cell of the subject:
  a) a guide RNA that hybridizes with a target sequence of a DNA molecule in a eukaryotic cell that contains the DNA molecule, and
  b) an mRNA encoding a Cpf1 protein;
  wherein the mRNA encoding a Cpf1 protein comprises at least one chemically modified nucleotide, and
  wherein the at least one chemically modified nucleotide confers increased Cpf1 nuclease activity as compared to a corresponding mRNA encoding a Cpf1 protein not having the chemically modified nucleotide.

In a further aspect, provided herein is a method of increasing Cpf1 nuclease activity in a cell, the method comprising:
  introducing into a cell of the subject:
  an mRNA encoding a Cpf1 protein;
  wherein the mRNA encoding a Cpf1 protein comprises at least one chemically modified nucleotide, and
  wherein the at least one chemically modified nucleotide confers increased Cpf1 nuclease activity as compared to a corresponding mRNA encoding a Cpf1 protein not having the chemically modified nucleotide.

In some embodiments, the method further comprises: introducing into a cell of the subject a guide RNA that hybridizes with a target sequence of a DNA molecule in a eukaryotic cell that contains the DNA molecule.

In another aspect, provided herein is a method of reducing toxicity of RNA-guided genome editing in a cell, the method comprising:
  introducing into a cell of the subject:
  a) a guide RNA that hybridizes with a target sequence of a DNA molecule in a eukaryotic cell that contains the DNA molecule, and
  b) an mRNA encoding a Cpf1 protein;
  wherein the mRNA encoding a Cpf1 protein comprises at least one chemically modified nucleotide, and
  wherein the at least one chemically modified nucleotide confers reduced toxicity as compared to a corresponding mRNA encoding a Cpf1 protein not having the chemically modified nucleotide.

In another aspect, provided herein is a method of increasing Cpf1 mRNA levels, the method comprising:
  transcribing a nucleic acid encoding a Cpf1 protein;
  wherein the nucleic acid encoding a Cpf1 protein comprises at least one chemically modified nucleotide, and
  wherein the at least one chemically modified nucleotide confers increased Cpf1 mRNA levels as compared to a corresponding mRNA encoding a Cpf1 protein not having the chemically modified nucleotide.

In another aspect, provided herein is a method of increasing Cpf1 protein levels, the method comprising:
  translating an mRNA encoding a Cpf1 protein;
  wherein the mRNA encoding a Cpf1 protein comprises at least one chemically modified nucleotide, and
  wherein the at least one chemically modified nucleotide confers increased Cpf1 protein levels as compared to a corresponding mRNA encoding a Cpf1 protein not having the chemically modified nucleotide.

In another aspect, provided herein is a method of increasing the efficiency of RNA-guided genome editing in a cell, the method comprising:
  introducing into a cell of the subject:
  a) a guide RNA that hybridizes with a target sequence of a DNA molecule in a eukaryotic cell that contains the DNA molecule, and
  b) a DNA vector comprising a regulatory element operable in a eukaryotic cell operably linked to a nucleotide sequence encoding a Cpf1 protein; an mRNA encoding a Cpf1 protein; or a Cpf1 protein;
  wherein the guide RNA comprises at least one chemically modified nucleotide, and
  wherein the at least one chemically modified nucleotide confers increased Cpf1 nuclease activity as compared to a corresponding guide RNA not having the chemical modification.

In a further aspect, provided herein is a method of decreasing the off-target effects of RNA-guided genome editing in a cell, the method comprising:
  introducing into a cell of the subject:
  a) a guide RNA that hybridizes with a target sequence of a DNA molecule in a eukaryotic cell that contains the DNA molecule, and
  b) a DNA vector comprising a regulatory element operable in a eukaryotic cell operably linked to a nucleotide sequence encoding a Cpf1 protein; an mRNA encoding a Cpf1 protein; or a Cpf1 protein;
  wherein the guide RNA comprises at least one chemically modified nucleotide, and
  wherein the at least one chemically modified nucleotide confers decreased off-target effects as compared to a corresponding guide RNA not having the chemical modification.

In a further aspect, provided herein is a method of reducing toxicity of RNA-guided genome editing in a cell, the method comprising:
  introducing into a cell of the subject:
  a) a guide RNA that hybridizes with a target sequence of a DNA molecule in a eukaryotic cell that contains the DNA molecule, and
  b) a DNA vector comprising a regulatory element operable in a eukaryotic cell operably linked to a nucleotide sequence encoding a Cpf1 protein; an mRNA encoding a Cpf1 protein; or a Cpf1 protein;

wherein the guide RNA comprises at least one chemically modified nucleotide, and wherein the at least one chemically modified nucleotide confers reduced toxicity as compared to a corresponding guide RNA not having the chemical modification.

Previous studies have reported that chemical modifications can improve the stability and potency of various RNAs including siRNA, miRNA and antisense nucleic acids. Recently, chemical modifications were incorporated into guide RNAs for the CRISPR-Cas9 system comprising 2'O-methyl, 3'phosphorothioate, or 3'thioPACE at three terminal nucleotides at both the 5' and 3' ends of gRNAs (Hendel, A. Nature Biotechnology 2015, 33: 985-989). In some embodiments, the guide RNA comprises at least one chemically modified nucleotide.

In some embodiments, the at least one chemically modified nucleotide comprises a chemically modified nucleobase, a chemically modified ribose, a chemically modified phosphodiester linkage, or a combination thereof.

In some embodiments, the mRNA encoding a Cpf1 protein comprises at least one chemically modified nucleotide selected from a chemically modified nucleobase, a chemically modified ribose, a chemically modified phosphodiester linkage, or a combination thereof.

In some embodiments, the guide RNA comprises at least one chemically modified nucleotide selected from a chemically modified nucleobase, a chemically modified ribose, a chemically modified phosphodiester linkage, or a combination thereof.

In some embodiments, the mRNA encoding a Cpf1 protein comprises at least one chemically modified nucleotide selected from a chemically modified nucleobase, a chemically modified ribose, a chemically modified phosphodiester linkage, or a combination thereof; and the guide RNA comprises at least one chemically modified nucleotide selected from a chemically modified nucleobase, a chemically modified ribose, a chemically modified phosphodiester linkage, or a combination thereof.

In some embodiments, the mRNA encoding a Cpf1 protein comprises a chemically modified nucleobase and the guide RNA comprises a chemically modified ribose.

In some embodiments, the mRNA encoding a Cpf1 protein comprises a pseudouridine (Ψ) and the guide RNA comprises a chemically modified ribose.

In some embodiments, the mRNA encoding a Cpf1 protein comprises a chemically modified nucleobase and the guide RNA comprises a 2'-Fluoro (2'-F).

In some embodiments, the mRNA encoding a Cpf1 protein comprises a pseudouridine (Ψ) and the guide RNA comprises a 2'-Fluoro (2'-F).

In one aspect, disclosed herein is a method of RNA-guided genome editing, the method comprising:

introducing into a cell of the subject:

a) an engineered guide RNA that hybridizes with a target sequence of a DNA molecule in a eukaryotic cell that contains the DNA molecule, and b) a DNA vector comprising a regulatory element operable in a eukaryotic cell operably linked to a nucleotide sequence encoding a Cpf1 protein; an mRNA encoding a Cpf1 protein; or a Cpf1 protein;

wherein the engineered guide RNA comprises at least one nucleotide insertion or deletion; and wherein the guide RNA hybridizes with the target sequence and the Cpf1 protein cleaves the DNA molecule.

In one aspect, disclosed herein is a method of RNA-guided genome editing, the method comprising:

introducing into a cell of the subject:

a) an engineered guide RNA that hybridizes with a target sequence of a DNA molecule in a eukaryotic cell that contains the DNA molecule, and b) an mRNA encoding a Cpf1 protein;

wherein the engineered guide RNA comprises at least one nucleotide insertion or deletion; and wherein the mRNA encoding a Cpf1 protein comprises at least one chemically modified nucleotide; and wherein the guide RNA hybridizes with the target sequence and the Cpf1 protein cleaves the DNA molecule.

In some embodiments, the engineered guide RNA comprises at least one nucleotide insertion. In some embodiments, the engineered guide RNA comprises at least four nucleotide insertions. In some embodiments, the engineered guide RNA comprises from four to twelve nucleotide insertions.

In some embodiments, the engineered guide RNA comprises at least one nucleotide deletion. In some embodiments, the engineered guide RNA comprises at least two nucleotide deletion. In some embodiments, the engineered guide RNA comprises from two to eight nucleotide deletion.

Chemically Modified Nucleobases

In one embodiment, the at least one chemically modified nucleotide is a chemically modified nucleobase. In some embodiments, the mRNA encoding a Cpf1 protein comprises a chemically modified nucleobase. In some embodiments, the guide RNA comprises a chemically modified nucleobase.

In one embodiment, the chemically modified nucleobase is selected from 5-formylcytidine (5fC), 5-methylcytidine (5meC), 5-methoxycytidine (5moC), 5-hydroxycytidine (5hoC), 5-hydroxymethylcytidine (5hmC), 5-formyluridine (5fU), 5-methyluridine (5-meU), 5-methoxyuridine (5moU), 5-carboxymethylesteruridine (5camU), pseudouridine (Ψ), N1-methylpseudouridine (me$^1$Ψ), N$^6$-methyladenosine (me$^6$A), or thienoguanosine (G).

In some embodiments, the chemically modified nucleobase is selected from 5-methoxyuridine (5moU), pseudouridine (Ψ), and N$^1$-methylpseudouridine (me$^1$Ψ). In some embodiments, the chemically modified nucleobase is 5-methoxyuridine (5moU). In some embodiments, the chemically modified nucleobase is pseudouridine (Ψ). In some embodiments, the chemically modified nucleobase is N$^1$-methylpseudouridine (me$^1$Ψ).

In some embodiments, the at least one chemically modified nucleobase comprises N$^1$-methylpseudouridine (me$^1$Ψ) and 5-methylcytidine (5meC). In some embodiments, the at least one chemically modified nucleobase comprises pseudouridine (Ψ) and 5-methylcytidine (5meC). In some embodiments, the at least one chemically modified nucleobase comprises 5-methyluridine (5-meU) and 5-methoxycytidine (5moC). In some embodiments, the at least one chemically modified nucleobase comprises 5-methyluridine (5-meU) and 5-hydroxymethylcytidine (5hmC).

The structures of these modified nucleobases are shown below:

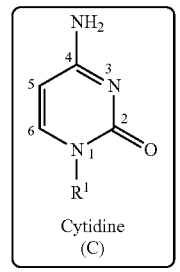
Cytidine (C)

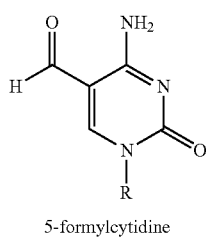
5-formylcytidine (5fC)

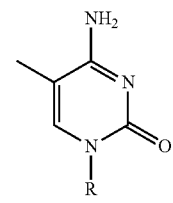
5-methylcytidine (5meC)

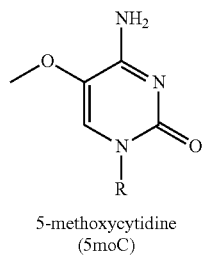
5-methoxycytidine (5moC)

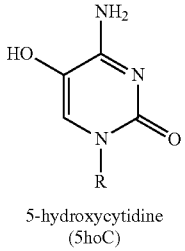
5-hydroxycytidine (5hoC)

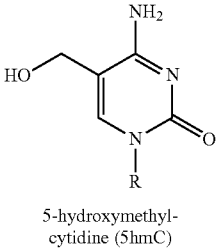
5-hydroxymethyl-cytidine (5hmC)

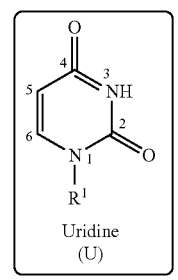
Uridine (U)

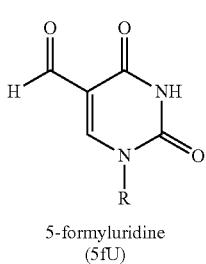
5-formyluridine (5fU)

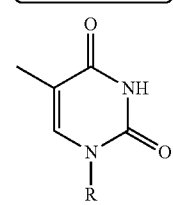
5-methylcytidine (5meU)

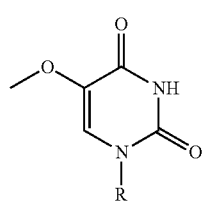
5-methoxy-uridine (5moU)

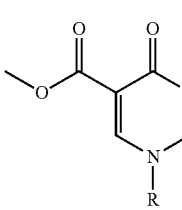
5-carboxy-methyl-esteruridine (5camU)

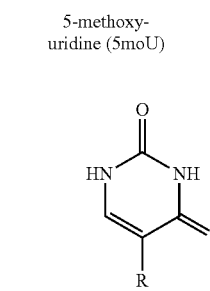
pseudouridine (ψ)

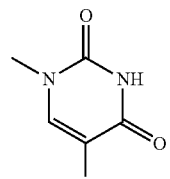
$N^1$-methylpseudo-uridine (me$^1$ψ)

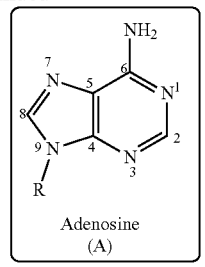
Adenosine (A)

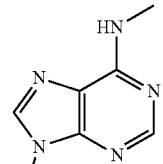
$N^6$ Methyladenosine (me$^6$A)

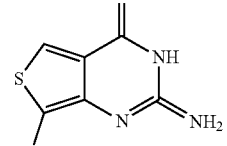
Guanosine (G)

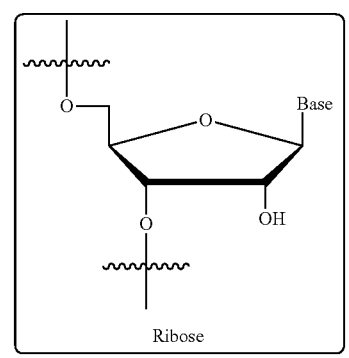
Thienoguanosine ($^{th}$G)

R = ribose

Chemically Modified Ribose Moieties

In one embodiment, the at least one chemically modified nucleotide is a chemically modified ribose. In some embodiments, the mRNA encoding a Cpf1 protein comprises a chemically modified ribose. In some embodiments, the guide RNA comprises a chemically modified ribose.

In one embodiment, the chemically modified ribose is selected from 2'-O-methyl (2'-O-Me), 2'-Fluoro (2'-F), 2'-de-oxy-2'-fluoro-beta-D-arabino-nucleic acid (2'F-ANA), 4'-S, 4'-SFANA, 2'-azido, UNA, 2'-O-methoxy-ethyl (2'-O-ME), 2'-O-Allyl, 2'-O-Ethylamine, 2'-O-Cyanoethyl, Locked nucleic acid (LAN), Methylene-cLAN, N-MeO-amino BNA, or N-MeO-aminooxy BNA. In one embodiment, the chemically modified ribose is selected from 2'-O-methyl (2'-O-Me) or 2'-Fluoro (2'-F).

The structures of these modified riboses are shown below:

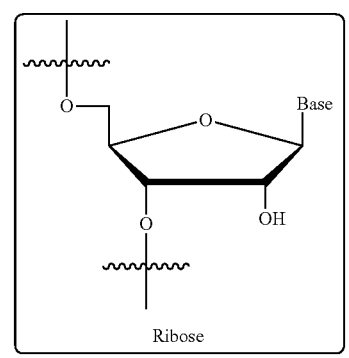
Ribose

-continued
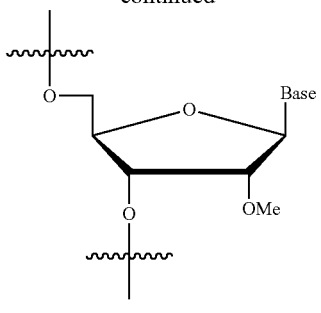
2'-O-methyl
(2'-O-Me)
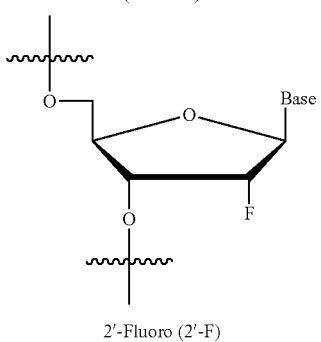
2'-Fluoro (2'-F)
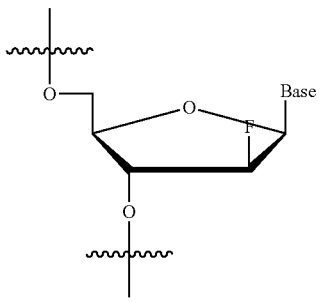
2'-deoxy-2'-fluoro-beta-D-arabino-
nucleic acid (2'F-ANA)
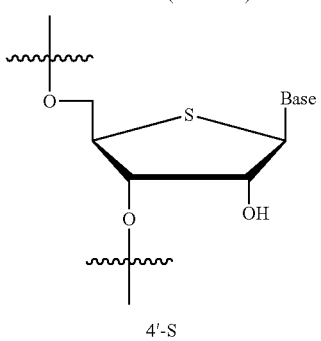
4'-S
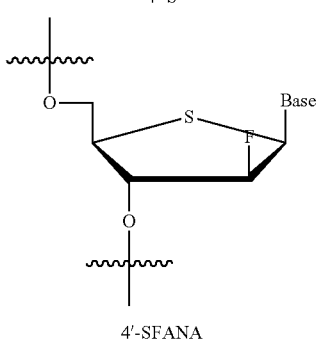
4'-SFANA
-continued
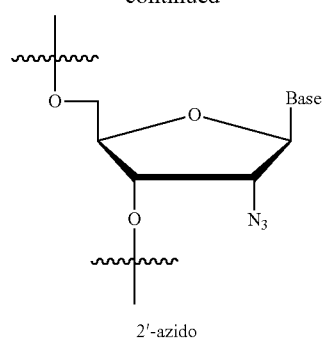
2'-azido
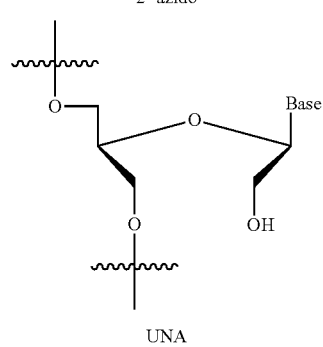
UNA
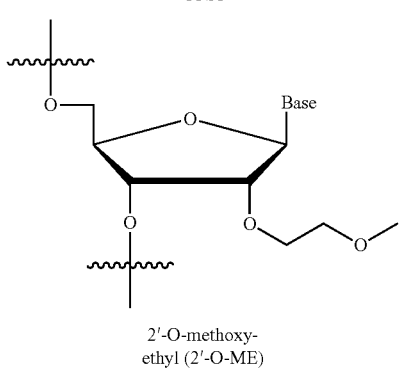
2'-O-methoxy-
ethyl (2'-O-ME)
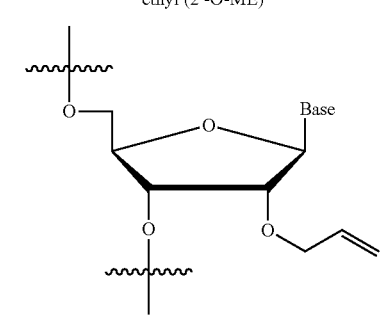
2'-O-Allyl
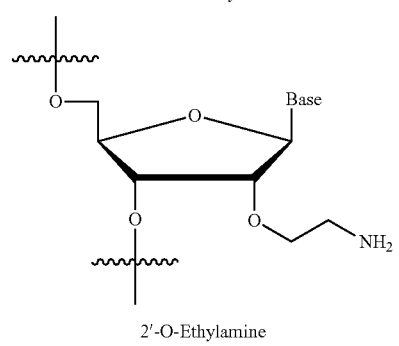
2'-O-Ethylamine

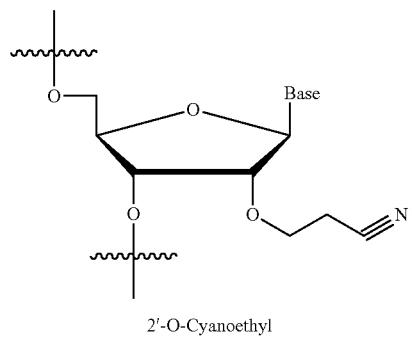

2'-O-Cyanoethyl

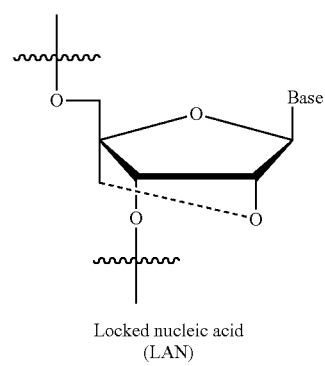

Locked nucleic acid
(LAN)

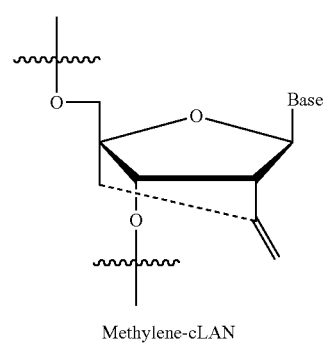

Methylene-cLAN

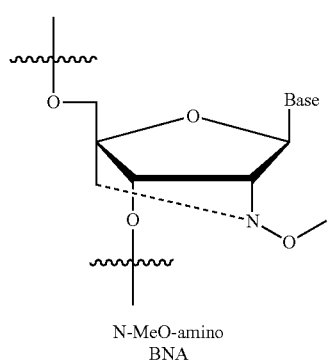

N-MeO-amino
BNA

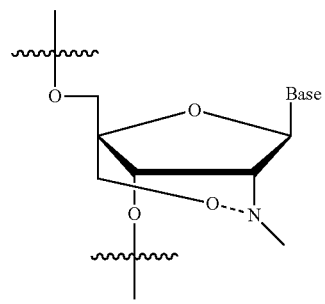

N-MeO-aminooxy BNA

Chemically Modified Phosphodiester Backbone

In one embodiment, the at least one chemically modified nucleotide is a chemically modified phosphodiester linkage. In some embodiments, the mRNA encoding a Cpf1 protein comprises a chemically modified phosphodiester linkage. In some embodiments, the guide RNA comprises a chemically modified phosphodiester linkage.

In one embodiment, the chemically modified phosphodiester linkage is selected from Phosphorothioate (PS), Boranophosphate, phosphodithioate (PS2), 3',5'-amide, N3'-phosphoramidate (NP), Phosphodiester (PO), or 2',5'-phosphodiester (2',5'-PO). In one embodiment, the chemically modified phosphodiester linkage is phosphorothioate.

The structures of these modified phosphodiester linkages are shown below:

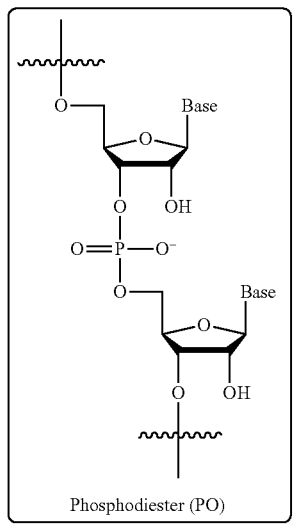

Phosphodiester (PO)

-continued
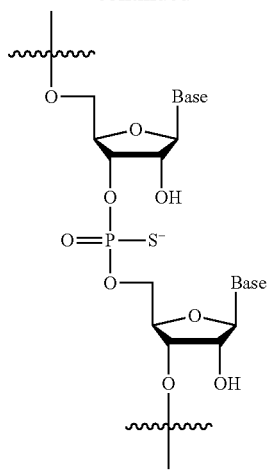
Phosphorothioate (PS)
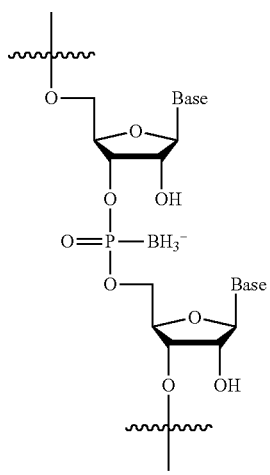
Boranophosphate
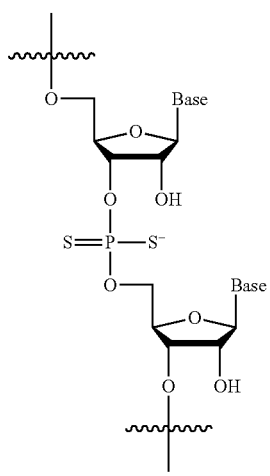
Phosphodithioate (PS2)
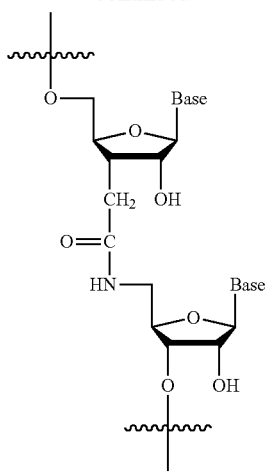
3',5'-amide
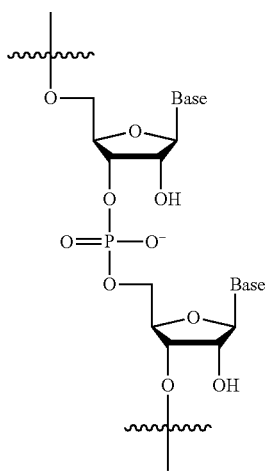
N3'-phosphoramidate (NP)
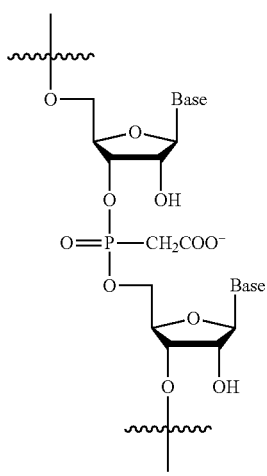
Phosphodiester (PO)

-continued

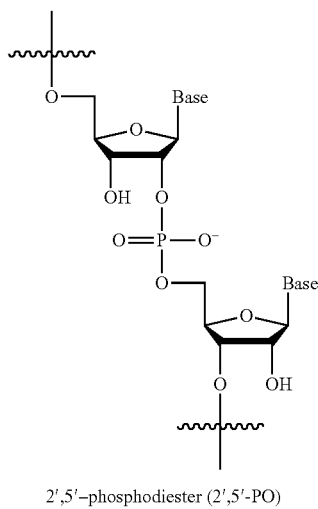

2',5'-phosphodiester (2',5'-PO)

In one aspect, the invention provides a kit comprising one or more of the components described herein. In some embodiments, the kit comprises instructions for using the kit. In some embodiments, the kit comprises:
a) a guide RNA that hybridizes with a target sequence of a DNA molecule in a eukaryotic cell that contains the DNA molecule, and
b) an mRNA encoding a Cpf1 protein;
wherein the mRNA encoding a Cpf1 protein comprises at least one chemically modified nucleotide, and
wherein the guide RNA hybridizes with the target sequence and the Cpf1 protein cleaves the DNA molecule.

In one embodiment, the invention provides a method of modifying a target polynucleotide in a eukaryotic cell. In one embodiment, the invention provides a method of modifying expression of a polynucleotide in a eukaryotic cell.

In some embodiments, an enzyme coding sequence encoding a Cpf1 protein is codon optimized for expression in particular cells, such as eukaryotic cells. In some embodiments, the DNA sequence encoding a Cpf1 protein is similar, or shares substantial identity with SEQ ID NO:1. In one embodiment, the mRNA encoding a Cpf1 protein is encoded by SEQ ID NO:1. In one embodiment, the mRNA encoding a Cpf1 protein is encoded by a nucleic acid which is at least 50%, at least 60%, at least 75%, at least 80%, at least 85%, at least 90%, at least 95%, at least 97.5%, or at least 99% identical to SEQ ID NO:1.

In some embodiments, an enzyme coding sequence encoding a Cpf1 protein is codon optimized for expression in particular cells, such as eukaryotic cells. In some embodiments, the DNA sequence encoding a Cpf1 protein is similar, or shares substantial identity with SEQ ID NO:2. In one embodiment, the mRNA encoding a Cpf1 protein is encoded by SEQ ID NO:2. In one embodiment, the mRNA encoding a Cpf1 protein is encoded by a nucleic acid which is at least 50%, at least 60%, at least 75%, at least 80%, at least 85%, at least 90%, at least 95%, at least 97.5%, or at least 99% identical to SEQ ID NO:2.

In general, a guide RNA sequence is any polynucleotide sequence having sufficient complementarity with a target polynucleotide sequence to hybridize with the target sequence and direct sequence-specific binding of a CRISPR-Cpf1 complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. In some embodiments, the guide RNA comprises at least one chemically modified nucleotide.

Methods of Treatment

The chemically modified Cpf1 mRNA can be used to correct a mutation in a genome. For example, the guide RNAs can be designed to correct mutations that cause hemophilia (due to mutations in the genes encoding Factor VIII (F8; hemophilia A) or Factor IX (F9; hemoglobin B). In one aspect, the CRISPR-Cpf1 system, including the chemically modified Cpf1 mRNA, may be used to correct genetic mutations causing hemophilia.

In one aspect, disclosed herein is a method of treating hemophilia in a subject comprising:
introducing into a cell of the subject:
a) a guide RNA that hybridizes with a target sequence of a DNA molecule in a eukaryotic cell that contains the DNA molecule,
b) an mRNA encoding a Cpf1 protein, and
c) an isolated nucleic acid comprising a donor sequence comprising a nucleic acid encoding a truncated FVIII polypeptide;
wherein the cell of the subject contains a genetic mutation in the F8 gene;
wherein the mRNA encoding a Cpf1 protein comprises at least one chemically modified nucleotide,
wherein the guide RNA hybridizes with the target sequence,
wherein the target sequence is in the F8 gene,
wherein the Cpf1 protein creates a double stranded break in the DNA molecule,
wherein the nucleic acid encoding the truncated FVIII polypeptide is flanked by nucleic acid sequences homologous to the nucleic acid sequences upstream and downstream of the double stranded break in the DNA molecule, and
wherein the resultant repaired gene, upon expression, confers improved coagulation functionality to the encoded FVIII protein of the subject compared to the non-repaired F8 gene.

In one aspect, disclosed herein is a method of treating hemophilia in a subject comprising:
introducing into a cell of the subject:
a) a guide RNA that hybridizes with a target sequence of a DNA molecule in a eukaryotic cell that contains the DNA molecule,
b) a DNA vector comprising a DNA vector comprising a regulatory element operable in a eukaryotic cell operably linked to a nucleotide sequence encoding a Cpf1 protein, and
c) an isolated nucleic acid comprising a donor sequence comprising a nucleic acid encoding a truncated FVIII polypeptide;
wherein the guide RNA comprises at least one chemically modified nucleotide,
wherein the guide RNA hybridizes with the target sequence,
wherein the target sequence is in the F8 gene,
wherein the Cpf1 protein creates a double stranded break in the DNA molecule,
wherein the nucleic acid encoding the truncated FVIII polypeptide is flanked by nucleic acid sequences homologous to the nucleic acid sequences upstream and downstream of the double stranded break in the DNA, and wherein the resultant repaired gene, upon expression, confers improved coagulation functionality to the encoded FVIII protein of the subject compared to the non-repaired F8 gene.

In one aspect, disclosed herein is a method of treating hemophilia in a subject comprising:
introducing into a cell of the subject:
a) a guide RNA that hybridizes with a target sequence of a DNA molecule in a eukaryotic cell that contains the DNA molecule,
b) an mRNA encoding a Cpf1 protein, and
c) an isolated nucleic acid comprising a portion of the wild-type F9 gene;
wherein the cell of the subject contains a genetic mutation in the F9 gene;
wherein the mRNA encoding a Cpf1 protein comprises at least one chemically modified nucleotide,
wherein the guide RNA hybridizes with the target sequence,
wherein the target sequence is in the F9 gene,
wherein the Cpf1 protein creates a double stranded break in the DNA molecule,
wherein the nucleic acid encoding the nucleic acid encoding a wild-type portion of the F9 gene is flanked by nucleic acid sequences homologous to the nucleic acid sequences upstream and downstream of the double stranded break in the DNA molecule, and
wherein the resultant repaired gene, upon expression, confers improved coagulation functionality to the encoded FIX protein of the subject compared to the non-repaired F9 gene.

In additional embodiments, the CRISPR-Cpf1 system can be used to repair point mutations, truncations, deletions, inversions, or other genetic mutations that are identified as the causal mutation for a genetic disease.

Cpf1 Protein

In one embodiment, the Cpf1 protein is encoded by SEQ ID NO:1. This sequence can be codon optimized, can differ due to the degeneracy of the genetic code, can be similar, or share substantial identity, to SEQ ID NO:1, but still retain nuclease activity.

AsCpf1 sequence
(SEQ ID NO: 1)
ATGGCCCCAAAGAAGAAGCGGAAGGTCGGTATCCACGGAGTCCCAGC

AGCCACACAGTTCGAGGGCTTTACCAACCTGTATCAGGTGAGCAAGA

CACTGCGGTTTGAGCTGATCCCACAGGGCAAGACCCTGAAGCACATC

CAGGAGCAGGGCTTCATCGAGGAGGACAAGGCCCGCAATGATCACTA

CAAGGAGCTGAAGCCCATCATCGATCGGATCTACAAGACCTATGCCG

ACCAGTGCCTGCAGCTGGTGCAGCTGGATTGGGAGAACCTGAGCGCC

GCCATCGACTCCTATAGAAAGGAGAAAACCGAGGAGACAAGGAACGC

CCTGATCGAGGAGCAGGCCACATATCGCAATGCCATCCACGACTACT

TCATCGGCCGGACAGACAACCTGACCGATGCCATCAATAAGAGACAC

GCCGAGATCTACAAGGGCCTGTTCAAGGCCGAGCTGTTTAATGGCAA

GGTGCTGAAGCAGCTGGGCACCGTGACCACAACCGAGCACGAGAACG

CCCTGCTGCGGAGCTTCGACAAGTTTACAACCTACTTCTCCGGCTTT

TATGAGAACAGGAAGAACGTGTTCAGCGCCGAGGATATCAGCACAGC

CATCCCACACCGCATCGTGCAGGACAACTTCCCCAAGTTTAAGGAGA

ATTGTCACATCTTCACACGCCTGATCACCGCCGTGCCCAGCCTGCGG

GAGCACTTTGAGAACGTGAAGAAGGCCATCGGCATCTTCGTGAGCAC

CTCCATCGAGGAGGTGTTTTCCTTCCCTTTTTATAACCAGCTGCTGA

CACAGACCCAGATCGACCTGTATAACCAGCTGCTGGGAGGAATCTCT

CGGGAGGCAGGCACCGAGAAGATCAAGGGCCTGAACGAGGTGCTGAA

TCTGGCCATCCAGAAGAATGATGAGACAGCCCACATCATCGCCTCCC

TGCCACACAGATTCATCCCCCTGTTTAAGCAGATCCTGTCCGATAGG

AACACCCTGTCTTTCATCCTGGAGGAGTTTAAGAGCGACGAGGAAGT

GATCCAGTCCTTCTGCAAGTACAAGACACTGCTGAGAAACGAGAACG

TGCTGGAGACAGCCGAGGCCCTGTTTAACGAGCTGAACAGCATCGAC

CTGACACACATCTTCATCAGCCACAAGAAGCTGGAGACAATCAGCAG

CGCCCTGTGCGACCACTGGGATACACTGAGGAATGCCCTGTATGAGC

GGAGAATCTCCGAGCTGACAGGCAAGATCACCAAGTCTGCCAAGGAG

AAGGTGCAGCGCAGCCTGAAGCACGAGGATATCAACCTGCAGGAGAT

CATCTCTGCCGCAGGCAAGGAGCTGAGCGAGGCCTTCAAGCAGAAAA

CCAGCGAGATCCTGTCCCACGCACACGCCGCCCTGGATCAGCCACTG

CCTACAACCCTGAAGAAGCAGGAGGAGAAGGAGATCCTGAAGTCTCA

GCTGGACAGCCTGCTGGGCCTGTACCACCTGCTGGACTGGTTTGCCG

TGGATGAGTCCAACGAGGTGGACCCCGAGTTCTCTGCCCGGCTGACC

GGCATCAAGCTGGAGATGGAGCCTTCTCTGAGCTTCTACAACAAGGC

CAGAAATTATGCCACCAAGAAGCCCTACTCCGTGGAGAAGTTCAAGC

TGAACTTTCAGATGCCTACACTGGCCTCTGGCTGGGACGTGAATAAG

GAGAAGAACAATGGCGCCATCCTGTTTGTGAAGAACGGCCTGTACTA

TCTGGGCATCATGCCAAAGCAGAAGGGCAGGTATAAGGCCCTGAGCT

TCGAGCCCACAGAGAAAACCAGCGAGGGCTTTGATAAGATGTACTAT

GACTACTTCCCTGATGCCGCCAAGATGATCCCAAAGTGCAGCACCCA

GCTGAAGGCCGTGACAGCCCACTTTCAGACCCACACAACCCCCATCC

TGCTGTCCAACAATTTCATCGAGCCTCTGGAGATCACAAAGGAGATC

TACGACCTGAACAATCCTGAGAAGGAGCCAAAGAAGTTTCAGACAGC

CTACGCCAAGAAAACCGGCGACCAGAAGGGCTACAGAGAGGCCCTGT

GCAAGTGGATCGACTTCACAAGGGATTTTCTGTCCAAGTATACCAAG

ACAACCTCTATCGATCTGTCTAGCCTGCGCCATCCTCTCAGTATAA

GGACCTGGGCGAGTACTATGCCGAGCTGAATCCCCTGCTGTACCACA

TCAGCTTCCAGAGAATCGCCGAGAAGGAGATCATGGATGCCGTGGAG

ACAGGCAAGCTGTACCTGTTCCAGATCTATAACAAGGACTTTGCCAA

GGGCCACCACGGCAAGCCTAATCTGCACACACTGTATTGGACCGGCC

TGTTTTCTCCAGAGAACCTGGCCAAGACAAGCATCAAGCTGAATGGC

CAGGCCGAGCTGTTCTACCGCCCTAAGTCCAGGATGAAGAGGATGGC

ACACCGGCTGGGAGAGAAGATGCTGAACAAGAAGCTGAAGGATCAGA

AAACCCCAATCCCCGACACCCTGTACCAGGAGCTGTACGACTATGTG

AATCACAGACTGTCCCACGACCTGTCTGATGAGGCCAGGGCCCTGCT
GCCCAACGTGATCACCAAGGAGGTGTCTCACGAGATCATCAAGGATA
GGCGCTTTACCAGCGACAAGTTCTTTTTCCACGTGCCTATCACACTG
AACTATCAGGCCGCCAATTCCCCATCTAAGTTCAACCAGAGGGTGAA
TGCCTACCTGAAGGAGCACCCCGAGACACCTATCATCGGCATCGATC
GGGGCGAGAGAAACCTGATCTATATCACAGTGATCGACTCCACCGGC
AAGATCCTGGAGCAGCGGAGCCTGAACACCATCCAGCAGTTTGATTA
CCAGAAGAAGCTGGACAACAGGGAGAAGGAGAGGGTGGCAGCAAGGC
AGGCCTGGTCTGTGGTGGGCACAATCAAGGATCTGAAGCAGGGCTAT
CTGAGCCAGGTCATCCACGAGATCGTGGACCTGATGATCCACTACCA
GGCCGTGGTGGTGCTGGAGAACCTGAATTTCGGCTTTAAGAGCAAGA
GGACCGGCATCGCCGAGAAGGCCGTGTACCAGCAGTTCGAGAAGATG
CTGATCGATAAGCTGAATTGCCTGGTGCTGAAGGACTATCCAGCAGA
GAAAGTGGGAGGCGTGCTGAACCCATACCAGCTGACAGACCAGTTCA
CCTCCTTTGCCAAGATGGGCACCCAGTCTGGCTTCCTGTTTTACGTG
CCTGCCCCATATACATCTAAGATCGATCCCCTGACCGGCTTCGTGGA
CCCCTTCGTGTGGAAAACCATCAAGAATCACGAGAGCCGCAAGCACT
TCCTGGAGGGCTTCGACTTTCTGCACTACGACGTGAAAACCGGCGAC
TTCATCCTGCACTTTAAGATGAACAGAAATCTGTCCTTCCAGAGGGG
CCTGCCCGGCTTTATGCCTGCATGGGATATCGTGTTCGAGAAGAACG
AGACACAGTTTGACGCCAAGGGCACCCCTTTCATCGCCGGCAAGAGA
ATCGTGCCAGTGATCGAGAATCACAGATTCACCGGCAGATACCGGGA
CCTGTATCCTGCCAACGAGCTGATCGCCCTGCTGGAGGAGAAGGGCA
TCGTGTTCAGGGATGGCTCCAACATCCTGCCAAAGCTGCTGGAGAAT
GACGATTCTCACGCCATCGACACCATGGTGGCCCTGATCCGCAGCGT
GCTGCAGATGCGGAACTCCAATGCCGCCACAGGCGAGGACTATATCA
ACAGCCCCGTGCGCGATCTGAATGGCGTGTGCTTCGACTCCCGGTTT
CAGAACCCAGAGTGGCCCATGGACGCCGATGCCAATGGCGCCTACCA
CATCGCCCTGAAGGGCCAGCTGCTGCTGAATCACCTGAAGGAGAGCA
AGGATCTGAAGCTGCAGAACGGCATCTCCAATCAGGACTGGCTGGCC
TACATCCAGGAGCTGCGCAACAAGCGTCCTGCTGCTACTAAGAAAGC
TGGTCAAGCTAAGAAAAAGAAATAA.

In one embodiment, the Cpf1 protein is encoded by SEQ ID NO:2. This sequence can be codon optimized, can differ due to the degeneracy of the genetic code, can be similar, or share substantial identity, to SEQ ID NO:2, but still retain nuclease activity.

LbCpf1 sequence
(SEQ ID NO: 2)
ATGGCCCCAAAGAAGAAGCGGAAGGTCGGTATCCACGGAGTCCCAGC

AGCCAGCAAGCTGGAGAAGTTTACAAACTGCTACTCCCTGTCTAAGA

CCCTGAGGTTCAAGGCCATCCCTGTGGGCAAGACCCAGGAGAACATC

GACAATAAGCGGCTGCTGGTGGAGGACGAGAAGAGAGCCGAGGATTA

TAAGGGCGTGAAGAAGCTGCTGGATCGCTACTATCTGTCTTTTATCA

ACGACGTGCTGCACAGCATCAAGCTGAAGAATCTGAACAATTACATC

AGCCTGTTCCGGAAGAAAACCAGAACCGAGAAGGAGAATAAGGAGCT

GGAGAACCTGGAGATCAATCTGCGGAAGGAGATCGCCAAGGCCTTCA

AGGGCAACGAGGGCTACAAGTCCCTGTTTAAGAAGGATATCATCGAG

ACAATCCTGCCAGAGTTCCTGGACGATAAGGACGAGATCGCCCTGGT

GAACAGCTTCAATGGCTTTACCACAGCCTTCACCGGCTTCTTTGATA

ACAGAGAGAATATGTTTTCCGAGGAGGCCAAGAGCACATCCATCGCC

TTCAGGTGTATCAACGAGAATCTGACCCGCTACATCTCTAATATGGA

CATCTTCGAGAAGGTGGACGCCATCTTTGATAAGCACGAGGTGCAGG

AGATCAAGGAGAAGATCCTGAACAGCGACTATGATGTGGAGGATTTC

TTTGAGGGCGAGTTCTTTAACTTTGTGCTGACACAGGAGGGCATCGA

CGTGTATAACGCCATCATCGGCGGCTTCGTGACCGAGAGCGGCGAGA

AGATCAAGGGCCTGAACGAGTACATCAACCTGTATAATCAGAAAACC

AAGCAGAAGCTGCCTAAGTTTAAGCCACTGTATAAGCAGGTGCTGAG

CGATCGGGAGTCTCTGAGCTTCTACGGCGAGGGCTATACATCCGATG

AGGAGGTGCTGGAGGTGTTTAGAAACACCCTGAACAAGAACAGCGAG

ATCTTCAGCTCCATCAAGAAGCTGGAGAAGCTGTTCAAGAATTTTGA

CGAGTACTCTAGCGCCGGCATCTTTGTGAAGAACGGCCCCGCCATCA

GCACAATCTCCAAGGATATCTTCGGCGAGTGGAACGTGATCCGGGAC

AAGTGGAATGCCGAGTATGACGATATCCACCTGAAGAAGAAGGCCGT

GGTGACCGAGAAGTACGAGGACGATCGGAGAAAGTCCTTCAAGAAGA

TCGGCTCCTTTTCTCTGGAGCAGCTGCAGGAGTACGCCGACGCCGAT

CTGTCTGTGGTGGAGAAGCTGAAGGAGATCATCATCCAGAAGGTGGA

TGAGATCTACAAGGTGTATGGCTCCTCTGAGAAGCTGTTCGACGCCG

ATTTTGTGCTGGAGAAGAGCCTGAAGAAGAACGACGCCGTGGTGGCC

ATCATGAAGGACCTGCTGGATTCTGTGAAGAGCTTCGAGAATTACAT

CAAGGCCTTCTTTGGCGAGGGCAAGGAGACAAACAGGGACGAGTCCT

TCTATGGCGATTTTGTGCTGGCCTACGACATCCTGCTGAAGGTGGAC

CACATCTACGATGCCATCCGCAATTATGTGACCCAGAAGCCCTACTC

TAAGGATAAGTTCAAGCTGTATTTTCAGAACCCTCAGTTCATGGGCG

GCTGGGACAAGGATAAGGAGACAGACTATCGGGCCACCATCCTGAGA

TACGGCTCCAAGTACTATCTGGCCATCATGGATAAGAAGTACGCCAA

GTGCCTGCAGAAGATCGACAAGGACGATGTGAACGGCAATTACGAGA

AGATCAACTATAAGCTGCTGCCCGGCCCTAATAAGATGCTGCCAAAG

GTGTTCTTTTCTAAGAAGTGGATGGCCTACTATAACCCCAGCGAGGA

CATCCAGAAGATCTACAAGAATGGCACATTCAAGAAGGGCGATATGT

TTAACCTGAATGACTGTCACAAGCTGATCGACTTCTTTAAGGATAGC

ATCTCCCGGTATCCAAAGTGGTCCAATGCCTACGATTTCAACTTTTC

-continued

```
TGAGACAGAGAAGTATAAGGACATCGCCGGCTTTTACAGAGAGGTGG

AGGAGCAGGGCTATAAGGTGAGCTTCGAGTCTGCCAGCAAGAAGGAG

GTGGATAAGCTGGTGGAGGAGGGCAAGCTGTATATGTTCCAGATCTA

TAACAAGGACTTTTCCGATAAGTCTCACGGCACACCCAATCTGCACA

CCATGTACTTCAAGCTGCTGTTTGACGAGAACAATCACGGACAGATC

AGGCTGAGCGGAGGAGCAGAGCTGTTCATGAGGCGCGCCTCCCTGAA

GAAGGAGGAGCTGGTGGTGCACCCAGCCAACTCCCCTATCGCCAACA

AGAATCCAGATAATCCCAAGAAAACCACAACCCTGTCCTACGACGTG

TATAAGGATAAGAGGTTTTCTGAGGACCAGTACGAGCTGCACATCCC

AATCGCCATCAATAAGTGCCCCAAGAACATCTTCAAGATCAATACAG

AGGTGCGCGTGCTGCTGAAGCACGACGATAACCCCTATGTGATCGGC

ATCGATAGGGGCGAGCGCAATCTGCTGTATATCGTGGTGGTGGACGG

CAAGGGCAACATCGTGGAGCAGTATTCCCTGAACGAGATCATCAACA

ACTTCAACGGCATCAGGATCAAGACAGATTACCACTCTCTGCTGGAC

AAGAAGGAGAAGGAGAGGTTCGAGGCCCGCCAGAACTGGACCTCCAT

CGAGAATATCAAGGAGCTGAAGGCCGGCTATATCTCTCAGGTGGTGC

ACAAGATCTGCGAGCTGGTGGAGAAGTACGATGCCGTGATCGCCCTG

GAGGACCTGAACTCTGGCTTTAAGAATAGCCGCGTGAAGGTGGAGAA

GCAGGTGTATCAGAAGTTCGAGAAGATGCTGATCGATAAGCTGAACT

ACATGGTGGACAAGAAGTCTAATCCTTGTGCAACAGGCGGCGCCCTG

AAGGGCTATCAGATCACCAATAAGTTCGAGAGCTTTAAGTCCATGTC

TACCCAGAACGGCTTCATCTTTTACATCCCTGCCTGGCTGACATCCA

AGATCGATCCATCTACCGGCTTTGTGAACCTGCTGAAAACCAAGTAT

ACCAGCATCGCCGATTCCAAGAAGTTCATCAGCTCCTTTGACAGGAT

CATGTACGTGCCCGAGGAGGATCTGTTCGAGTTTGCCCTGGACTATA

AGAACTTCTCTCGCACAGACGCCGATTACATCAAGAAGTGGAAGCTG

TACTCCTACGGCAACCGGATCAGAATCTTCCGGAATCCTAAGAAGAA

CAACGTGTTCGACTGGGAGGAGGTGTGCCTGACCAGCGCCTATAAGG

AGCTGTTCAACAAGTACGGCATCAATTATCAGCAGGGCGATATCAGA

GCCCTGCTGTGCGAGCAGTCCGACAAGGCCTTCTACTCTAGCTTTAT

GGCCCTGATGAGCCTGATGCTGCAGATGCGGAACAGCATCACAGGCC

GCACCGACGTGGATTTTCTGATCAGCCCTGTGAAGAACTCCGACGGC

ATCTTCTACGATAGCCGGAACTATGAGGCCCAGGAGAATGCCATCCT

GCCAAAGAACGCCGACGCCAATGGCGCCTATAACATCGCCAGAAAGG

TGCTGTGGGCCATCGGCCAGTTCAAGAAGGCCGAGGACGAGAAGCTG

GATAAGGTGAAGATCGCCATCTCTAACAAGGAGTGGCTGGAGTACGC

CCAGACCAGCGTGAAGCACAAGCGTCCTGCTGCTACTAAGAAAGCTG

GTCAAGCTAAGAAAAAGAAATAA.
```

EXAMPLES

The following examples are set forth below to illustrate the systems, methods, compositions and results according to the disclosed subject matter. These examples are not intended to be inclusive of all aspects of the subject matter disclosed herein, but rather to illustrate representative systems, methods, compositions and results. These examples are not intended to exclude equivalents and variations of the present invention which are apparent to one skilled in the art.

Example 1. Chemical Modification of Cpf1 mRNA

Synthesis of Chemically Modified Cpf1 mRNA.

Figure 3A:
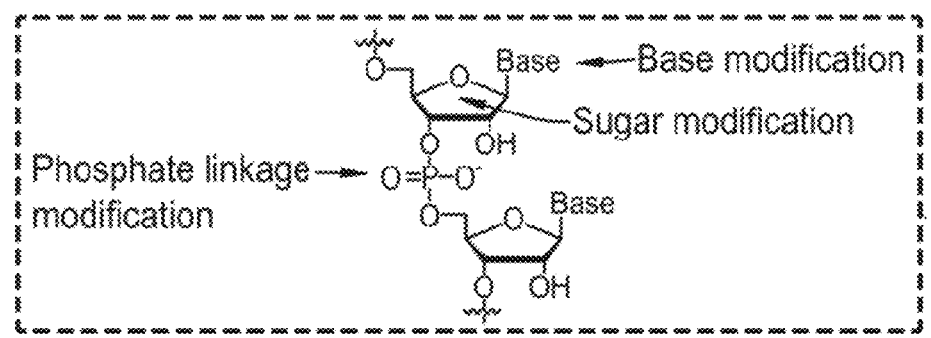
FIGS. 3A-3D. A panel of chemically modified nucleotides utilized for Cpf1 mRNAs.
Figure 3B:
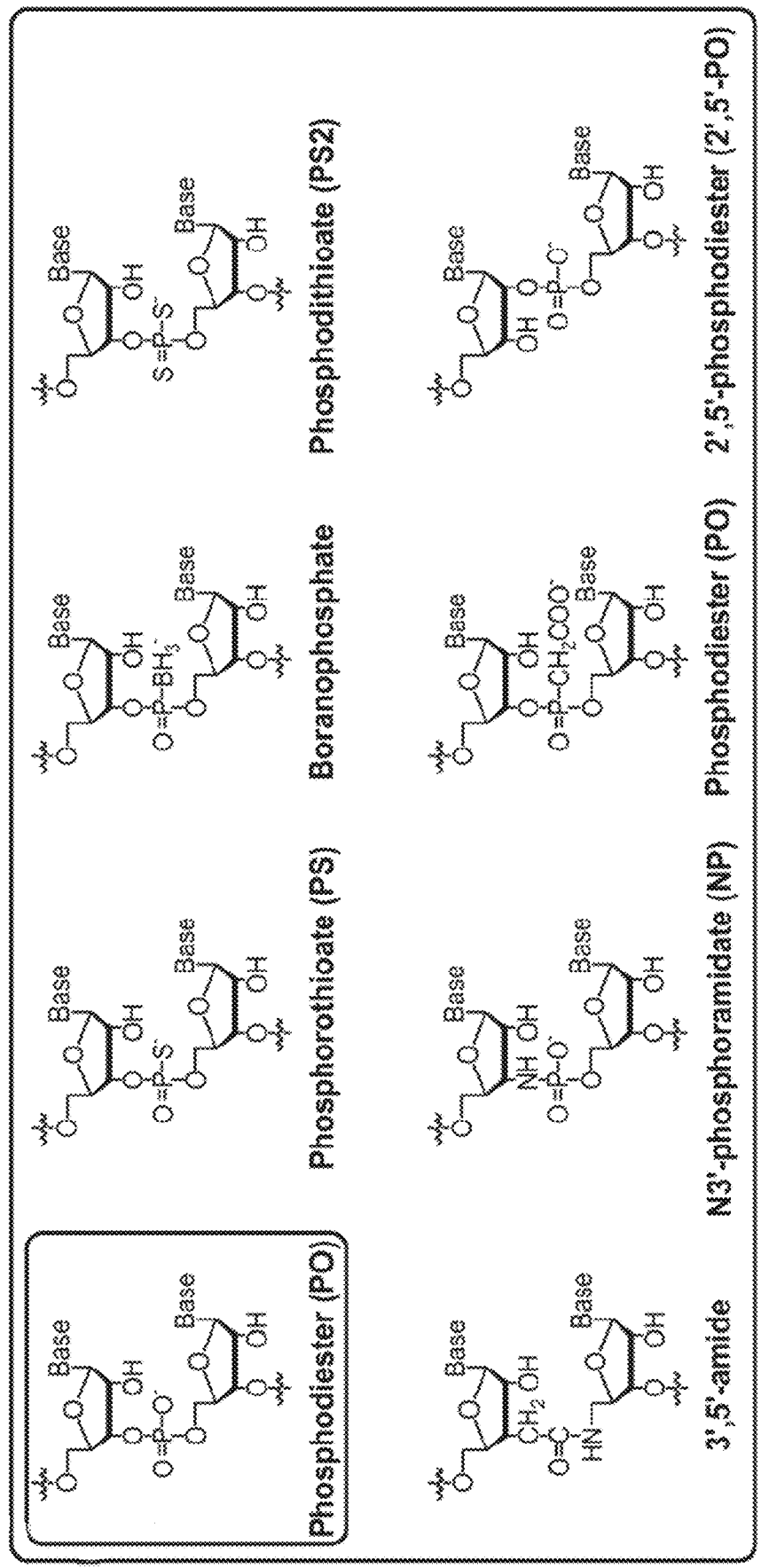
Figure 3C:
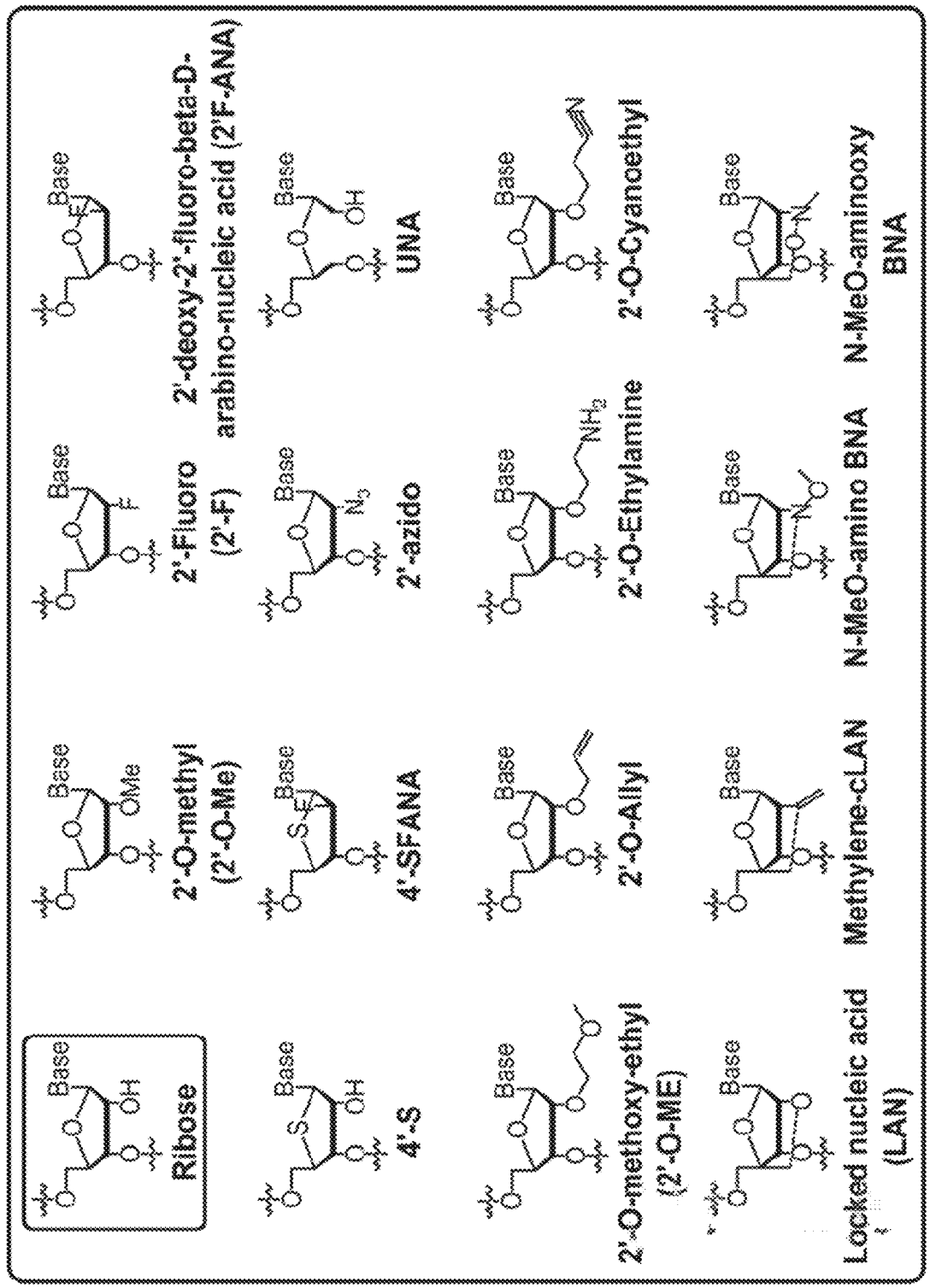
Figure 3D:
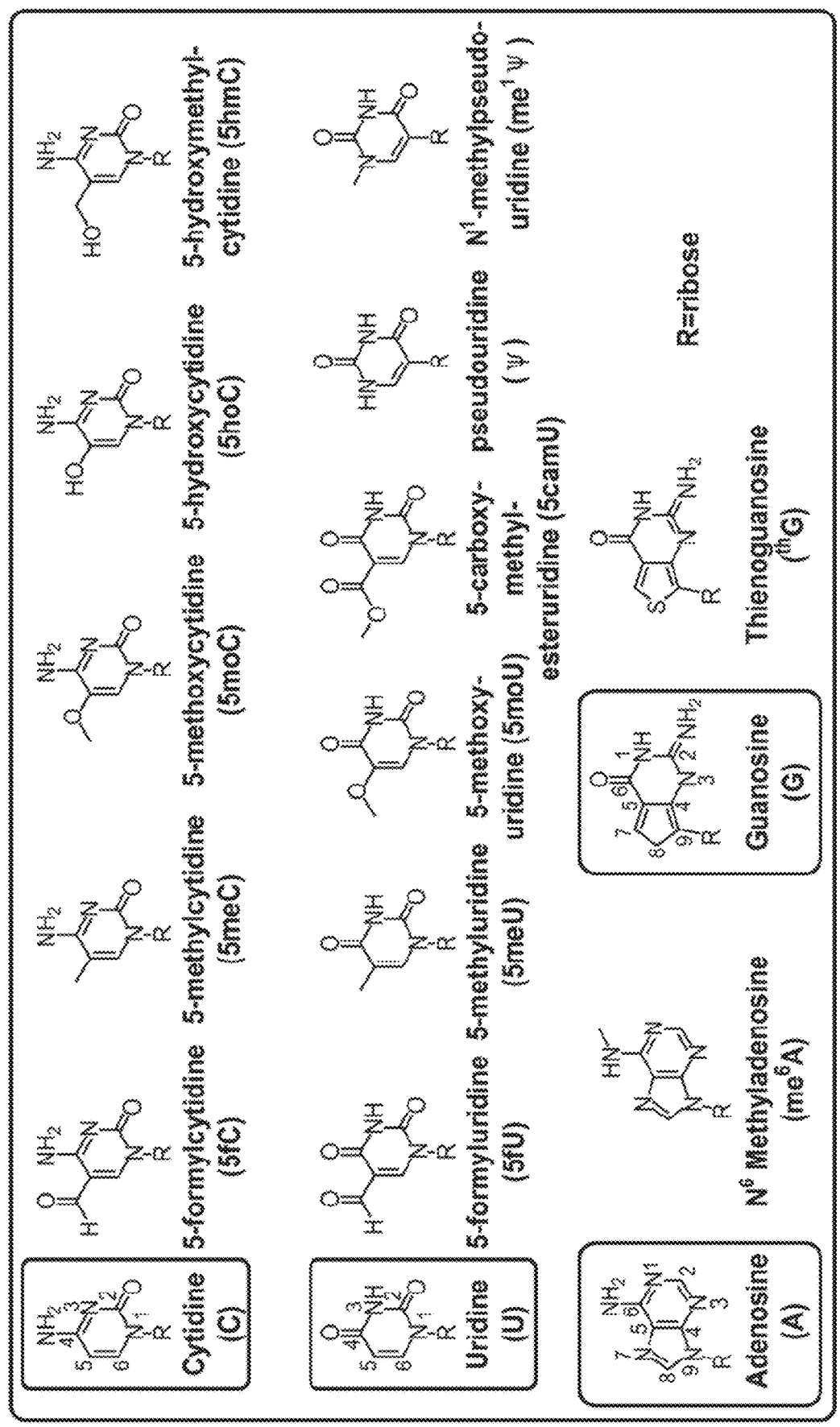
Figure 4:
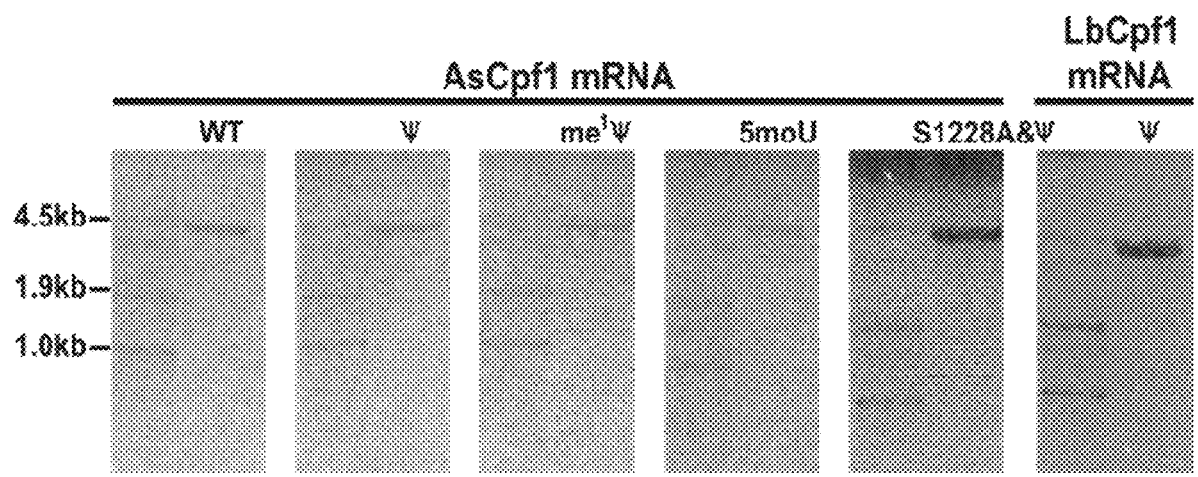
FIG. 4. Polyacrylamide gel electrophoresis (PAGE) analysis of modified AsCpf1 mRNAs. Polyacrylamide gel electrophoresis (PAGE) analysis of WT, ψ, m$^1$ψ and 5moU-modified AsCpf1 mRNAs as well as y modified LbCpf1 mRNA.

Chemically modified mRNAs encoding AsCpf1 (*Acidaminococcus* sp. BV3L6 CRISPR from *Prevotella* and *Francisella* 1) protein including but not limited to PS backbone modification, ψ, 5moU, me$^1$ψ, 5hmC, 5meU, 5meC and 5moC base modification, 2'-O-Me, 2'-F sugar modification, as well as their combinations (FIG. 2) are synthesized using a commercially available in vitro transcription kit. All mRNA were verified by polyacrylamide gel electrophoresis (PAGE) (FIG. 4). These Cpf1 mRNAs contained a complete replacement of the wild-type uridine nucleotides with either ψ, 5moU, or me$^1$ψ (FIG. 3).

Co-Delivery of AsCpf1 mRNA & Guide RNA (gRNA) and Extraction of Genomic DNA 293T cells were seeded on a 24-well plate at a density of 100,000 cells per well. After overnight culture, cells were treated with chemically modified AsCpf1 mRNA expressing AsCpf1 protein (500 or 1000 ng) and gRNA (15 or 30 pmol, PAGE-grade) using LipofectamineMAX, Lipofectamine 3000 or mRNA-in reagent. 48 hr after treatment, genomic DNA (gDNA) from 293T cells was extracted using the DNeasy Blood & Tissue Kit (QIAGEN) following the manufacturer's instructions, and quantified by Nanodrop 2000. Unmodified AsCpf1 mRNA served as a control.

T7E1 Assay

On-target or off-target sites were amplified using Q5 High-Fidelity DNA Polymerase (New England Biolabs) and specific primers (Integrated DNA Technologies, Supplementary). The PCR products (10 μL) were then hybridized in NEBuffer 2 (New England Biolabs) in a T100 thermal cycler (Bio-Rad). Subsequently, the annealed PCR products were subjected to T7 Endonuclease I (New England Biolabs) digestion, and analysis on a 2% agarose gel to determine the efficiency of genome editing (indel %) with the following formula: $100 \times (1-(1-\text{fraction cleaved})^{1/2})$.

Cpf1 Protein

In one embodiment, the Cpf1 protein is encoded by SEQ ID NO:1. This sequence can be codon optimized, can differ due to the degeneracy of the genetic code, can be similar, or share substantial identity, to SEQ ID NO:1, but still retain nuclease activity.

In one embodiment, the Cpf1 protein is encoded by SEQ ID NO:2. This sequence can be codon optimized, can differ due to the degeneracy of the genetic code, can be similar, or share substantial identity, to SEQ ID NO:2, but still retain nuclease activity.

In one embodiment, all of the uridines (corresponding to the thymidines (T) in the DNA sequence) in the Cpf1 mRNA have been replaced by pseudouridine (See FIG. 3). In one embodiment, all of the uridines (corresponding to the thymidines (T) in the DNA sequence) in the Cpf1 mRNA have been replaced by N$_1$-methylpseudouridine (me$^1$ψ) (See FIG. 3). In one embodiment, all of the uridines (corresponding to the thymidines (T) in the DNA sequence) in the Cpf1 mRNA have been replaced by 5-methoxyuridine (5moU) (See FIG. 3).

Synthesis of DNMT1 guide RNA (gRNA).

Guide RNAs (gRNAs) targeting human DNMT1 locus were synthesized using automated solid-phase DNA/RNA synthesizer. The sequence of unmodified gRNA for CRISPR-AsCpf1 is (gWT)
(SEQ ID NO: 3)
5'-UAAUUUCUACUCUUGUAGAUCUGAUGGUCCAUGUCUGUUACUC-3'.

Example 2. Effects of Chemically Modified Messenger RNA on Protein Expression Messenger RNAs (mRNAs) encoding functional proteins have demonstrated their therapeutic potential in fundamental and clinical studies (Sahin, U., et. al. (2014) *Nat. Rev. Drug Discov.* 13, 759-780; Islam, M. A., et. al. (2015) *Biomater. Sci.* 3, 1519-1533; McIvor, R. S. (2011) *Mol. Ther.* 19, 822-823; Pascolo, S. (2008) *Handb. Exp. Pharmacol.* 221-235; Tavernier, G., et. al. (2011) *J. Control Release* 150, 238-247)). For example, immunotherapy with mRNA-electroporated dendritic cell provided therapeutic benefit in several cancer clinical trials (Pascolo, S. (2008) *Handb. Exp. Pharmacol.* 221-235; Anguille, S., et. al. (2014) *Lancet Oncol.* 15, e257-267)). mRNAs were also utilized to produce chimeric antigen receptors in T cells for adoptive T-cell therapy, (Zhao, Y., et. al. (2010) *Cancer Res.* 70, 9053-9061)) to express functional proteins for protein replacement therapy, (Li, B., et. al. (2015) *Nano Lett.* 15, 8099-8107; Kauffman, et. al. (2015) *Nano Lett.* 15, 7300-7306; Zangi, L., et. al. (2013) *Nat. Biotechnol.* 31, 898-907; Kormann, M. S., et. al. (2011) *Nat. Biotechnol.* 29, 154-157; Thess, A., et. al. (2015) *Mol. Ther.* 23, 1456-1464)) and most recently, to make nucleases for gene engineering (Hendel, A., et. al. (2015) *Nat. Biotechnol.* 33, 985-989; Wang, J., et. al. (2015) *Nat. Biotechnol.* 33, 1256-1263)). Although there have been significant advances in mRNA-based therapeutics in the past decade, instability and immunogenicity of mRNA hinders its therapeutic application in humans (Sahin, U., et. al. (2014) *Nat. Rev. Drug Discov.* 13, 759-780; Pascolo, S. (2008) *Handb. Exp. Pharmacol.* 221-235; Tavernier, G., et. al. (2011) *J. Control Release* 150, 238-247; Weissman, D., and Kariko, K. (2015) *Mol. Ther.* 23, 1416-1417; Kariko, K., et. al. (2004) *J. Biol. Chem.* 279, 12542-12550)).

Figure 2:
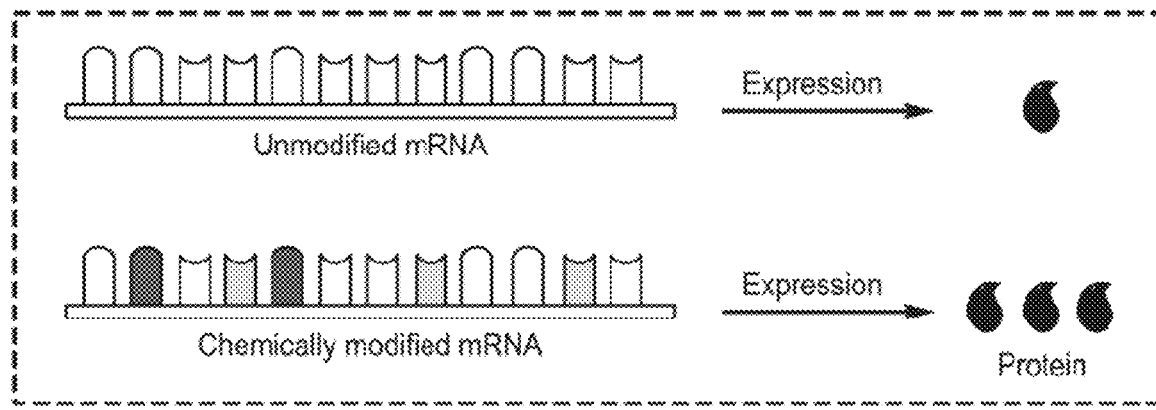
FIG. 2. Illustration showing chemically modified mRNAs improve protein expression.

In order to address these issues, numerous strategies for mRNA modification can be investigated to improve translation efficiency and reduce immunogenicity, including modifications at the 5' cap, 5' and 3'-untranslated regions, the coding region, and the poly(A) tail (Sahin, U., et. al. (2014) *Nat. Rev. Drug Discov.* 13, 759-780). Incorporation of chemically modified nucleotides into mRNAs (FIG. 2) has also been reported in the literature (Sahin, U., et. al. (2014) *Nat. Rev. Drug Discov.* 13, 759-780). For instance, Karikó et al. showed that pseudouridine (ψ) modified mRNA increased expression of encoded erythropoietin (Kariko, K., et. al. (2012) *Mol. Ther.* 20, 948-953; Kariko, K., et. al. (2008) *Mol. Ther.* 16, 1833-1840). Kormann et al. reported that combination of 2-thiouridine (s2U) and 5-methylcytidine (5meC) in modified mRNAs extended expression of encoded protein to four weeks (Kormann, M. S., et. al. (2011) *Nat. Biotechnol.* 29, 154-157). Recently, Zangi et al. achieved induction of vascular regeneration using modified (5meC and ψ) mRNA encoding human vascular endothelial growth factor-A (Zangi, L., et. al. (2013) *Nat. Biotechnol.* 31, 898-907). Uchida et al. stated that combination of 5meC and ψ in mRNAs augmented protein expression (Uchida, S., et. al. (2015) *Pharmaceutics* 7, 137-151). Most recently, Andries et al. reported that $N_1$-methylpseudouridine ($me^1\psi$) modified mRNA enhanced luciferase expression and reduced immunogenicity (Andries, O., et. al. (2015) *J. Control Release* 217, 337-344). These studies demonstrate the importance of chemically modified nucleotides on mRNA structure and function. However, knowledge of the structure-activity relationship on chemically modified mRNAs remains limited. Disclosed herein is the synthesis and evaluation of a library of chemically modified mRNAs. A correlation analysis for protein expression of mRNAs at various conditions including translation temperature, cell types, and coding sequences was performed (FIG. 2). From these experiments, $me^1\psi$, 5-methoxyuridine (5moU) and ψ were shown to have the largest increases in improving protein expression.

Figure 5A:
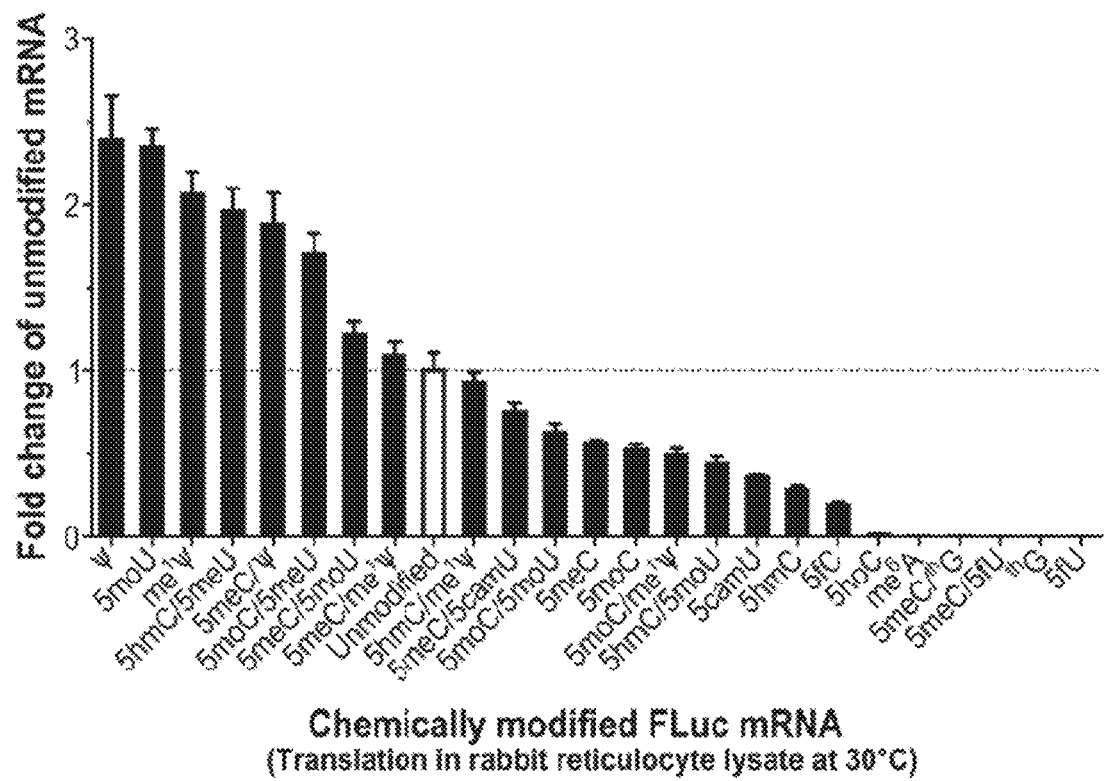
FIGS. 5A-5B. FLuc expression of chemically modified FLuc mRNAs in a rabbit reticulocyte lysate system.

In order to investigate the effects of chemical modifications on mRNAs, a library of 24 firefly Luciferase mRNAs (FLuc mRNAs) using chemically modified nucleotides was synthesized (See FIG. 3). Single modifications and combinations of modifications were incorporated. Next, FLuc expression of mRNAs was evaluated in a rabbit reticulocyte lysate system at 30° C. according to the manufacturer's protocol. As shown in FIG. 5a, eight of twenty four FLuc mRNAs showed higher luciferase intensity compared to unmodified FLuc mRNA (three single modifications: ψ, 5moU, $me^1\psi$; and five combination modifications: 5hmC/5meU, 5meC/ψ, 5moC/5meU, 5meC/5moU, and 5meC/$me^1\psi$). Among them, ψ-modified FLuc mRNA displayed the highest increase of translation efficiency.

Figure 5B:
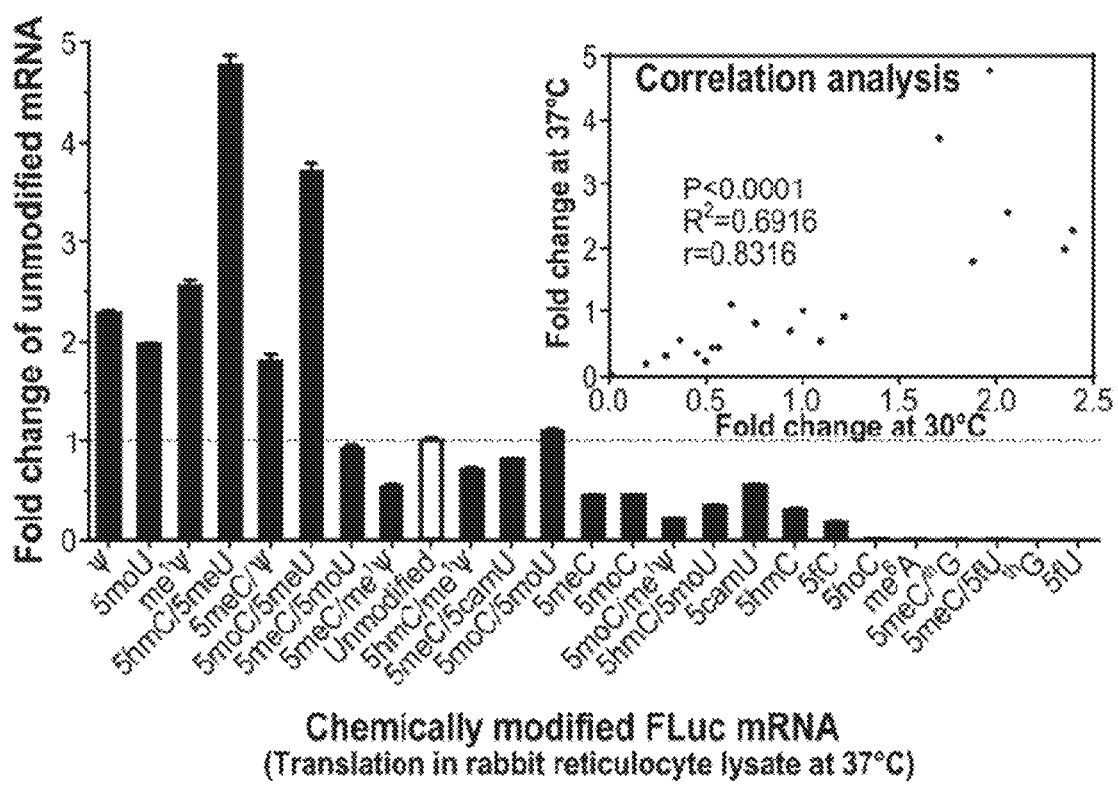

Next, the effects of temperature on mRNA translation was analyzed by conducting the experiment at 37° C. Analysis of the results indicated significant correlation for translation at 30 and 37° C. ($p<0.0001$; $R2=0.69$; Pearson correlation coefficient $r=0.8316$, FIG. 5b), but rank order of the top modified mRNAs showed dramatic changes. For instance, FLuc expression of 5hmC/5meU-modified mRNA was over 2-fold higher than that of ψ-modified mRNA at 37° C. compared to that at 30° C. (FIG. 5). These results suggested that temperature did not affect the overall trend for a set of modified mRNAs, while it did have an important impact on individual mRNAs. Consequently, the top six modified mRNAs (ψ, 5moU, $me^1\psi$, 5hmC/5meU, 5meC/ψ and 5moC/5meU) in both experiments were selected for further studies.

Figure 6:
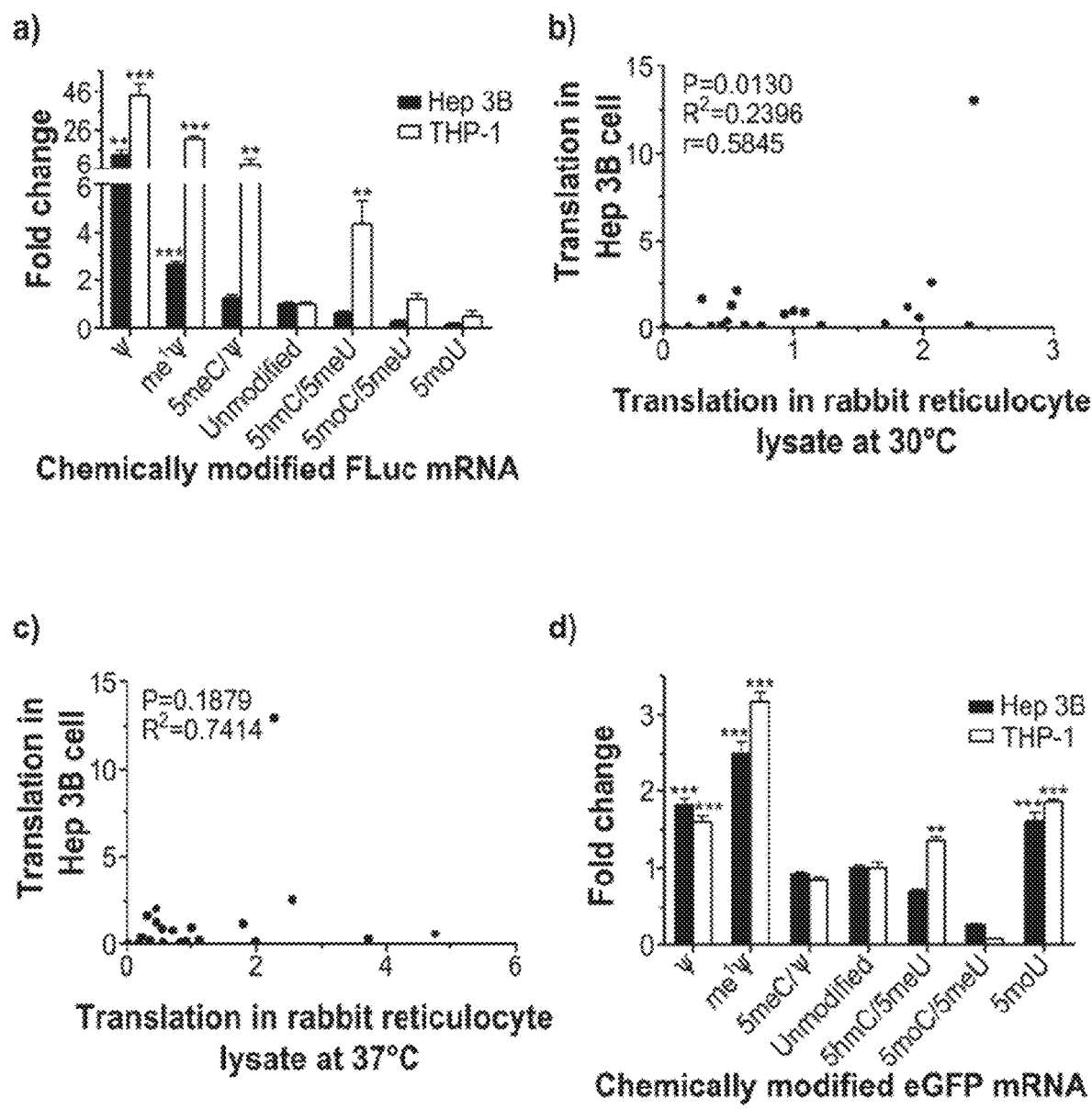
FIG. 6. (a) Relative FLuc expression of chemically modified FLuc mRNAs in Hep 3B and THP-1 cells (normalized by unmodified FLuc mRNA). Five types of modified FLuc mRNAs (ψ, me$^1$ψ, 5meC/ψ, 5hmC/5meU, and 5moC/5meU-FLuc mRNAs) showed superior activity to unmodified FLuc mRNA. , p<0.01; *, p<0.001. (b) Significant correlation of luciferase intensity in the rabbit reticulocyte lysate system at 30° C. and in Hep 3B cells was observed (p=0.013; $R^2$=0.2396; r=0.5845). (c) No significant correlation was found for luciferase intensity in the rabbit reticulocyte lysate system at 37° C. and in Hep 3B cells. (d) Relative eGFP expression of chemically modified eGFP mRNAs in Hep 3B and THP-1 cells (normalized by unmodified eGFP mRNA). me$^1$ψ, 5moU and ψ-modified eGFP mRNA displayed higher eGFP expression compared to other chemically modified eGFP mRNAs. , p<0.01; *, p<0.001.
Figure 8:
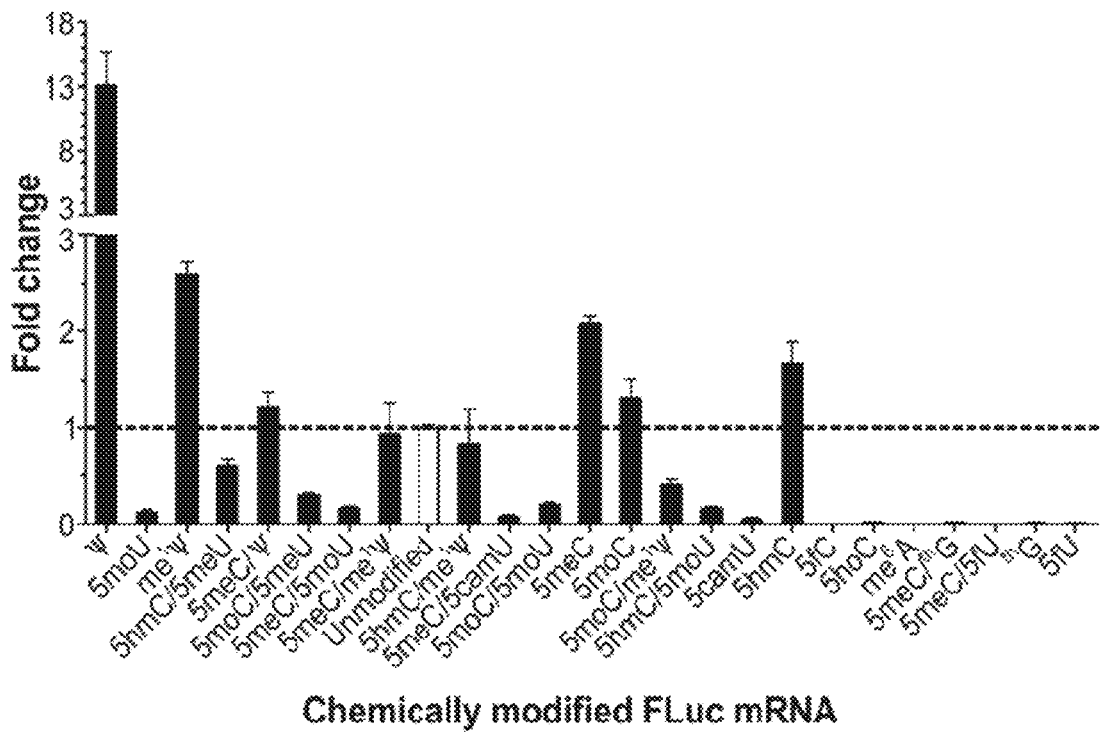
FIG. 8. Relative FLuc expression of 24 chemically modified FLuc mRNAs in Hep 3B cells (normalized by unmodified FLuc mRNA).

In order to study protein expression in cells, FLuc mRNAs were transfected in Hep 3B cells (a hepatocellular carcinoma cell line). As shown in FIG. 6a, ψ and $me^1\psi$-modified FLuc mRNAs were favorable modifications in Hep 3B cells compared to unmodified and other modified FLuc mRNAs. To explore mRNA translation in a different cell line, similar experiments were conducted in THP-1 cells (an acute monocytic leukemia cell line). Interestingly, five types of modified FLuc mRNAs (ψ, $me^1\psi$, 5meC/ψ, 5hmC/5meU, and 5moC/5meU-FLuc mRNAs) showed superior activity to unmodified FLuc mRNA. In particular, 5hmC/5meU-FLuc mRNA was over four-fold better than unmodified FLuc mRNA in THP-1 cells, while it was less efficient than unmodified FLuc mRNA in Hep 3B cells (FIG. 6a). These results indicate that mRNAs translation was dependent on cell types to a certain extent. In this study, ψ-modified FLuc mRNA was the most potent in both Hep 3B and THP-1 cells (over 10 and 40-fold higher than unmodified FLuc mRNA, respectively). In order to explore the correlation between the cell-free rabbit reticulocyte lysate system and mRNA translation in cells, luciferase intensity was quantified for the whole library of modified FLuc mRNAs in Hep 3B cells (FIG. 8). A significant correlation was observed for luciferase intensity in the rabbit reticulocyte lysate system at 30° C. and in Hep 3B cells. However, no significant correlation was found for luciferase intensity in the rabbit reticulocyte lysate system at 37° C. and in Hep 3B cells (FIGS. 6b and 6c).

In order to examine the effects of chemical modification on mRNAs with a different coding sequence, a library of 24 mRNAs encoding enhanced green fluorescent protein (eGFP mRNAs) with the same chemical modifications as FLuc mRNAs was prepared by in vitro transcription as mentioned above. Next, Hep 3B and THP-1 cells were transfected with modified eGFP mRNAs using the unmodified eGFP mRNA as a control. As shown in FIG. 6d, ψ, me$^1$ψ and 5moU-modified eGFP mRNAs were the preferred modifications in Hep 3B cells. Consistent with previous observation, 5hmC/5meU-modified eGFP mRNA was also more favorable in THP-1 cells compared to that in Hep 3B cells. The results further indicated that effects of chemically modified mRNAs may depend on cell types. In addition, 5moU-modified eGFP mRNA showed much higher translation when encoding eGFP in comparison to encoding FLuc. More importantly, lead eGFP mRNAs were identified consisting of full substitution of me$^1$ψ-, 5moU-, and ψ-modified nucleotides, protein expression of which ranked in the top three in cells lines tested. In order to further explore the effects in primary cells, similar experiments were conducted in primary rat hepatocytes. Consistently, me$^1$ψ-, 5moU-, and ψ-modified eGFP mRNAs were more potent than unmodified eGFP mRNA. These results indicated that coding sequences of mRNA are capable of affecting the protein expression of chemically modified mRNAs.

Figure 7:
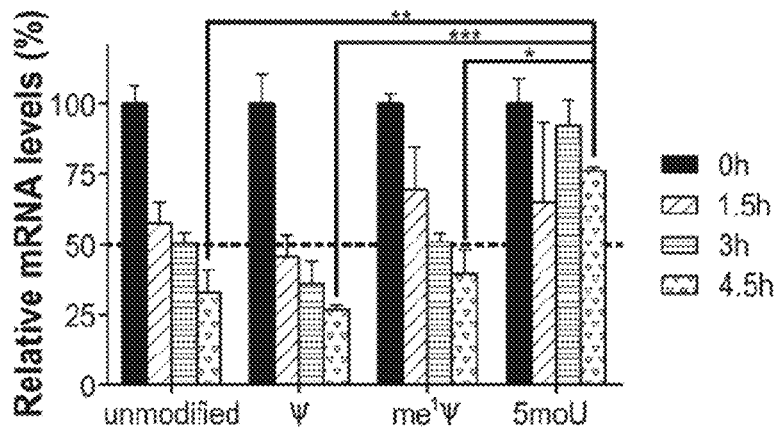
FIG. 7. Relative mRNA levels at different time intervals (t=0, 1.5, 3, and 4.5 h). The initial level of unmodified and modified mRNAs was normalized by 18S rRNA using RT-qPCR quantification. 5moU modifications significantly increased stability of eGFP mRNA. *, p<0.05; , p<0.01; *, p<0.001.

To study the stability of chemically modified mRNAs, Hep 3B cells were transfected with unmodified, me$^1$ψ-, 5moU-, or ψ-modified eGFP mRNAs. After 1 h treatment (t=0), total RNA was collected at different time intervals (t=0, 1.5, 3, and 4.5 h) and reversely transcribed into complementary DNA (cDNA). The amount of each eGFP mRNA was calculated by quantitative PCR (qPCR) analysis in normalization of endogenous 18S rRNA. Relative mRNA levels were in percentage of their corresponding mRNAs at t=0. As shown in FIG. 7, over 50% unmodified, me$^1$ ψ-, or ψ-modified eGFP mRNAs were degraded, while approximately 75% 5moU-modified cGFP mRNA remained at t=4.5 h. These results suggested 5moU modifications significantly increased stability of eGFP mRNA.

In summary, two sets of chemically modified mRNAs (FLuc and eGFP mRNAs) were designed and synthesized, which incorporated full substitution of one or two types of chemically modified nucleotides. The effects of the chemically modified mRNAs on protein expression were investigated by varying conditions including temperature in the rabbit reticulocyte lysate system, cell types, and coding sequences. The results indicated that temperature doesn't affect the trend for a large set of mRNAs screening in the rabbit reticulocyte lysate. Yet, when conducting high throughput screening of chemically modified mRNAs, it is necessary to strictly control assay temperature in the rabbit reticulocyte lysate system in order to predict the top modified mRNAs since significant correlation of luciferase intensity in the rabbit reticulocyte lysate system at 30° C. and in Hep 3B cells was observed. Additionally, cell types and coding sequences play important roles in protein expression of different chemically modified mRNAs. Moreover, 5moU modifications significantly increased the stability of eGFP mRNA compared to unmodified and other modified mRNAs. Therefore, the chemical modification of mRNA may require specific design and screening for particular therapeutic applications or biological studies. Because numerous enzymes play essential roles in mRNA translation and protein expression, further mechanistic studies may elucidate mRNA-enzyme interactions involved in multiple signaling pathways. For example, Karikó et al reported that ψ-modified mRNA enhances translation by reducing the activation of RNA-dependent protein kinase (PKR) (Anderson, B. R., et. al. (2010) *Nucleic Acids Res.* 38, 5884-5892). Lastly, N$^1$-methylpseudouridine (me$^1$ψ), 5-methoxyuridine (5moU), and pseudouridine (v) were identified as exhibiting the largest increases on protein expression.

Methods and Protocols

Materials.

Rabbit reticulocyte lysate kit and Bright-Glo reagent were purchased from Promega Corporation. Eagle's Minimum Essential Medium (EMEM) was purchased from Corning Incorporated. RPMI-1640 Medium and Hep 3B cells were purchased from American Type Culture Collection. RNeasy Mini Kit was from QIAGEN. Dulbecco's Modified Eagle Medium (DMEM), Opti-MEM medium, fetal bovine serum, Lipofectamine 2000, High Capacity cDNA Reverse Transcription Kits and SYBR Green PCR Master Mix were purchased from Life technologies. Antarctic phosphatase was purchased from New England Biolabs.

Synthesis of Chemically Modified mRNA.

Chemically modified mRNAs encoding firefly Luciferase and green fluorescent protein respectively were synthesized using an in vitro transcription from the corresponding plasmid DNA template by TriLink BioTechnologies. Chemically modified nucleotides were completely substituted for their natural counterparts while synthesizing the mRNAs. The transcripts were then further modified for mammalian systems with 5' cap and 3' poly(A) tail structures. mRNAs were purified using commercially available silica-based spin columns. mRNAs were dephosphorylated with Antarctic phosphatase and repurified by silica-based spin column.

mRNA Translation in Rabbit Reticulocyte Lysate System.

Two microliters of FLuc mRNA (1 µg/µL) was added to 48 µL of rabbit reticulocyte lysate reaction assembly and the mixture was incubated at either 30° C. or 37° C. for 90 min. After incubation, 50 µL of the substrate consisting of 25 µL of Bright-Glo and 25 µL of PBS was added to 2.5 µL of the reaction mixture. Luminescence intensity was measured immediately after 5 minutes dark incubation.

mRNA Translation in Cells.

Hep 3B cells were cultured in Eagle's Minimum Essential Medium (EMEM), THP-1 cells in RPMI-1640 Medium and primary rat hepatocytes in Dulbecco's Modified Eagle Medium (DMEM). All medium supplemented with 10% fetal bovine serum. For FLuc mRNA translation, Hep 3B and THP-1 cells were seeded in 96-well white plates at a density of 10$^4$ cells/well. Following overnight culture, 50 ng of modified FLuc mRNA was complexed with Lipofectamine 2000 in Opti-MEM medium, and the mixture was added to each well after 5 min incubation. Twenty four hours post-transfection, 100 µL of Bright-Glo reagent was added to each well, and luminescence intensity was measured immediately after 5 minutes dark incubation. For cGFP mRNA translation, Hep 3B, THP-1 cells and primary rat hepatocytes were seeded in 6-well plates at a density of 2.0×10$^5$/well. After overnight culture, 2 µg of modified FLuc mRNA was complexed with Lipofectamine 2000 in Opti-MEM medium, and the mixture was added to each well after 5 min incubation. After 24 hours treatment, cells were harvested and the green fluorescence intensity was determined on a BD LSR II flow cytometer (BD Biosciences, San Jose, CA).

RNA Isolation, cDNA Synthesis and Quantitative PCR (qPCR).

Hep 3B cells were seeded in 6-well plates at a density of $3 \times 10^5$ cells/well and cultured overnight. 1 µg of eGFP mRNA complexed with Lipofectamine 2000 in Opti-MEM medium was transfected into cells. After one hour incubation, cells were rinsed twice to remove the residual RNA and incubated with fresh medium. At desired time points (t=0, 1.5, 3 and 4.5 h), total RNAs were extracted with RNeasy Mini Kit, reverse transcribed into complementary DNA (cDNA) by High Capacity cDNA Reverse Transcription Kits, and quantified with gene-specific primers (Table 1) and SYBR Green PCR Master Mix in a StepOne Plus Real Time PCR system (Applied Biosystems, Foster City, CA) according the manufacturer's instruction. The expression of the target gene versus that of the reference gene (18S rRNA) was calculated using formula $2^{-\Delta\Delta Ct}$, where $C_t$ was the cycle threshold value. The relative eGFP mRNA levels at different time points were normalized to the initial (t=0) eGFP mRNAs.

TABLE 1

List of gene-specific oligonucleotide primer sets used for SYBR Green real-time qPCR.

| Name | Forward primer sequence | Reverse primer sequence |
| --- | --- | --- |
| 18S rRNA | 5'-GCT CTA GAA TTA CCA CAG TTA TC-3' (SEQ ID NO: 4) | 5'-AAA TCA GTT ATG GTT CCT TTG GT-3' (SEQ ID NO: 5) |
| eGFP | 5'-ACG TAA ACG GCC ACA AGT TC-3' (SEQ ID NO: 6) | 5'-AAG TCG TGC TGC TTC ATG TG-3' (SEQ ID NO: 7) |

REFERENCES CITED IN THIS EXAMPLE (1) Sahin, U., Kariko, K., and Tureci, O. (2014) mRNA-based therapeutics—developing a new class of drugs. *Nat. Rev. Drug Discov.* 13, 759-780.
(2) Islam, M. A., Reesor, E. K., Xu, Y., Zope, H. R., Zetter, B. R., and Shi, J. (2015) Biomaterials for mRNA delivery. *Biomater. Sci.* 3, 1519-1533.
(3) McIvor, R. S. (2011) Therapeutic delivery of mRNA: the medium is the message. *Mol. Ther.* 19, 822-823.
(4) Pascolo, S. (2008) Vaccination with messenger RNA (mRNA). *Handb. Exp. Pharmacol.* 221-235.
(5) Tavernier, G., Andries, O., Demeester, J., Sanders, N. N., De Smedt, S. C., and Rejman, J. (2011) mRNA as gene therapeutic: how to control protein expression. *J. Control Release* 150, 238-247.
(6) Anguille, S., Smits, E. L., Lion, E., van Tendeloo, V. F., and Berneman, Z. N. (2014) Clinical use of dendritic cells for cancer therapy. *Lancet Oncol.* 15, e257-267.
(7) Zhao, Y., Moon, E., Carpenito, C., Paulos, C. M., Liu, X., Brennan, A. L., Chew, A., Carroll, R. G., Scholler, J., Levine, B. L., et al. (2010) Multiple injections of electroporated autologous T cells expressing a chimeric antigen receptor mediate regression of human disseminated tumor. *Cancer Res.* 70, 9053-9061.
(8) Li, B., Luo, X., Deng, B., Wang, J., McComb, D. W., Shi, Y., Gaensler, K. M., Tan, X., Dunn, A. L., Kerlin, B. A., et al. (2015) An orthogonal array optimization of lipid-like nanoparticles for mRNA delivery in vivo. *Nano Lett.* 15, 8099-8107.
(9) Kauffman, K. J., Dorkin, J. R., Yang, J. H., Heartlein, M. W., DeRosa, F., Mir, F. F., Fenton, O. S., and Anderson, D. G. (2015) Optimization of lipid nanoparticle formulations for mRNA delivery in vivo with fractional factorial and definitive screening designs. *Nano Lett.* 15, 7300-7306.
(10) Zangi, L., Lui, K. O., von Gise, A., Ma, Q., Ebina, W., Ptaszek, L. M., Spater, D., Xu, H., Tabebordbar, M., Gorbatov, R., et al. (2013) Modified mRNA directs the fate of heart progenitor cells and induces vascular regeneration after myocardial infarction. *Nat. Biotechnol.* 31, 898-907.
(11) Kormann, M. S., Hasenpusch, G., Aneja, M. K., Nica, G., Flemmer, A. W., Herber-Jonat, S., Huppmann, M., Mays, L. E., Illenyi, M., Schams, A., et al. (2011) Expression of therapeutic proteins after delivery of chemically modified mRNA in mice. *Nat. Biotechnol.* 29, 154-157.
(12) Thess, A., Grund, S., Mui, B. L., Hope, M. J., Baumhof, P., Fotin-Mleczek, M., and Schlake, T. (2015) Sequence-engineered mRNA without chemical nucleoside modifications enables an effective protein therapy in large animals. *Mol. Ther.* 23, 1456-1464.
(13) Hendel, A., Bak, R. O., Clark, J. T., Kennedy, A. B., Ryan, D. E., Roy, S., Steinfeld, I., Lunstad, B. D., Kaiser, R. J., Wilkens, A. B., et al. (2015) Chemically modified guide RNAs enhance CRISPR-Cas genome editing in human primary cells. *Nat. Biotechnol.* 33, 985-989.
(14) Wang, J., Exline, C. M., DeClercq, J. J., Llewellyn, G. N., Hayward, S. B., Li, P. W., Shivak, D. A., Surosky, R. T., Gregory, P. D., Holmes, M. C., et al. (2015) Homology-driven genome editing in hematopoietic stem and progenitor cells using ZFN mRNA and AAV6 donors. *Nat. Biotechnol.* 33, 1256-1263.
(15) Weissman, D., and Kariko, K. (2015) mRNA: fulfilling the promise of gene therapy. *Mol. Ther.* 23, 1416-1417.
(16) Kariko, K., Ni, H. P., Capodici, J., Lamphier, M., and Weissman, D. (2004) mRNA is an endogenous ligand for Toll-like receptor 3. *J. Biol. Chem.* 279, 12542-12550.
(17) Kariko, K., Muramatsu, H., Keller, J. M., and Weissman, D. (2012) Increased erythropoiesis in mice injected with submicrogram quantities of pseudouridine-containing mRNA encoding erythropoietin. *Mol. Ther.* 20, 948-953.
(18) Kariko, K., Muramatsu, H., Welsh, F. A., Ludwig, J., Kato, H., Akira, S., and Weissman, D. (2008) Incorporation of pseudouridine into mRNA yields superior nonimmunogenic vector with increased translational capacity and biological stability. *Mol. Ther.* 16, 1833-1840.
(19) Uchida, S., Kataoka, K., and Itaka, K. (2015) Screening of mRNA chemical modification to maximize protein expression with reduced immunogenicity. *Pharmaceutics* 7, 137-151.
(20) Andries, O., Mc Cafferty, S., De Smedt, S. C., Weiss, R., Sanders, N. N., and Kitada, T. (2015) N(1)-methylpseudouridine-incorporated mRNA outperforms pseudouridine-incorporated mRNA by providing enhanced protein expression and reduced immunogenicity in mammalian cell lines and mice. *J. Control Release* 217, 337-344.
(21) Anderson, B. R., Muramatsu, H., Nallagatla, S. R., Bevilacqua, P. C., Sansing, L. H., Weissman, D., and Kariko, K. (2010) Incorporation of pseudouridine into mRNA enhances translation by diminishing PKR activation. *Nucleic Acids Res.* 38, 5884-5892.

Example 3. Genome Editing Efficiency Using a Combination of Chemically Modified CRISPR-Cpf1 crRNAs and mRNAs CRISPR (clustered, regularly interspaced, short palindromic repeats) is part of adaptive immunity in bacteria and archaea (Makarova, K. S. et al. *Nat Rev Microbiol* 9, 467-477 (2011); Bosley, K. S. et al. *Nat Biotechnol* 33, 478-486 (2015)). CRISPR-associated protein 9 (Cas9) induces double stranded DNA breaks through complexation with two RNA molecules: CRISPR RNA (crRNA) and trans-activating crRNA (Jinek, M. et al. *Science* 337, 816-821 (2012); Cong, L. et al. *Science* 339, 819-823 (2013); Mali, P. et al. *Science* 339, 823-826 (2013)). Recently, CRISPR-Cpf1 from *Acidaminococcus* sp. (AsCpf1) and Lachnospiraceae (LbCpf1) (Zetsche, B. et al. *Cell* 163, 759-771 (2015); Dong, D. et al. *Nature* 532, 522-526 (2016); Fonfara, I., et al. *Nature* 532, 517-521 (2016); Yamano, T. et al. *Cell* (2016)), a second class 2 (type V) CRISPR system displayed comparable genome editing capability to Cas9. Genome-wide analysis suggested that Cpf1 may cause fewer off-target cleavages in comparison to Cas9 (Kleinstiver, B. P. et al. *Nat Biotechnol* 34, 869-874 (2016)), (Kim, D. et al. *Nat Biotechnol* 34, 863-868 (2016)). To exert sequence-specific endonuclease activity, Cpf1 is functional through a single crRNA without an additional tracrRNA (Zetsche, B. et al. *Cell* 163, 759-771 (2015); Fonfara, I., et al. *Nature* 532, 517-521 (2016)). As shown in FIG. 1, this crRNA (43 nucleotides) consists of a 5'-handle (20 nucleotides) and a guide segment (23 nucleotides) (Zetsche, B. et al. *Cell* 163, 759-771 (2015)). Cpf1 protein interacts with the pseudoknot structure formed by the 5'-handle of crRNA (Yamano, T. et al. *Cell* (2016)). A guide segment possesses complementary binding with the target DNA sequences. This complexes recognize a T-rich protospacer-adjacent motif (PAM) and leads to a staggered DNA double stranded break (Yamano, T. et al. *Cell* (2016)) (The dotted line denotes the cleavage sites, FIG. 11a).

To increase genome editing efficiency and reduce off-target effects of CRISPR systems, previous studies explored a wide variety of approaches (Slaymaker, I. M. et al. *Science* 351, 84-88 (2016); Kleinstiver, B. P. et al. *Nature* 529, 490-495 (2016)). Among them, chemical modifications of CRISPR-Cas9 demonstrated enhanced activity in a number of human cells (Hendel, A. et al. *Nat Biotechnol* 33, 985-989 (2015); Rahdar, M. et al. *Proc Natl Acad Sci USA* 112, E7110-7117 (2015)). For example, guide RNAs with three chemically modified nucleotides at both 5'- and 3'-end strongly improved Cas9-mediated genome editing in human primary T cells (Hendel, A. et al. *Nat Biotechnol* 33, 985-989 (2015)). Moreover, incorporation of chemically modified nucleotides was able to remain indel percentage using Cas9 and truncated guide RNAs (Rahdar, M. et al. *Proc Natl Acad Sci USA* 112, E7110-7117 (2015)). In addition, the structures of guide RNA for Cas9 play important roles in gene cutting (Chen, B. et al. *Cell* 155, 1479-1491 (2013); Dang, Y. et al. *Genome Biol* 16, 280 (2015)). Yet, no literature is known about the effects of chemically modified crRNAs and Cpf1 mRNAs on their genome editing efficiency and off-target effects. In this example, 26 chemically modified crRNAs were investigated, which established comprehensive structure-activity (gene editing efficiency) relationships. A ψ-modification was identified in this example as a favorable chemical alteration for Cpf1 mRNA. Importantly, combination of crRNA and ψ-mRNA significantly increased gene editing efficiency over 300% compared to the positive control group. This combination induced more dramatic improvement of gene cutting efficiency when utilizing LbCpf1. More interestingly, AsCpf1 in complexation with LbCpf1 crRNA was able to effectively achieve genome editing while LbCpf1 in complexation with AsCpf1 crRNA completely lost its function. Overall, our findings offer a promising strategy for broad genome editing applications.

Figure 9A:
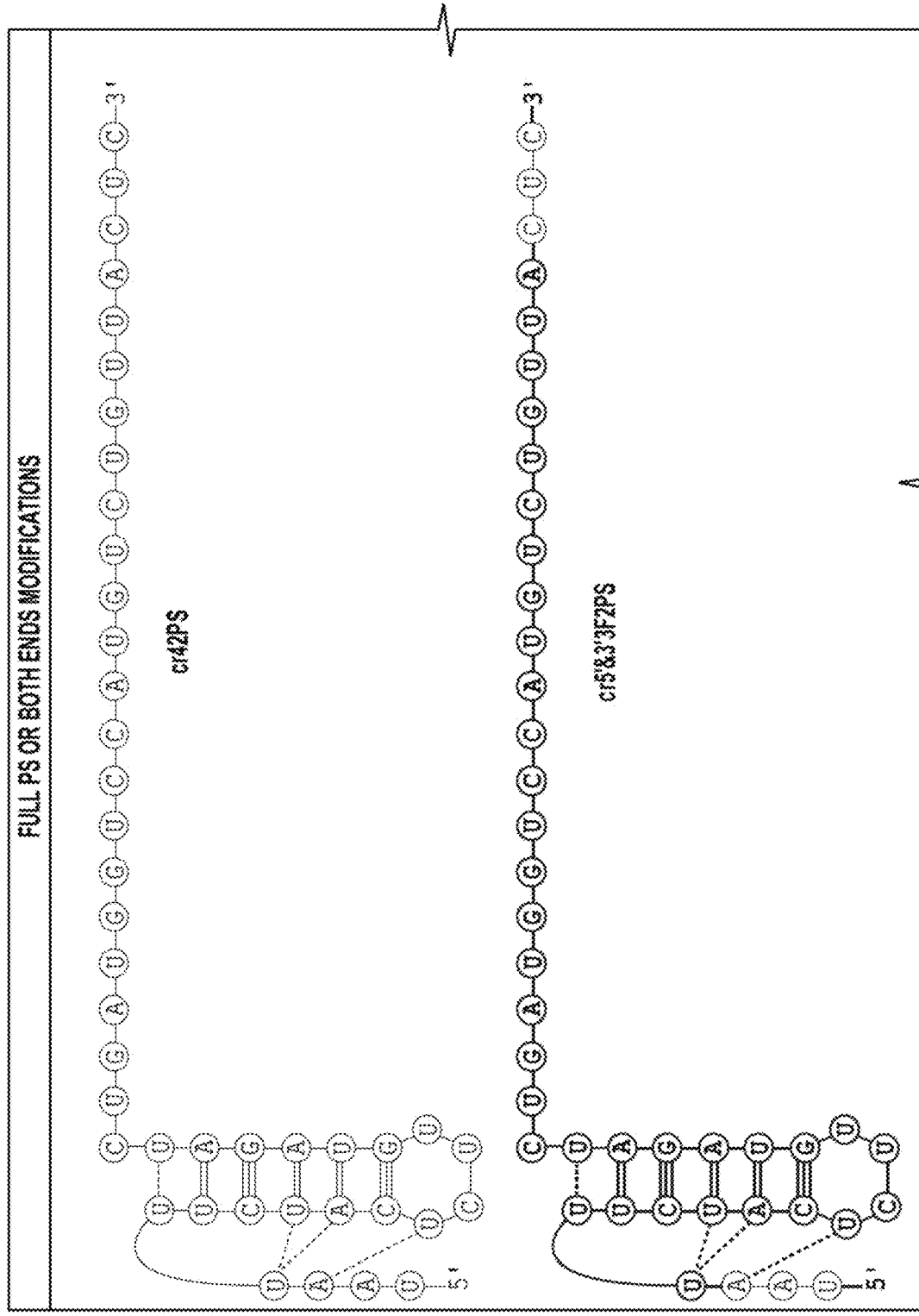
FIGS. 9A-9E. Design of chemically modified crRNAs and Cpf1 mRNA and their gene editing efficiency.
Figure 9B:
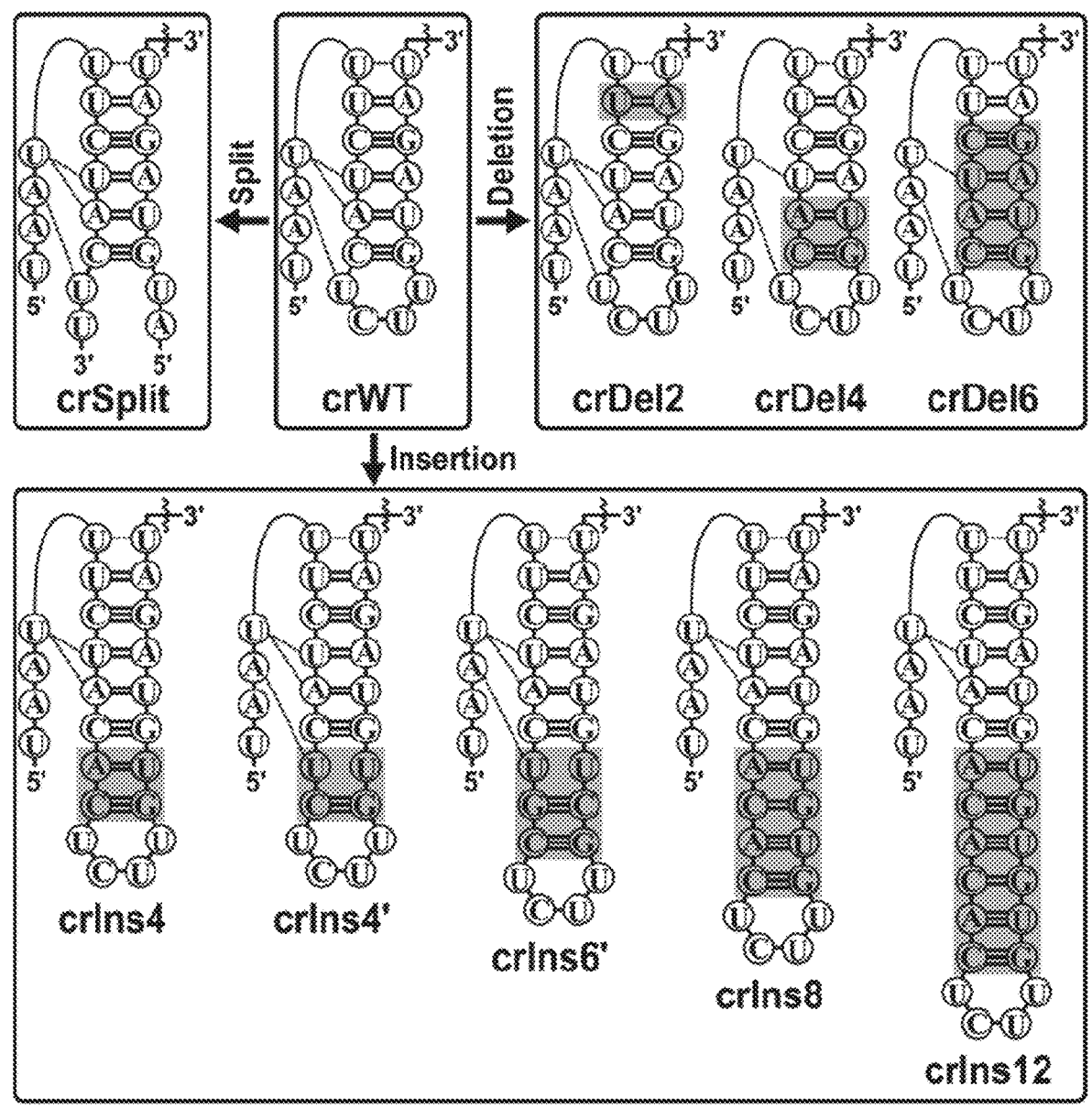
Figure 9C:
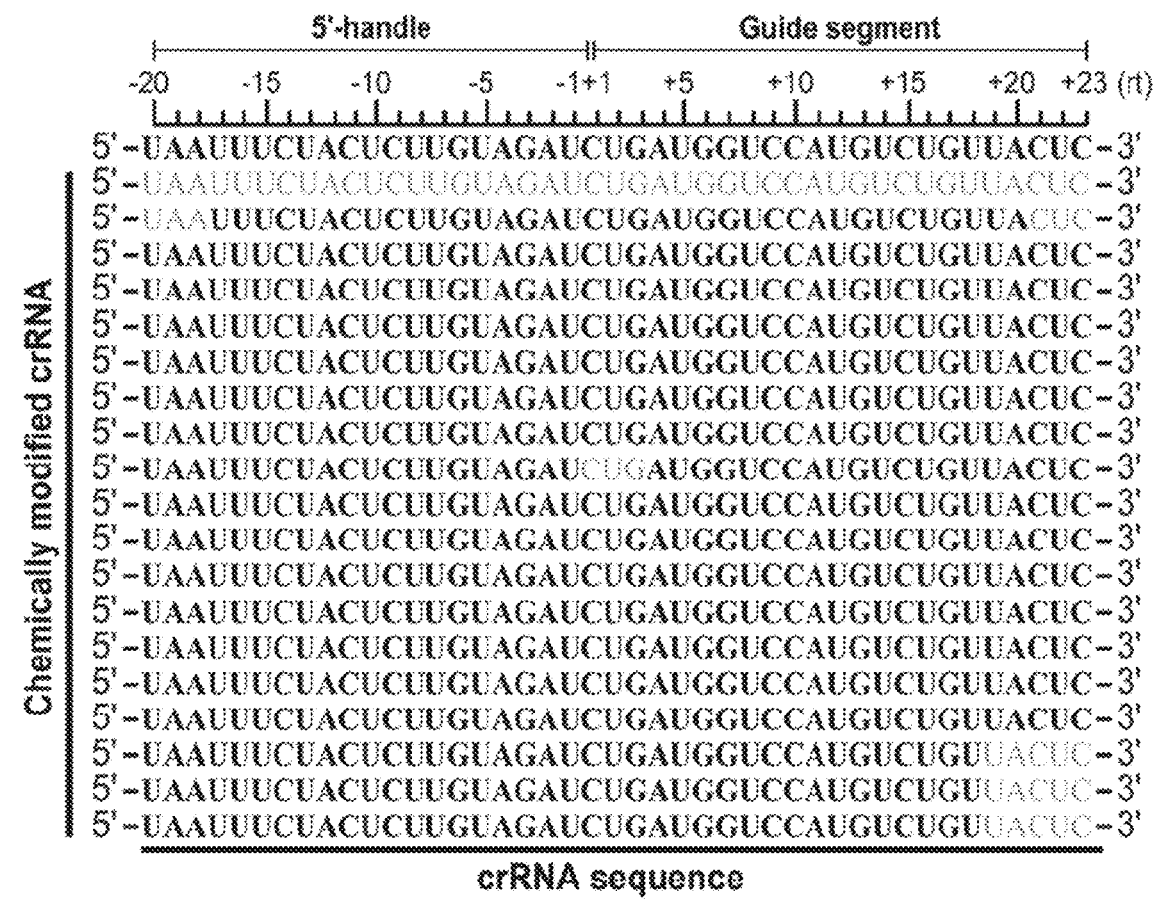
Figure 9C:
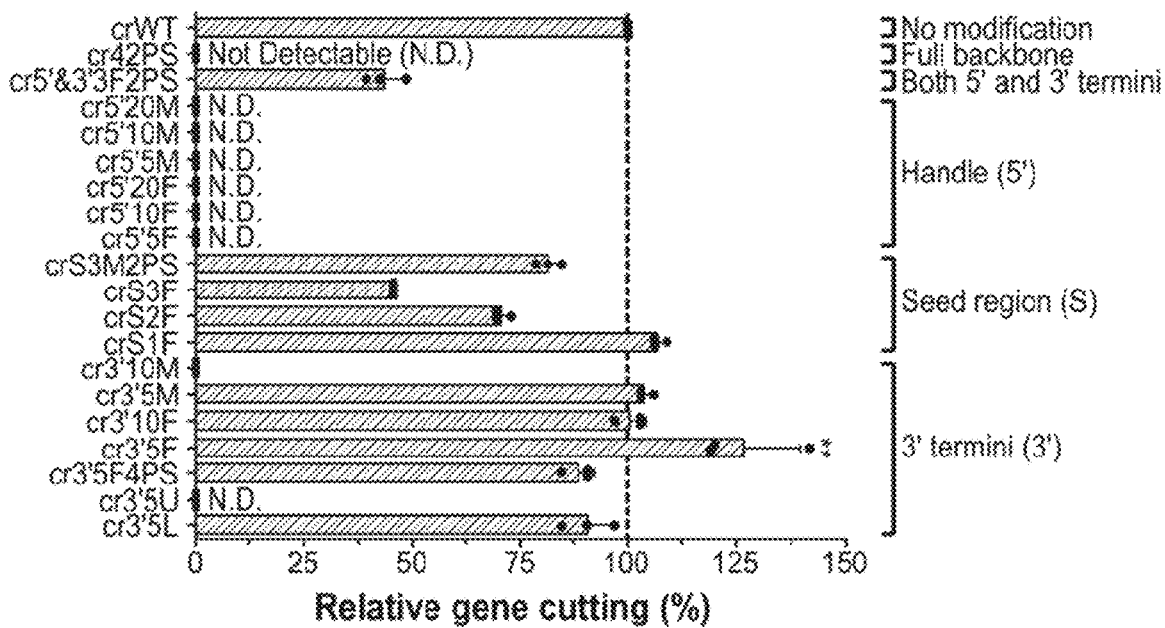
Figure 9D:
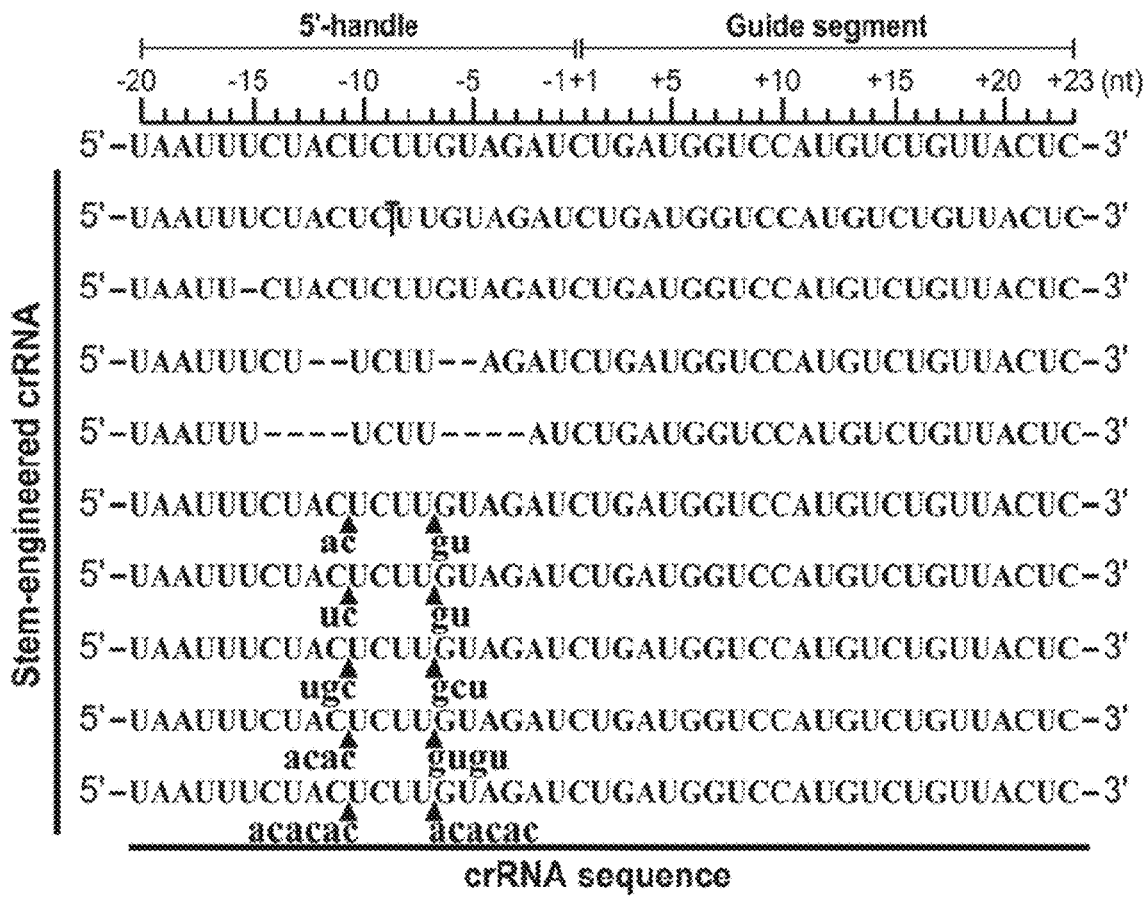
Figure 9D:
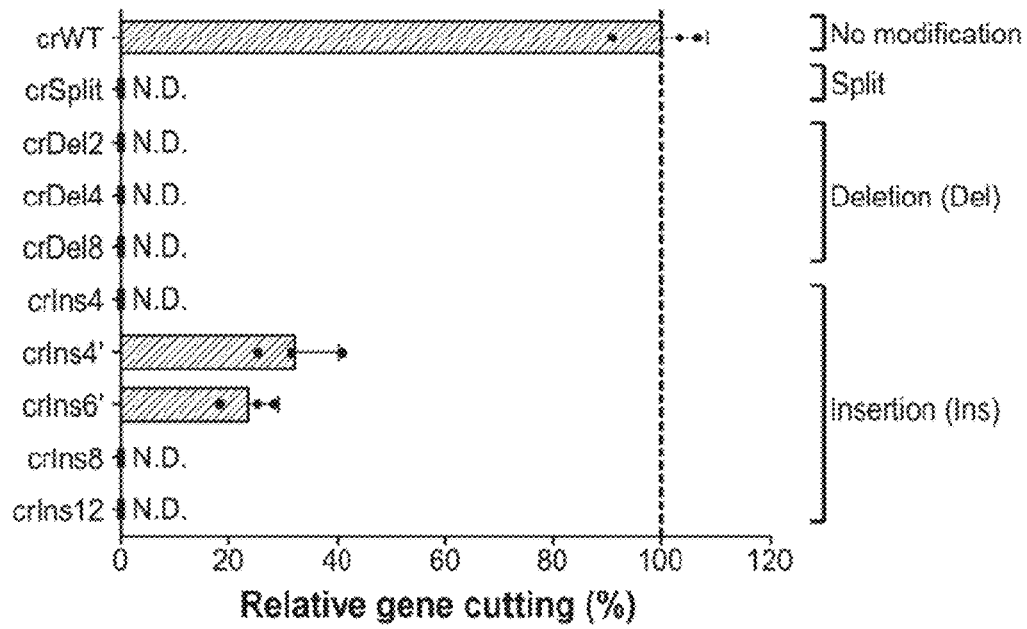
Figure 14:
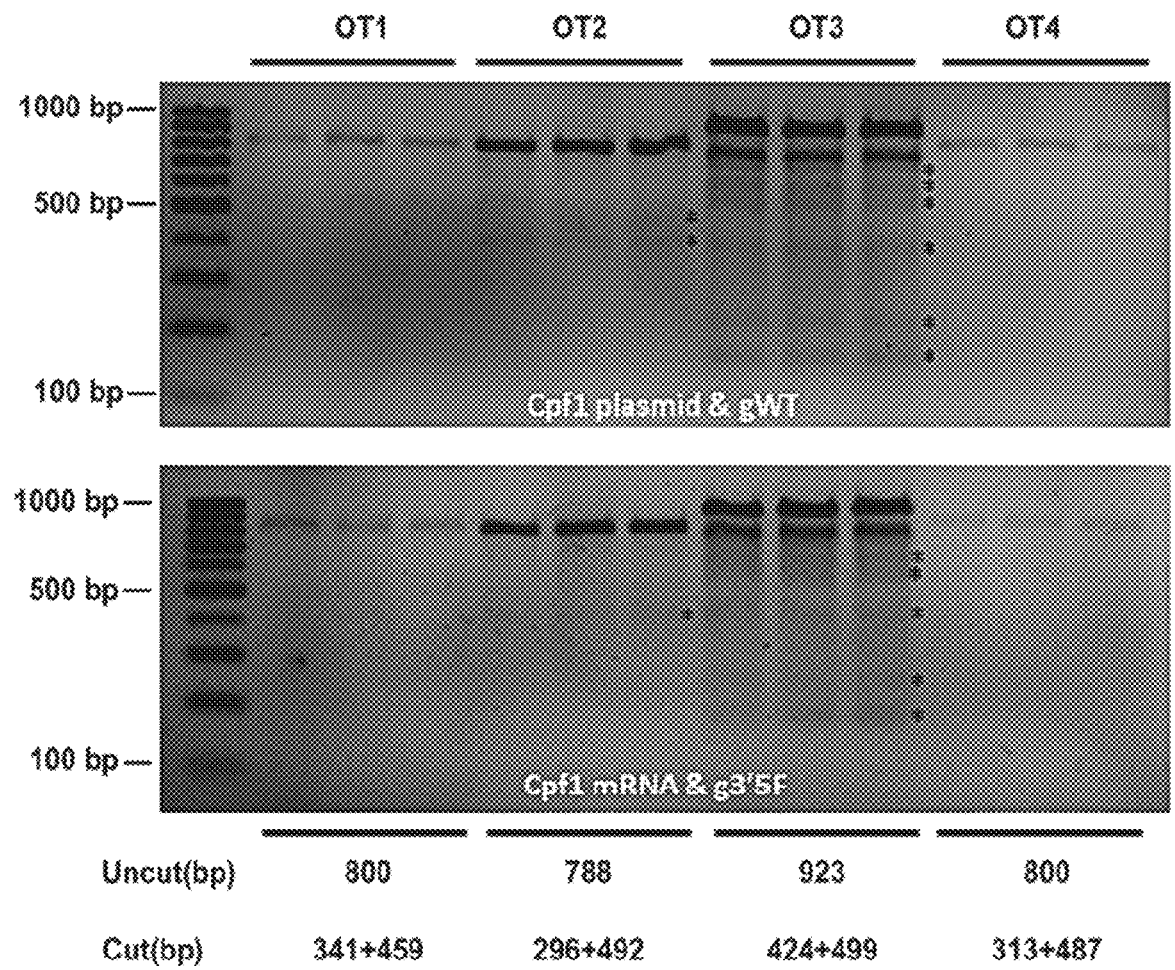
FIG. 14. T7E1 cleavage assay measuring the off-target effect. The size of predicted T7E1 fragments was shown at the bottom of gels. *, nonspecific bands.
Figure 15:
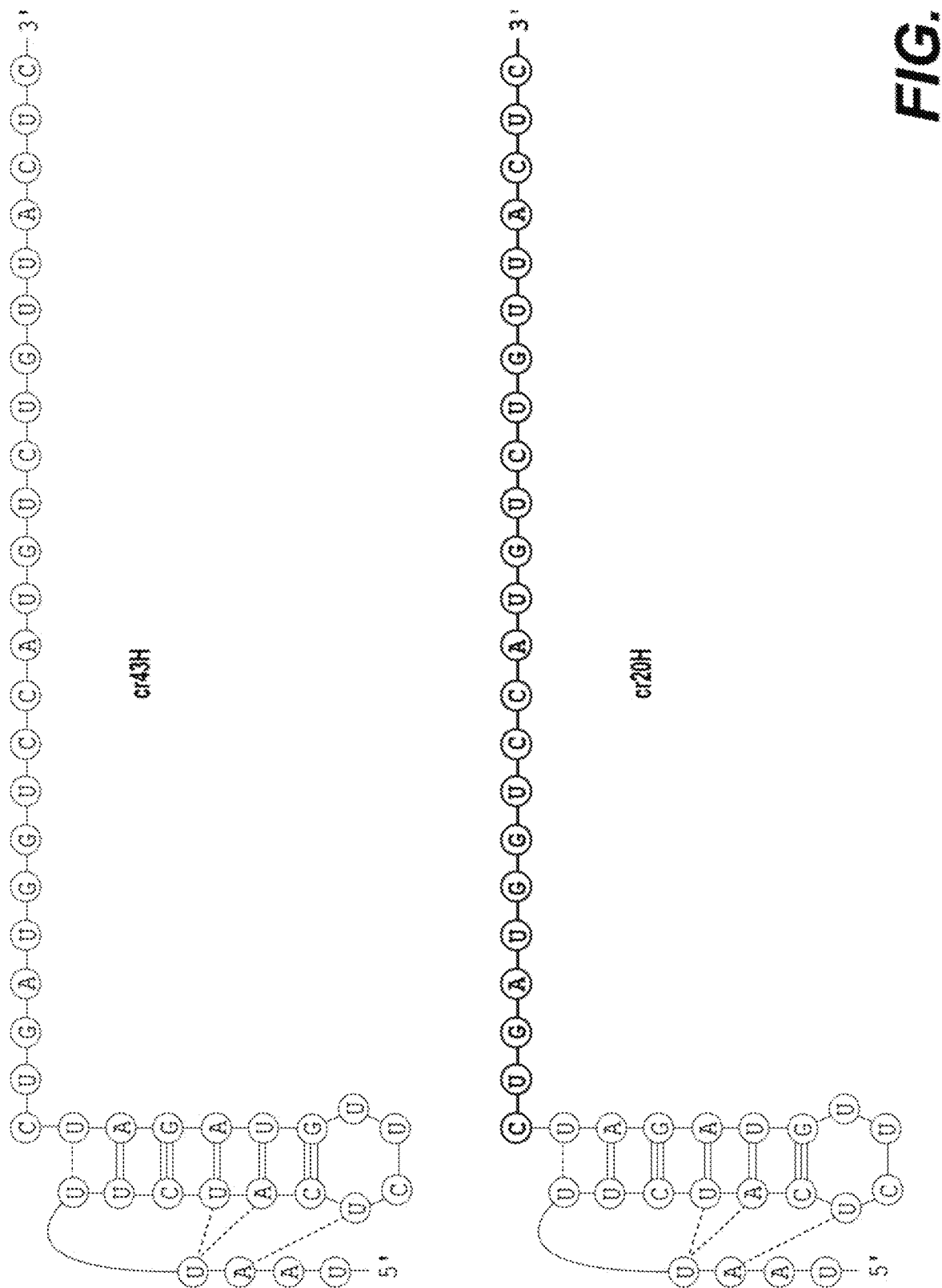
FIG. 15. Chemically modified crRNAs. 2'-H substitutions, Unlocked and locked nt are shown. For cr121F, 2'-F modifications were applied to 5, 6, 9, 10, 12-14, 16-19, 29-32, 37 and 39-43 positions. For cr110F, 2'-F modifications were applied to 29-32, 37 and 39-43 positions. The 5' uridine was seen as position 1.
Figure 18:
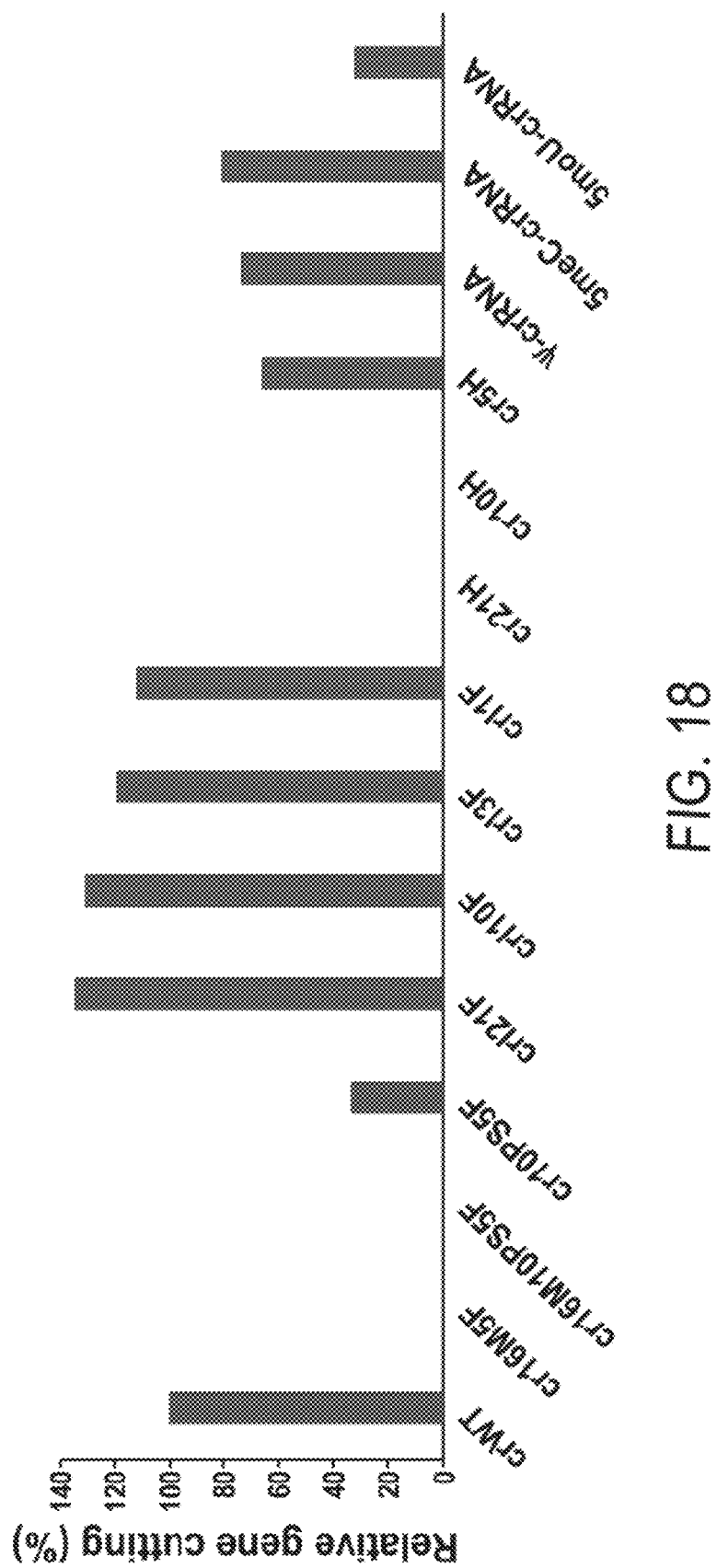
FIG. 18. Gene cutting efficiency of chemically modified crRNAs. Indel is determined by the T7E1 cleavage assay, and normalized to that of the treatment with crWT and plasmid encoding AsCpf1.

To study the effects of chemically modified crRNAs on gene editing efficiency, three types of chemically modified nucleotides were utilized in this example: phosphorothioate (PS), 2'-O-Me-, and 2'-F-modifications (Watts, J. K., et al. *Drug Discov Today* 13, 842-855 (2008)) (FIG. 14). Based on previous findings for CRISPR-Cas9 in the literature (Hendel, A. et al. *Nat Biotechnol* 33, 985-989 (2015); Rahdar, M. et al. *Proc Natl Acad Sci USA* 112, E7110-7117 (2015)), a full-backbone PS-modified cr42PS and a cr5'&3'3F2PS (three 2'-F modifications with two PS linkages at both 5' and 3' end) was synthesized. These crRNAs targeting the DNMT1 locus were purified on denaturing polyacrylamide gels and their structures were validated by mass spectrometry analysis (Sequence information and mass spectrometry data are included in FIGS. 19 and 20). HEK293T cells were treated with synthesized crRNAs and plasmid encoding Cpf1 complexed with Lipofectamine 3000 reagent. Gene editing efficiency was quantified using a T7E1 assay (Kim, D. et al. *Nat Biotechnol* 34, 863-868 (2016)). Relative gene cutting efficiency in FIG. 9 was normalized to the treatment of unmodified crRNA (crWT) and plasmid encoding AsCpf1. As shown in FIG. 9c, both crRNAs displayed dramatic reduction of gene editing capability, which suggests that chemical modifications of Cpf1 crRNA are not in the same pattern as Cas9 guide RNAs. Additional experiments were conducted using chemical modifications at the 5'-handle, seed region, and 3'-termini. Five, ten, or twenty nucleotides with 2'-O-Me-, and 2'-F-modifications, respectively, were introduced at the 5'-handle of the crRNAs, which led to complete loss of activity. These data indicate that 5'-handle is not favorable for chemical modifications. Then, four modifications were made at the seed region, crS3M3PS, crS3F, crS2F, and crS1F (FIG. 9a). Although all four crRNAs diminished indel percentage, the results inferred interesting structure-activity relationship. The order of efficiency is crS3F<crS2F<crS1F, which indicated that the seed region may tolerate slight modifications. Furthermore, at the 3'-termini (FIG. 9a), five or ten nucleotides with 2'-O-Me- and 2'-F-modifications, respectively, were incorporated Interestingly, while 2'-O-Me-modifications decreased the activity, five or ten 2'-F-modifications improved the efficiency 119% and 111%, respectively compared to the crWT. In addition to five 2'-F-modifications at the 3'-termini, incorporation of PS modifications hampered the efficiency (FIG. 9c). We also noticed that substitution of some or full RNA bases of crWT with DNA bases (FIG. 15) severely impaired cutting activities, and full A, U or C bases substitution with corresponding m1A, pseudoU (or 5moU) or 5meC modified bases did not enhance their activities (FIG. 18). Lastly, the 5'-handle was modified by split of the crRNAs, deletion or insertion of nucleotides. Current crRNAs with split sequences and deletion of nucleotides exhibited no gene editing function (FIG. 9d). To some extent, insertion of four or six nucleotides retained the activity (FIG. 11e). Moreover, the activity is dependent on inserted base pairs (FIG. 9d, crIns4 vs crIns4'). Collectively, these results revealed the following SAR and design criteria for crRNAs: (I) PS linkage replacement generally hampered gene editing efficiency; (II) 5'-handle is not a preferred region for chemical modifications; current results indicate 5'-handle does not tolerate split of the crRNAs, deletion or insertion of nucleotides; (III) seed region is sensitive to chemical modifications and can only accommodate slight modifications; (IV) 3'-termini is favorable for certain chemical modifications, such as 2'-F modifications; (V) A combination of chemical modifications at both 5'- and 3'-ends of crRNA reduced the activity to some extent.

Figure 9E:
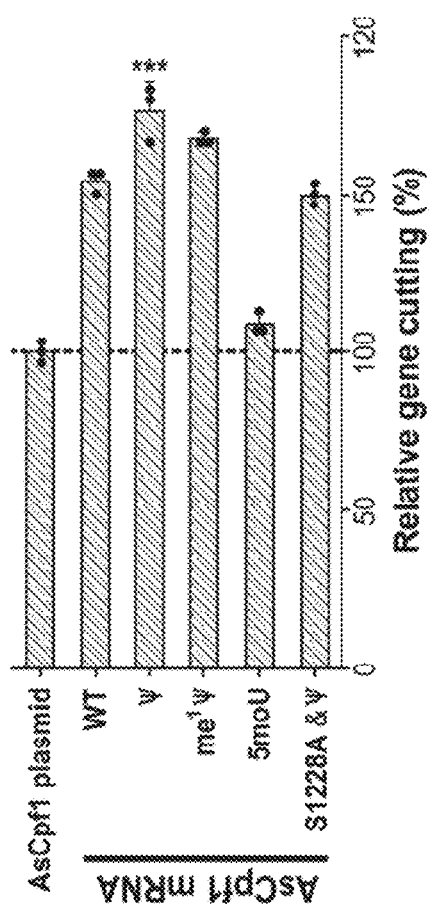

Meanwhile, the effects of chemically modified AsCpf1 mRNAs on their gene editing efficiency were investigated. Pseudouridine (ψ), N'-methylpseudouridine (me$^1$ψ), and 5-methoxyuridine (5moU) modified AsCpf1 mRNA was also designed, which were produced via an in vitro transcription. HEK293T cells were treated with crWT and modified Cpf1 mRNA. As shown in FIG. 9e, ψ- and me$^1$ψ-modified AsCpf1 mRNA showed higher activity (165% and 132%, respectively) than plasmid encoding AsCpf1, while 5moU modification decreased the activity. In addition, a recent literature reported that plasmid encoding AsCpf1 with a S1228A mutation improved gene editing efficiency (Yamano, T. et al. Cell (2016)). Therefore, AsCpf1 mRNA (S1228A mRNA) with a S1228A mutation and ψ-modification was also constructed. S1228A mRNA displayed comparable activity to original ψ-modified mRNA (FIG. 9e).

Terminology of the Cpf1-family orthologs: *Acidaminococcus* sp. BV3L6 Cpf1 (AsCpf1); *Francisella tularensis* subsp. *Novicida* U112 Cpf1 (FnCpf1); Lachnospiraceae bacterium MC2017 Cpf1 (Lb3Cpf1); *Butyrivibrio proteoclasticus* Cpf1 (BpCpf1); Parcubacteria bacterium GWC2011_GWC2_44_17 Cpf1 (PbCpf1); Peregrinibacteria bacterium GW2011_GWA_33_10 Cpf1 (PeCpf1); *Leptospira inadai* Cpf1 (LiCpf1); *Smithella* sp. SC_K08D17 Cpf1 (SsCpf1); Lachnospiraceae bacterium MA2020 Cpf1 (Lb2Cpf1); *Porphyromonas crevioricanis* Cpf1 (PcCpf1); *Porphyromonas macacac* Cpf1 (PmCpf1); *Candidatus methanoplasma termitum* Cpf1 (CMtCpf1); *Eubacterium eligens* Cpf1 (EeCpf1); *Moraxella* bovoculi 237 Cpf1 (MbCpf1); *Prevotella disiens* Cpf1 (PdCpf1); Lachnospiraceae bacterium ND2006 Cpf1 (LbCpf1).

Figure 16:
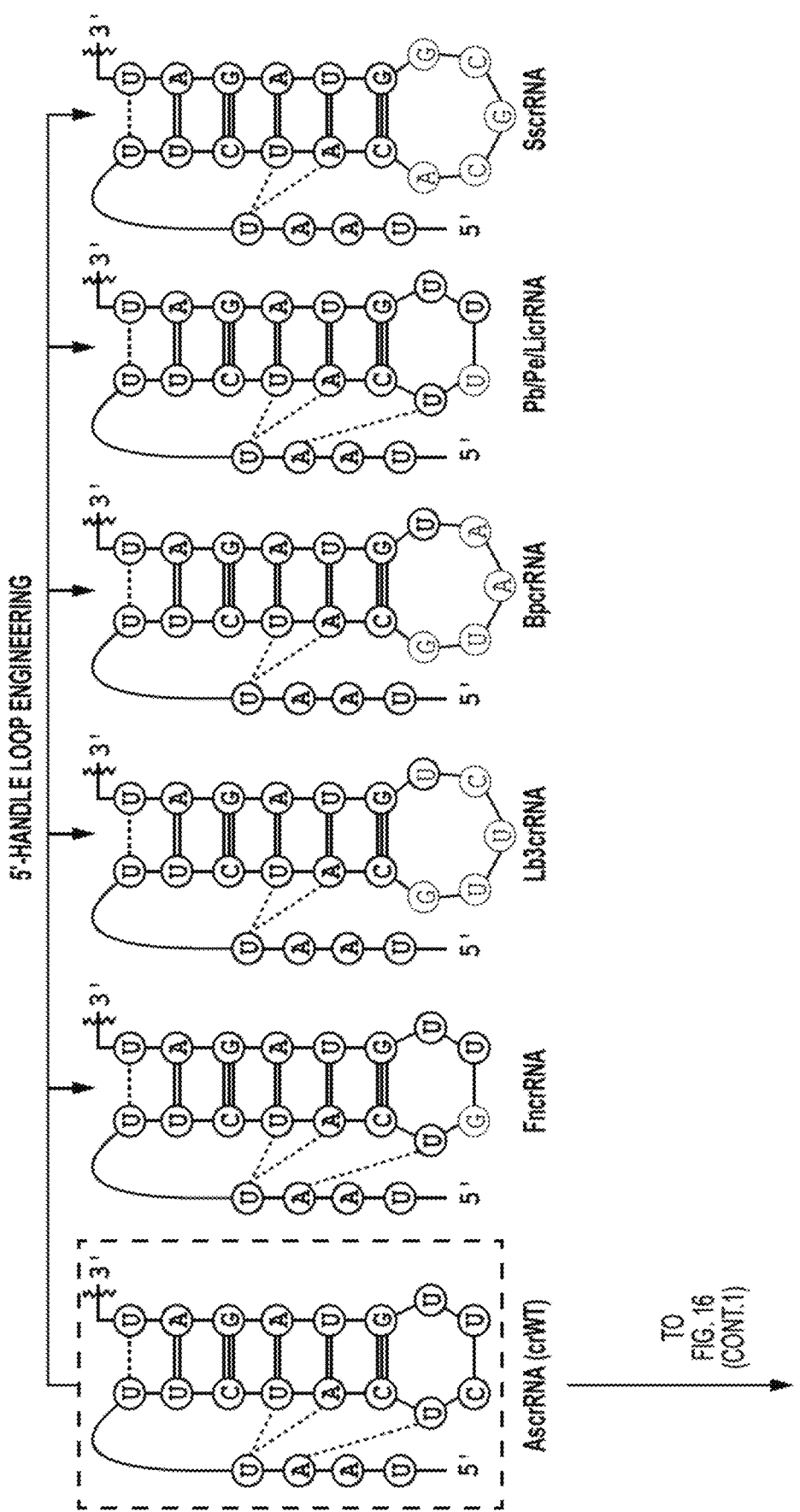
FIG. 16. Loop engineering of crRNAs. (a) Nucleotides of the loop were altered according to crRNAs from other 15 Cpf1-family orthologs. crRNAs were termed by combining initial of Cpf1 protein and crRNA; crRNAs of PbCpf1, PeCpf1 and LiCpf1 share the same loop UUUU; crRNAs of Lb2Cpf1, PcCpf1 and PmCpf1 share the same loop UAUU. (b) Gene cutting efficiency of loop engineered crRNAs in the presence of ψ-modified AsCpf1 mRNA. Gene cutting efficiency was determined by the T7E1 cleavage assay, and normalized to that of the treatment with AscrRNA and ψ-modified AsCpf1 mRNA. N.D., Not detectable. Data were expressed as the mean±S.D. from three biological replicates (*, P<0.05, Lb2crRNA versus to AscrRNA; t test, double-tailed).
Figure 17:
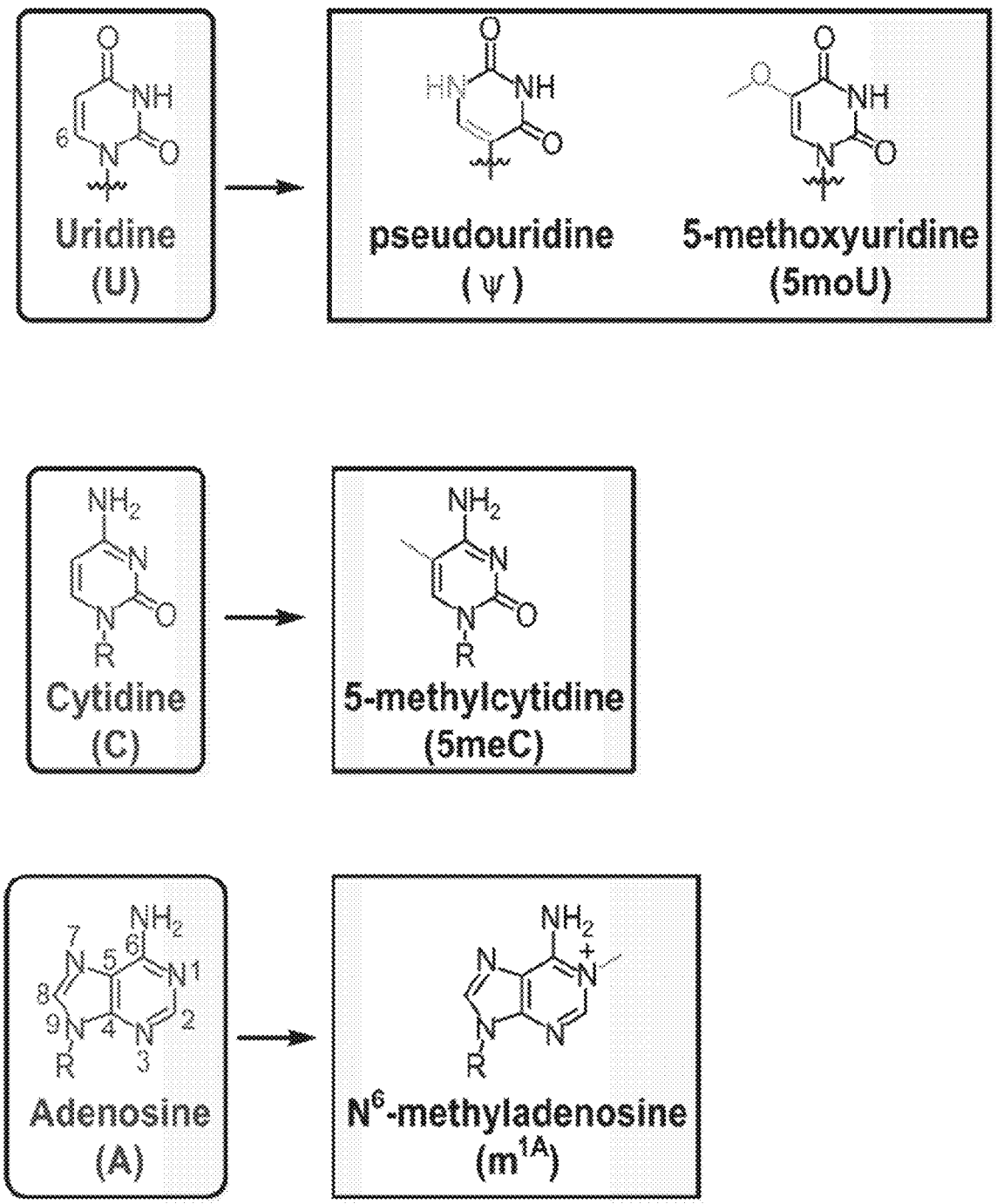
FIG. 17. Schematic diagram depicting chemical modifications applied to CRISPR-Cpf1 crRNAs. For Ψ-modified crRNA, all U bases of wide-type crRNA can be substituted with pseudoU (Ψ). For 5moU-modified crRNA, all U bases can be substituted with 5moU. For 5meC-modified crRNA, all C bases can be substituted with 5meC. For $m^1A$-modified crRNA, all A bases can be substituted with $m^1A$.

Inspired by crRNAs from other 15 Cpf1-family, we then engineered the loop [U(-10)-C(-9)-U(-8)-U(-7)] of 5'-handle by substituting the loop of wild-type AsCpf1 crRNA (crWT here is defined as AscrRNA to distinguish crRNAs from other Cpf1-protein family) with those from crRNAs of other Cpf1 family orthologs to investigate the effects of loop on gene cutting activity (FIG. 16a; crRNAs were termed by combining initial of Cpf1 protein and crRNA; crRNAs of PbCpf1, PeCpf1 and LiCpf1 share the same loop UUUU; crRNAs of Lb2Cpf1, PcCpf1 and PmCpf1 share the same loop UAUU). Interestingly, co-delivery of ψ-modified AsCpf1 mRNA and a panel of loop engineered crRNAs revealed that crRNAs with four-membered loop including FncrRNA, Pb/Pe/LicrRNA and Lb2/Pc/PmcrRNA induced evident cleavage on the target locus. Cytosine at position −9 tolerates nucleotide changes and the order of potency is: adenine (A)>cytosine (C)>guanine (G)>uridine (U). In addition, crRNAs with three-membered (EecrRNA) or five-membered loop (MbcrRNA and LbcrRNA) reduced the activity (FIG. 16b). Meanwhile, if the uridine at position −10 was replaced by G (Lb3crRNA and BpcrRNA) or A (SscrRNA) on the five-membered loop, crRNAs completely lost function (FIG. 16b). These results suggested that U (−10) is a critical position for gene editing, consistent with the findings from the crystal structure of AsCpf1. After sequence alignment, we observed that the whole sequence of AscrRNA was fully matched with that of crRNAs from FnCpf1, Pb/LiCpf1 and Lb2/Pc/Pm Cpf1 expect PeCpf1 (According to the crystal structure of AsCpf1-crRNA-target DNA complex, uridine at position −20 is not involved in the complexation. Hence, U(-20) was not included for alignment). In other words, AsCpf1 is able to complex with these crRNAs, attaining effective genome editing. These data, to our knowledge, first uncovered the cross complexation between AsCpf1 and crRNAs in the Cpf1 family, which expand the applicability of crRNAs, and are conducive to our understanding of the CRISPR-Cpf1 system and its potential biological and therapeutic applications. Lastly, we investigated the applicability of crRNAs for LbCpf1. We treated cells with loop engineered crRNAs as shown in FIG. 3c in the presence of ψ-modified LbCpf1 mRNA. Except its own LbcrRNA, LbCpf1 only led to reduced indel with Lb2/Pc/PmcrRNA, AscrRNA, and MbcrRNA, while no activity for other crRNAs (FIG. 16c), indicating different crRNA applicability between AsCpf1 and LbCpf1.

To study the combination effects of chemically modified crRNA and AsCpf1 mRNAs, HEK293T cells were treated with the top-performing modified crRNA and AsCpf1 mRNA (cr3'5F and -modified AsCpf1 mRNA). Strikingly, this combination significantly enhanced the gene editing efficiency over 250% compared to the treatment of crWT and plasmid encoding Cpf1 (FIG. 10a). We then analyzed the interaction among crRNA, AsCpf1 protein and target DNA. Crystal structure of the AsCpf1 complex indicates that 2'-OH of ribose on crRNA at the following positions plays a trivial role: −16, −15, −12, −11, −9, −8, −7, −5, −4, −3, −2, +1, +6, +8, +9, +10, +11, +12, +17, +19, +20, +21, +22 and +23. Based on this analysis, we designed additional three type of crRNAs: crI21F, crI16M5F and crI16M10PS5F (FIG. 15, FIGS. 19 and 20), by introducing interspersed modifications at the ribose units without interaction with AsCpf1 and target DNA and avoiding modifications at the seed region (+1 to +8). Interestingly, crI21F was comparable to cr3'5F, whereas crI16M5F and crI16M10PS5F dramatically weakened the activity of crRNA (FIG. 18). Since cr3'5F possesses less modifications than crI21F, we further investigated the applicability of cr3'5F in Hep3B (a human hepatoma cell line) and U87 cells (a human glioblastoma cell line). Consistent with the results in HEK293T cells, combination of cr3'5F and ψ-modified AsCpf1 mRNA 328% gene cutting for Hep3B (p<0.001, FIG. 12b) and 293% for U87 cells (p<0.001, FIG. 10a) compared to the treatment of crWT and plasmid encoding AsCpf1. To investigate the applicability in different cells, similar experiments were conducted in Hep3B cells, a human hepatoma cell line. Consistent with the results in HEK293T cells, combination of cr3'5F and ψ-modified AsCpf1 mRNA induced 328% gene cutting compared to the treatment of crWT and plasmid encoding Cpf1 (FIG. 10a). In addition to DNMT1 crRNA, gene cutting efficiency was examined for two target gene, AAVS1 and FANCF-2 loci 11. Regarding AAVS1 locus (FIG. 10b), the order of potency in HEK293T cells is cr3'5F+ψ-modified AsCpf1 mRNA>crWT+ψ-modified AsCpf1 mRNA>cr3'5F+AsCpf1 plasmid>crWT+AsCpf1 plasmid. cr3'5F+ψ-modified AsCpf1 mRNA is 2.77-fold more efficient than crWT+AsCpf1 plasmid (p<0.001). The enhanced efficiency was also observed in Hep3B and U87 cells (257% and 394% increase, respectively; FIG. 4b). For FANCF-2 locus, the trend is consistent with that for AAVS1 locus (FIG. 10c). These results demonstrate the broad applicability of the chemically modified crRNAs and Cpf1 mRNAs.

Along with AsCpf1, LbCpf1 is another important endonuclease in the Cpf1-family, which displayed genome editing ability in human cells[6,7]. To investigate whether our strategy is applied to the LbCpf1, we utilized similar chemical modifications for LbCpf1 mRNA as well as its corresponding crRNA (LbCpf1 crRNA). As shown in FIG. 10d, the combination of LbCpf1 crWT+LbCpf1 plasmid led to no detectable gene cutting, while the combination of LbCpf1 cr3'5F (Lbcr3'5F)+ψ-modified LbCpf1 mRNA induced remarkable gene cutting activity in all three cell lines tested. Moreover, LbCpf1 cr3'5F was more efficient than LbCpf1 crWT. These results further proved the concept of our chemical modifications to advance CRISPR-Cpf1 mediated genome editing.

Potential off-target effects are one of the major concerns for CRISPR mediated gene editing and may limit its applications (Slaymaker, I. M. et al. *Science* 351, 84-88 (2016); Kleinstiver, B. P. et al. Nature 529, 490-+(2016)). To study off-target effects of chemically modified Cpf1 mRNAs and crRNAs, the top four previously defined off-target sites were selected and a T7EI assay was performed at each genomic site. No detectable indels were observed in both treatment groups (cr3'5F+ψ-modified AsCpf1 mRNA and crWT+plasmid encoding Cpf1; FIG. 14). To further characterize on-target and off-target effects, targeted deep sequencing was conducted using the samples as that in FIG. 10a. CRISP-Resso was utilized to analyze the deep sequencing data (Pinello, L. et al. *Nat Biotechnol* 34, 695-697 (2016)). Similar to the results from T7E1 assays, combination of cr3'5F and ψ-modified AsCpf1 mRNA induced 311% gene cutting compared to the treatment of plasmid encoding Cpf1 and crWT (FIG. 11a). In addition, no significant difference was observed for off-target gene cutting between cr3'5F+ψ-modified AsCpf1 mRNA and crWT+plasmid encoding Cpf1 (FIG. 11a). The majority of the on-target indels were occurred within the −50 bp of the predicted cleavage site (FIG. 11c). Compatible with the results in the literature (Kim, D. et al. *Nat Biotechnol* 34, 863-868 (2016)), Cpf1 mainly induced deletions at the targeted gene site (FIGS. 11b and 11c).

Figure 10:
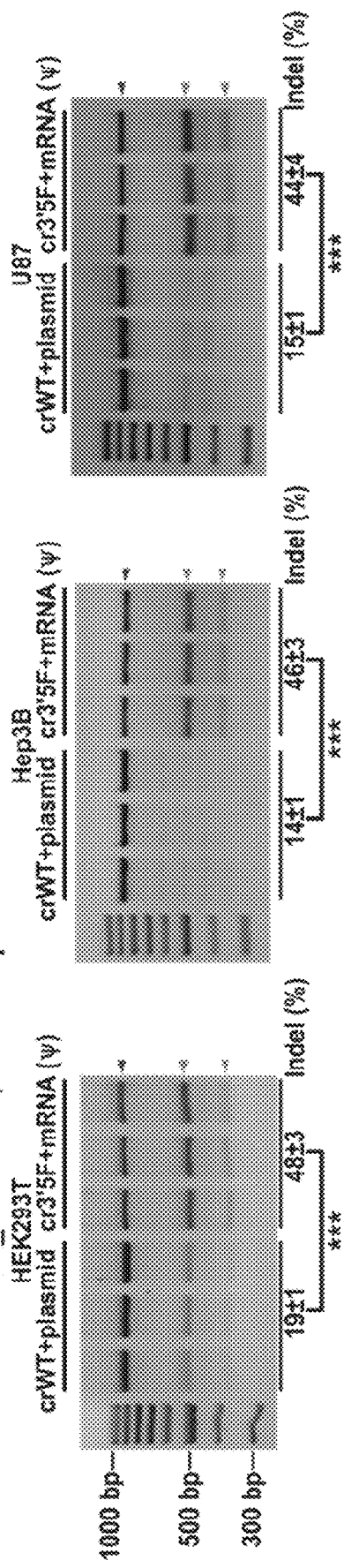
FIG. 10. Increasing gene editing efficiency through combination of chemically modified crRNA and Cpf1 mRNA. (a, b, c) AsCpf1-mediated gene cutting efficiency for the human DNMT1-3 (a), AAVS1 (b) and FANCF-2 (c) locus in HEK293T, Hep3B and U87 cells. (d) LbCpf1-mediated gene cutting efficiency for the human DNMT1-3 in HEK293T, Hep3B and U87 cells. Indel percentage at each locus was determined using the T7E1 assay by quantification of the uncut (solid arrow) and cut DNA bands (hollow arrow), and expressed as the mean±S.D. from three biological replicates (, P<0.01; *, P<0.001; t test, double-tailed).
Figure 10:
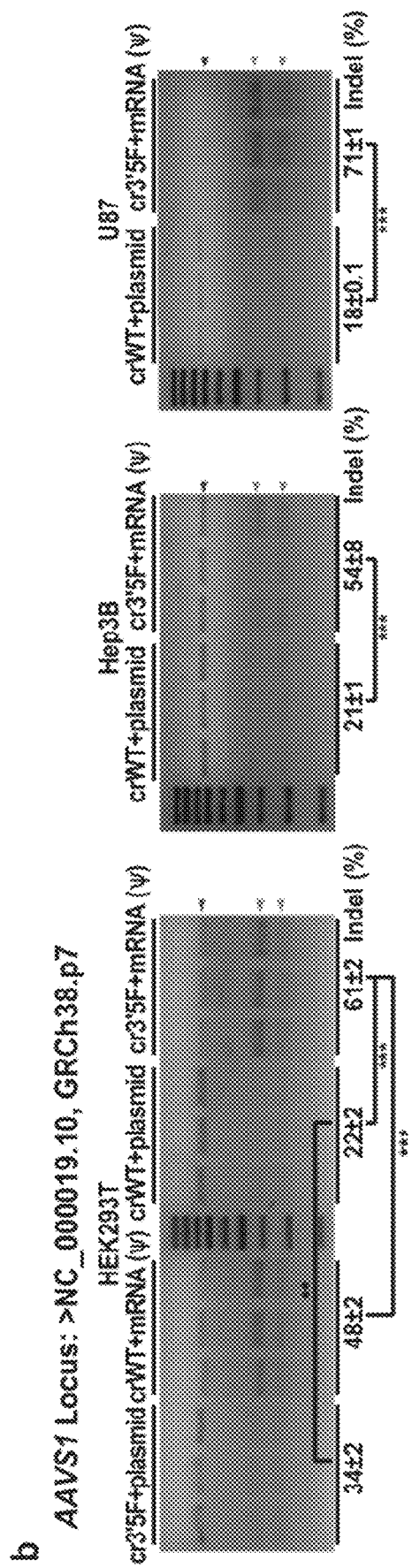
Figure 10:
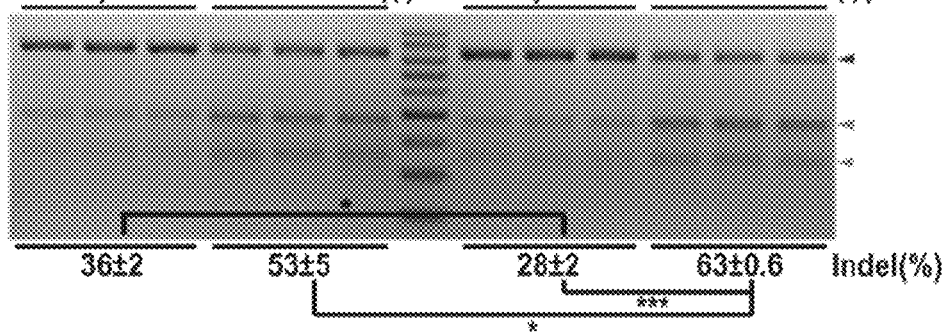
Figure 10:
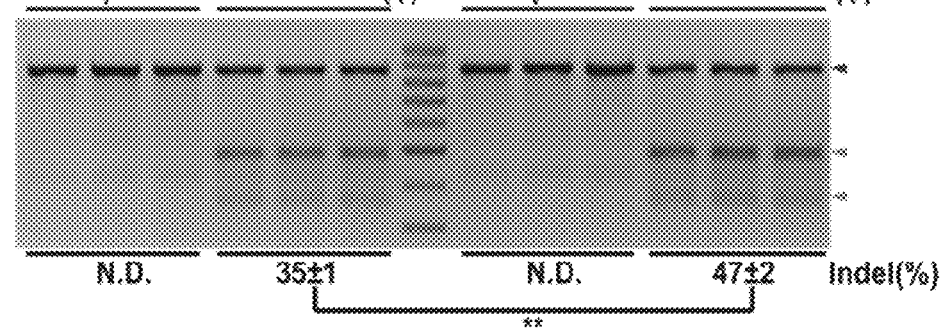
Figure 10:
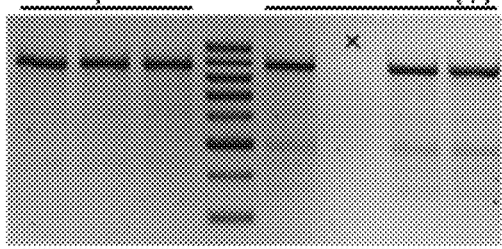
Figure 10:
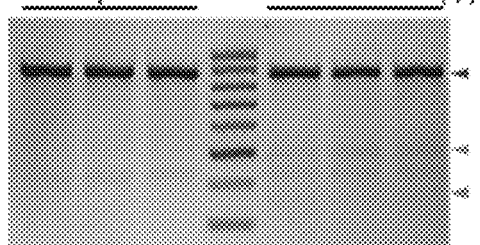
Figure 11A:
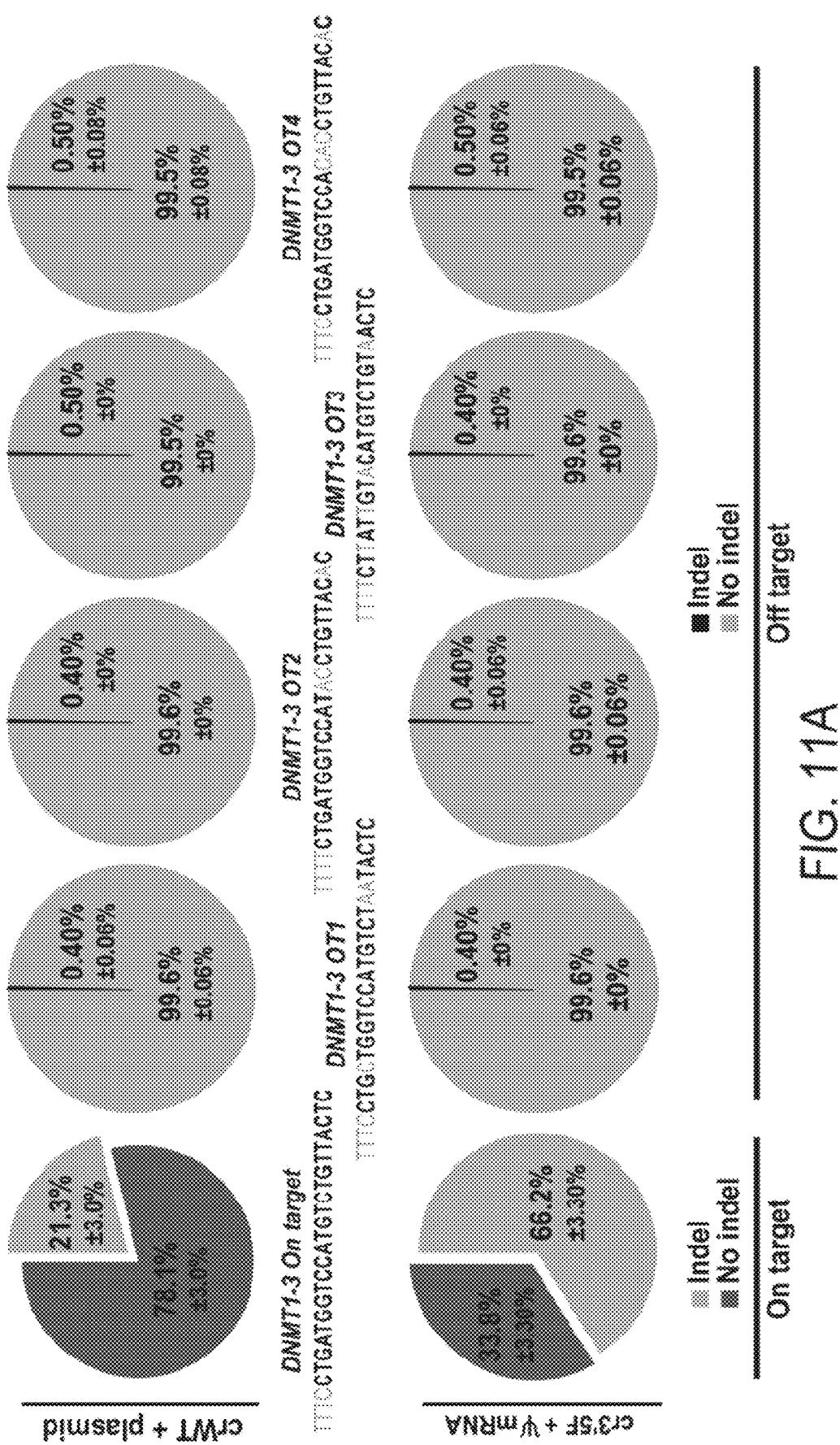
FIGS. 11A-11C. Targeted deep sequencing analysis of on-target and off-target gene cutting using chemically modified crRNA and AsCpf1 mRNA.
Figure 11B:
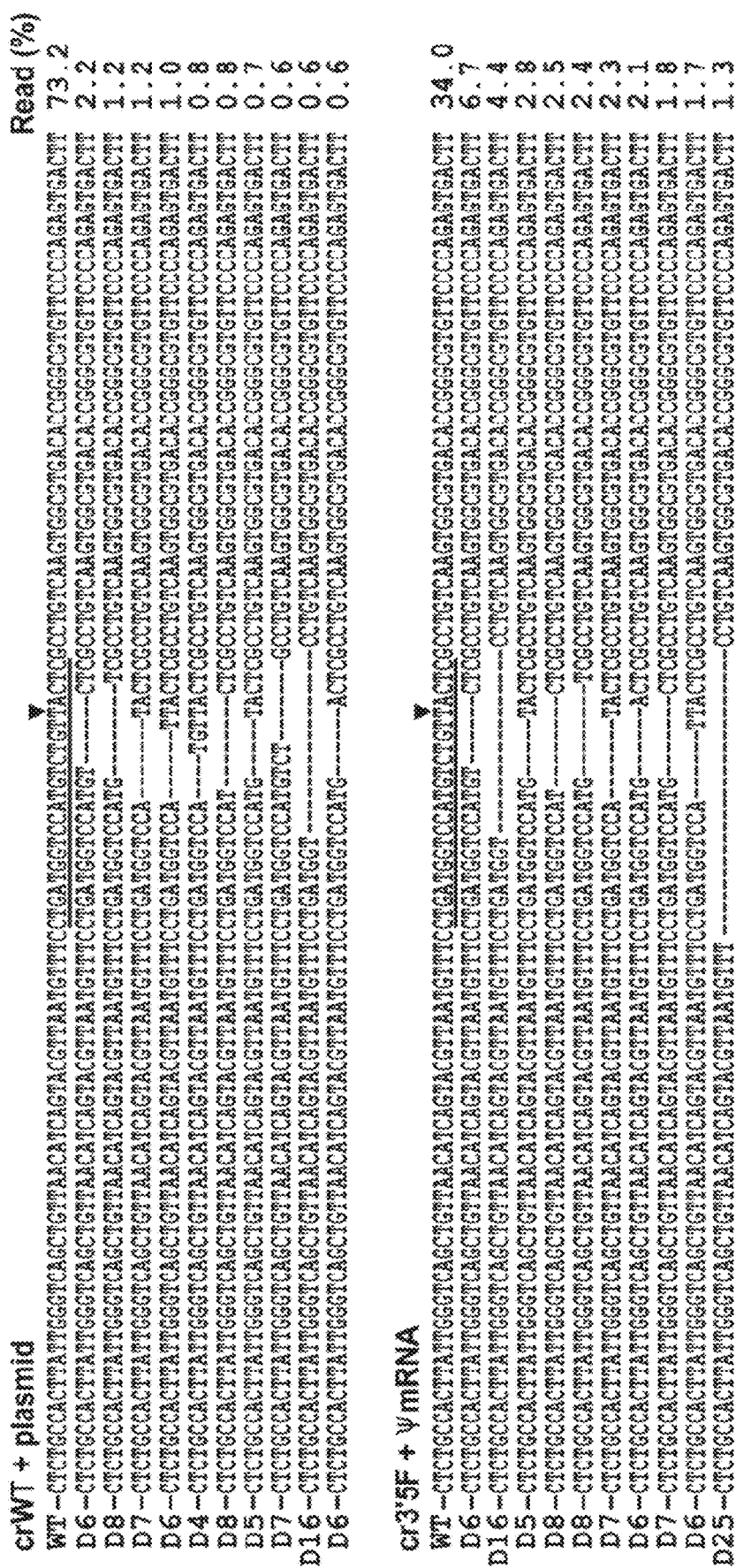
Figure 11C:
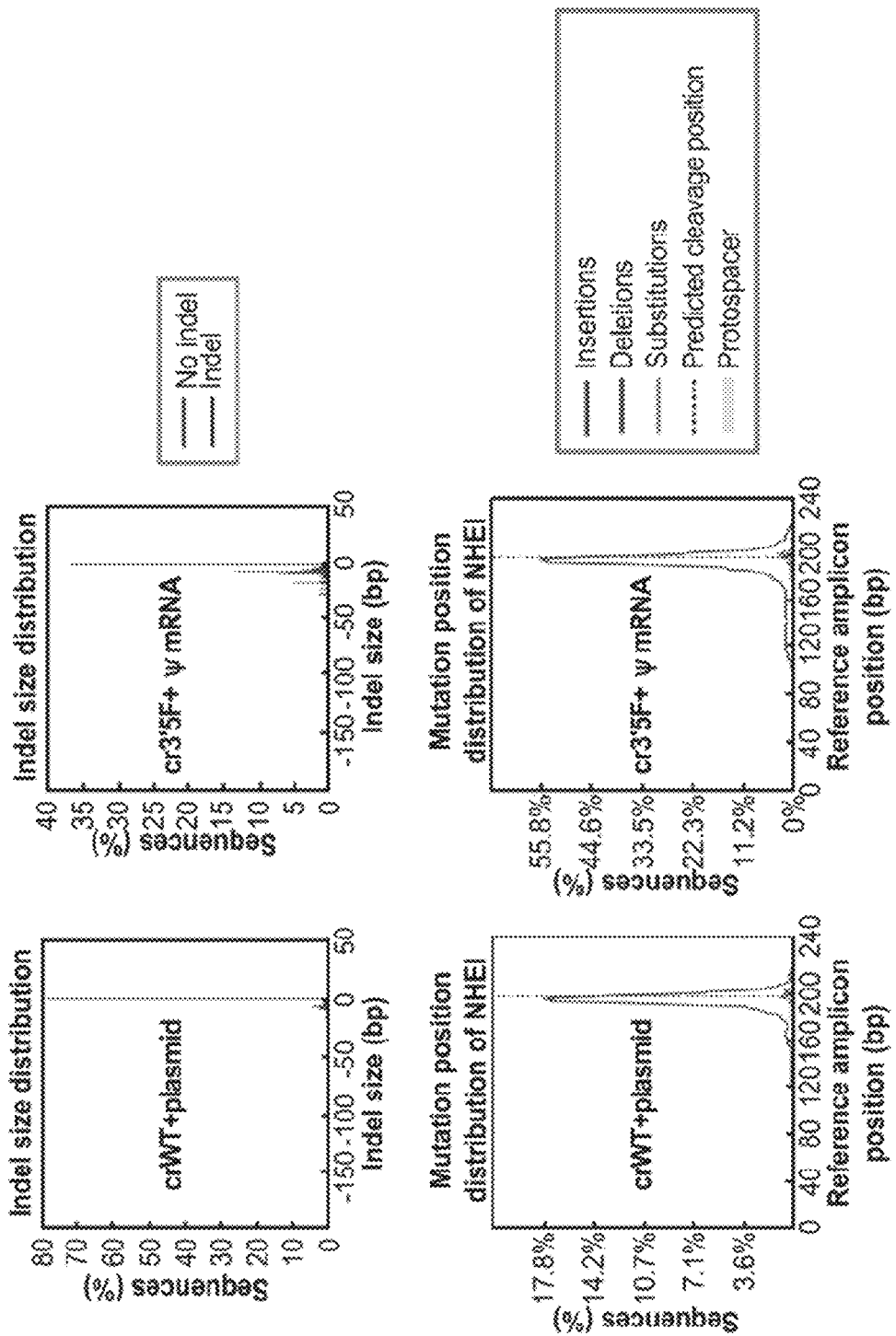
Figure 12:
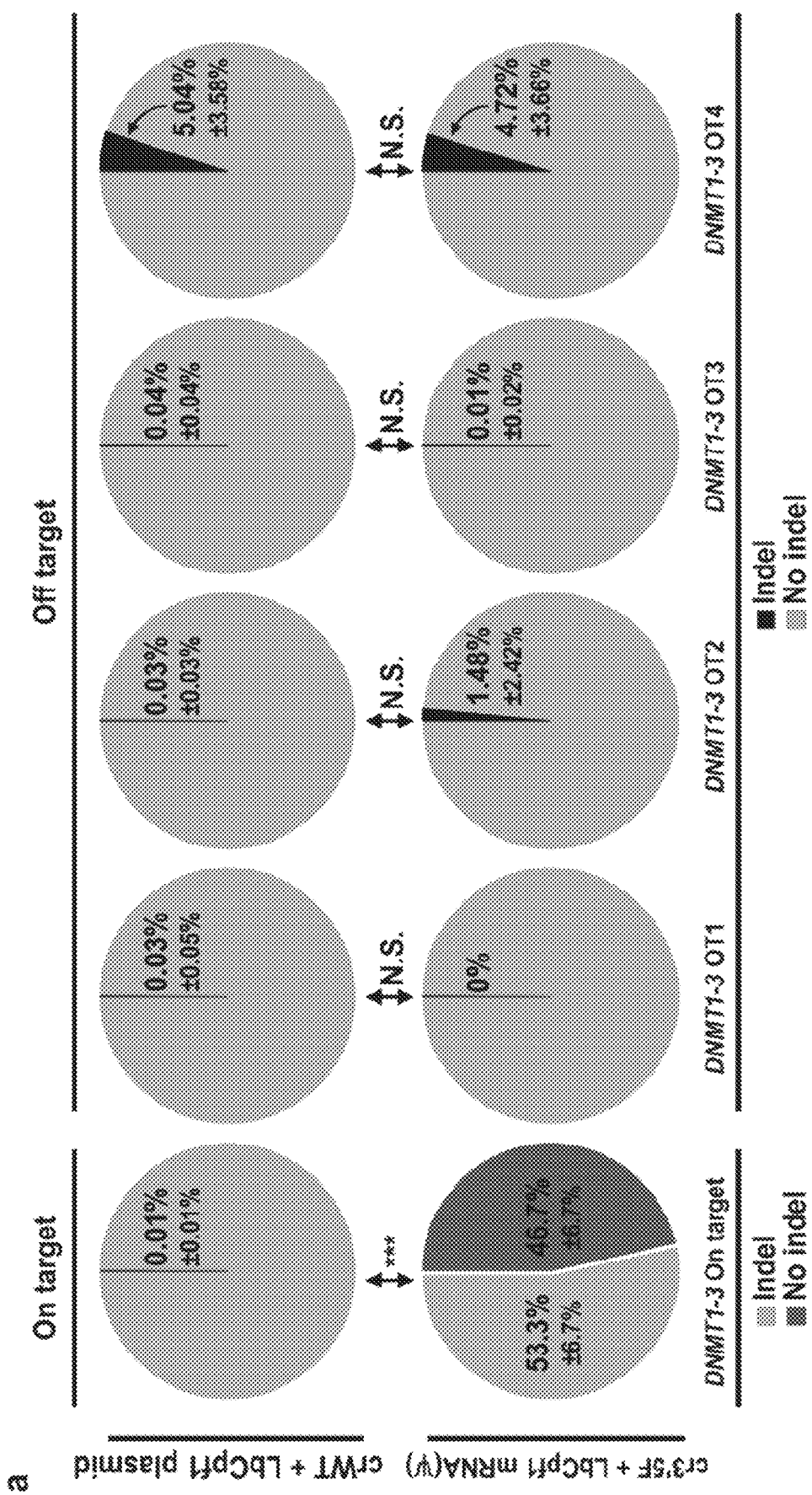
FIG. 12. Targeted deep sequencing analysis of on-target and off-target gene cutting using chemically modified crRNA and LbCpf1 mRNA. (a) Indel at on-target and predicted top four off-target sites analyzed by deep sequencing at genomic on- and off-target locus. Indel was plotted as the mean of three biological replicates. (b) Representative top ten high-frequent on-target mutagenesis aligned to the target site of DNMT1-3 induced by crWT+LbCpf1 plasmid (top) and cr3'5F+Cpf1 mRNA (bottom). The unmodified sequence of DNMT1-3 (SEQ ID NO: 74) was termed as 'WT' at the top. Deletions were marked as dotted lines. Numbers on the left referred to the size of deletions. The read ratio of each mutated site was listed on the right side. (c) Plot of representative mutations (insertions, deletions, and substitutions). Size distribution (top panel) and position distribution (bottom panel) of all reads for crWT+Cpf1 plasmid (left panel) and cr3'5F+Cpf1 mRNA (right panel).
Figure 12:
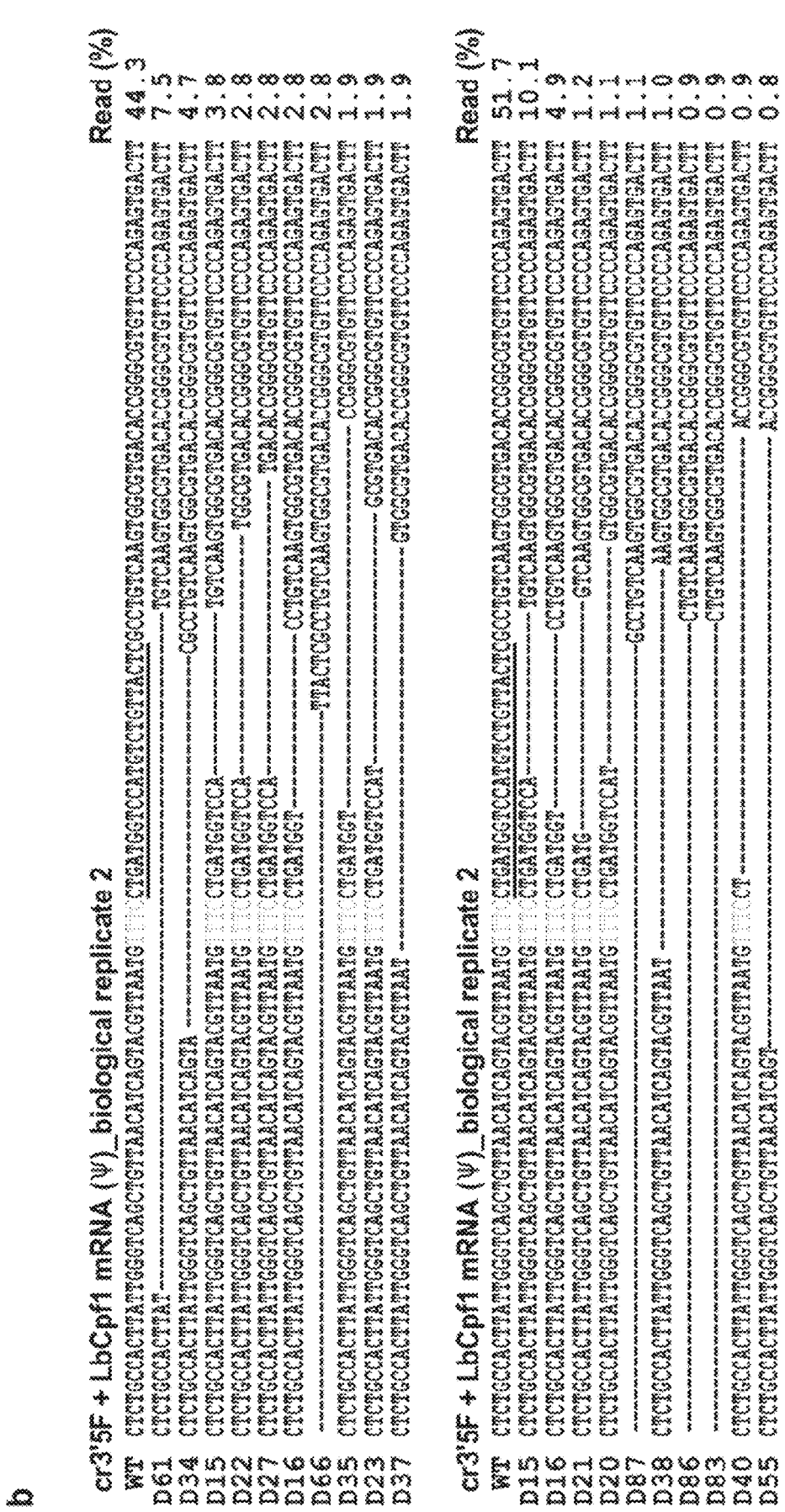
Figure 12:
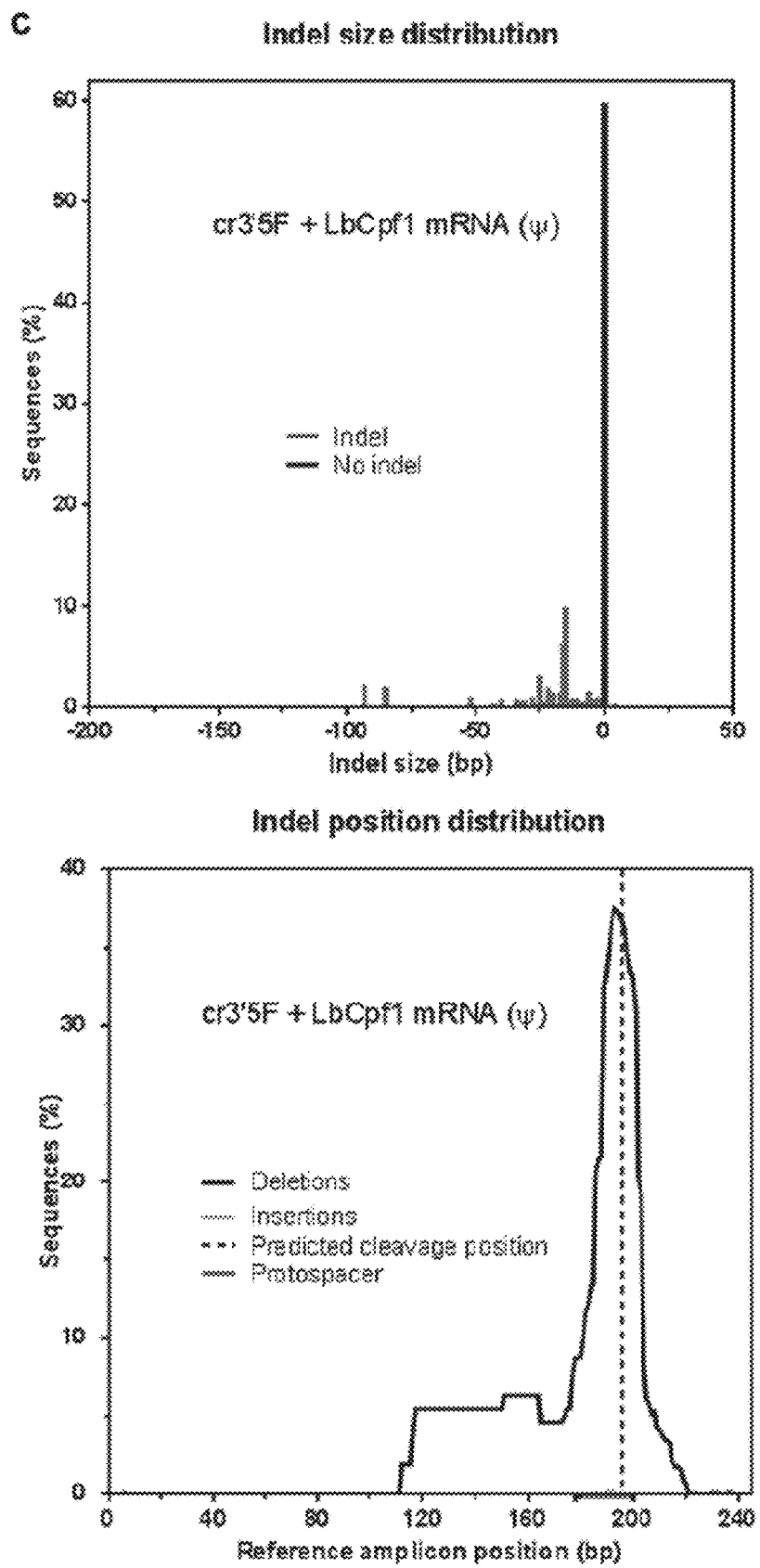
Figure 13:
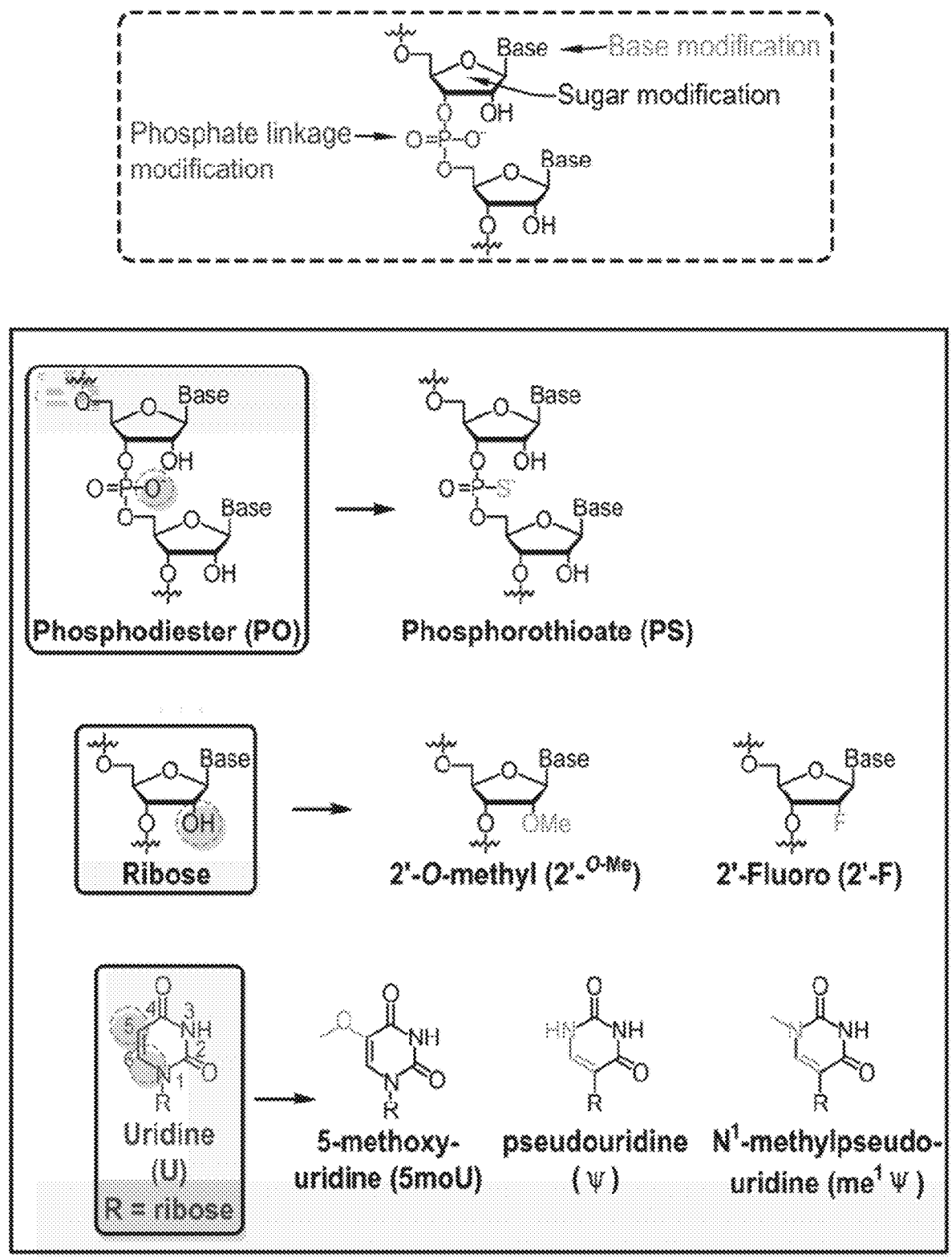
FIG. 13. A panel of chemically modified nucleotides utilized for crRNAs and AsCpf1 mRNA. Box: natural units.

In addition to AsCpf1, we also examined the on-target and off-target effects of LbCpf1 with three biological samples from HEK293T cells used in FIG. 10. As shown in FIG. 12a, Lbcr3'5F+ψ-modified LbCpf1 mRNA caused 46.7% indel compared to minimal effects of LbcrWT+LbCpf1 plasmid. The indel pattern for LbCpf1 was consistent with AsCpf1, while LbCpf1 led to larger fragment deletion than AsCpf1 (FIGS. 12b and 12c). Regarding off-target effects, LbCpf1 exhibited much higher mutagenesis at the position of off-target 4 (OT4) than AsCpf1 under the same condition (FIG. 12a). Similarly, Lbcr3'5F+ψ-modified LbCpf1 mRNA showed comparable off-target effects to that of LbcrWT+LbCpf1 plasmid (FIG. 12a). Taken together, combination of engineered crRNA and Cpf1 mRNA enables us to effectively enhance genome editing efficiency without increasing off-target effects.

In summary, genome editing efficiency and off-targets effects are major challenges for the broad applications of CRISPR systems. To address these issues, an array of crRNA variants including chemically modified crRNAs and pseudoknot rearranged crRNAs were designed, and the structure-activity relationships of crRNAs were elucidated for improved genome editing activity in CRISP-Cpf1 system. In sharp contrast to CRISPR-Cas9, neither phosphorothioate substitutions nor dual-modification at both sides of guide RNA enhanced gene editing efficiency. Moreover, slight modifications at the 5'-handle or seed region severely hampered cleavage activity. Importantly, 2'-F modification at the 3' terminus (cr3'5F) exhibited higher potency compared with wild-type crRNA. Regarding chemically modified Cpf1 mRNA, pseudo-U (ψ) and me$^1$ψ are favorable modifications compared to the mRNA with unmodified nucleotides. Strikingly, combination of cr3'5F and ψ Cpf1 mRNA synergistically improved the gene cutting efficiency, which improved over 3-fold compared to unmodified crRNA (crWT) and plasmid encoding AsCpf1. This phenomena were not only confirmed in three cell lines and two target gene sites, but also observed in another Cpf1 family protein LbCpf1, demonstrating the broad applicability of this chemical strategy. In addition, it was shown that the cross complexation of Cpf1 and its guide RNA: AsCpf1 was able to effectively achieve genome editing in the presence of LbCpf1 crRNA; nevertheless, LbCpf1 in combination with AsCpf1 crRNA completely lost its function. This finding further expands the current understanding of the CRISPR-Cpf1 system. Furthermore, targeted deep sequencing data suggested that combination of cr3'5F and ψ Cpf1 mRNA did not increase the level of off-target effects.

Methods

Synthesis of crRNAs.

The sequences of the crRNA targeting the DNMT1-3 locus:

```
AsCpf1 crRNA:
                                    (SEQ ID NO: 3)
5'-UAAUUUCUACUCUUGUAGAUCU

GAUGGUCCAUGUCUGUUACUC-3';

LbCpf1 crRNA:
                                    (SEQ ID NO: 8)
5'-AAUUUCUACUAAGUGUAGAUCU

GAUGGUCCAUGUCUGUUACUC-3'.
```

The sequence of unmodified crRNA targeting AAVS1 locus:

```
AsCpf1 crRNA:
                                    (SEQ ID NO: 9)
5'-UAAUUUCUACUCUUGUAGAUCU

UACGAUGGAGCCAGAGAGGAU-3'.
```

The sequence of unmodified crRNA targeting FANCF-2 locus:

```
AsCpf1 crRNA:
                                    (SEQ ID NO: 10)
5'-UAAUUUCUACUCUUGUAGAUGU

CGGCAUGGCCCCAUUCGCACG-3'.
```

Unmodified crRNA (crWT) and all other crRNA variants including chemically modified crRNAs, stem loop deleted and inserted crRNAs were synthesized using an automated solid-phase DNA/RNA synthesizer. Chemically modified crRNAs consisted of partial or total chemically modified nucleotides including phosphate linkage (PS), 2'-O-Me, 2'-F modified, unlocked, locked nucleotides as well as their combinations (FIGS. 19 and 20 and FIG. 9a, and FIG. 15). Stem-engineered crRNAs were designed by deleting certain number of Watson-Crick base pairs from the stem duplex or inserting additional paired or unpaired bases into the stem duplex of crWT (FIG. 1c and Supplementary Table 1). Split crRNA (crSplit) was generated by incubating equimolar of relevant RNA sequences listed in FIG. 19 in TE buffer at 95° C. for 30 s, followed by gradient cooling (95-25° C. ramping at 0.1° C./s). Loop engineered crRNAs were designed by employing the loops from other Cpf1 orthologs (FIG. 16a).

The Split crRNA (crSplit) was hybridized by incubating equimolar of relevant RNA sequences listed in FIGS. 19 and 20 in TE buffer at 95° C. for 30 s, followed by gradient cooling (95-25° C. ramping at 0.1° C./s). All crRNAs were purified on denaturing polyacrylamide gels and verified by mass spectrometry (FIGS. 19 and 20, and FIG. 9b).

AsCpf1 Plasmid and mRNAs.

Cpf1 plasmid was a gift from Dr. Feng Zhang. ARCA capped and polyadenylated AsCpf1 mRNA transcripts were purchased from TriLink BioTechnologies (San Diego, CA, USA). For modified mRNAs, uridines were fully substituted with pseudouridine ($\psi$), $N^1$-methylpseudouridine (me$^1\psi$), or 5-methoxyuridine (5moU). For S1228A & $\psi$ modified mRNA, serine 1228 was substituted with alanine and uridines were fully substituted with pseudouridine ($\psi$). These mRNAs were subjected to DNase and phosphatase treatment and silica membrane-based purification for further use. All mRNAs were verified by polyacrylamide gels (FIG. 4).

Co-Delivery AsCpf1 Plasmid/mRNA and crRNA.

HEK-293T cells were cultured in Dulbecco's modified Eagle's medium (Life technologies). Hep3B cells were cultured in Eagle's Minimum Essential Medium (EMEM, ATCC). All medium supplemented with 10% FBS, and both cell lines used in this study were maintained at 37° C. with 5% $CO_2$. After overnight incubation (approximate 60-80% confluence), cells, seeded on 24-well plates at an initial density of approximate 100,000 cells per well were treated with either 500 ng of Cpf1 expression plasmid (transfection with Lipofectamine 3000 according to the protocol provided by Life Technologies) or 500 ng of mRNA (transfection with Lipofectamine 3000). At the same time, crRNAs (38 pmol for DNMT1-3 and AAVS1 locus, and 114 pmol for FANCF-2 locus) were formulated with Lipofectamine 3000 in Opti-MEM I reduced serum medium (Life Technologies) and added to each well following the manufacturer's recommended protocol.

Genomic DNA Purification and PCR Amplification.

Two days post-treatment, cells were washed with PBS. The genomic DNA (gDNA) was then extracted and purified with a DNeasy Blood & Tissue Kit (QIAGEN) following the manufacturer's instructions. Concentrations of gDNA were determined on a Nanodrop 2000. Genomic regions flanking the on-target as well as previously predicted off-target sites off-target sites for T7E1 assay were amplified using 100 ng of purified gDNA template, Q5 high-fidelity DNA polymerase (New England Biolabs) and specific primers (Integrated DNA Technologies, FIG. 20) on a T100 thermal cycler (Bio-Rad).

T7E1 Cleavage Assay.

The PCR products (10 µL) generated using Q5 high-fidelity DNA polymerase were heteroduplexed in hybridization buffer (50 mM NaCl, 10 mM Tris-HCl, 10 mM $MgCl_2$, 1 mM DTT, pH 7.9) (New England Biolabs) by heating to 98° C. for 10 minutes, followed by a 2° C./s ramp down to 85 C, 1 min at 85° C., and a 0.1° C./s ramp down to 25° C. on a T100 thermal cycler (Bio-Rad). Subsequently, the annealed samples were subjected to T7 Endonuclease I (New England Biolabs) digestion for 30 min, separated by a 2% agarose gel and quantitated on ChemiDoc XRS (Bio-Rad) using Quantity One software. The mutation frequency (indel %) was calculated with the following formula: $100 \times (1-(1-\text{fraction cleaved})^{1/2})$.

MiSeq Library Preparation and Targeted Deep Sequencing.

To further characterize on-target and off-target effects, genomic segment (200~300 bp) spanning the sites of interest were first amplified using sequencing primers with overhang adapter sequences (FIG. 21) in the first round of PCR for 25 cycles. After purification, the second limited-cycle PCR amplification (8 cycles) was performed using the Nextera XT Index Kit (Illumina) to attach multiplexing indices and Illumina P5/P7 sequencing adapters (Tables 2 and 3) to the first round PCR product. Next, libraries were normalized and pooled, and subjected to 2×300 paired-end sequencing on an Illumina MiSeq system. The raw deep sequencing data from MiSeq were analyzed with a bioinformatic tool, CRISPResso, with specific parameters.

REFERENCES CITED IN THIS EXAMPLE

1. Makarova, K. S. et al. Evolution and classification of the CRISPR-Cas systems. *Nat Rev Microbiol* 9, 467-477 (2011).
2. Bosley, K. S. et al. CRISPR germline engineering—the community speaks. *Nat Biotechnol* 33, 478-486 (2015).
3. Jinek, M. et al. A programmable dual-RNA-guided DNA endonuclease in adaptive bacterial immunity. *Science* 337, 816-821 (2012).
4. Cong, L. et al. Multiplex genome engineering using CRISPR/Cas systems. *Science* 339, 819-823 (2013).
5. *Mali*, P. et al. RNA-guided human genome engineering via Cas9. *Science* 339, 823-826 (2013).
6. Zetsche, B. et al. Cpf1 Is a Single RNA-Guided Endonuclease of a Class 2 CRISPR-Cas System. *Cell* 163, 759-771 (2015).
7. Dong, D. et al. The crystal structure of Cpf1 in complex with CRISPR RNA. *Nature* 532, 522-526 (2016).
8. Fonfara, I., Richter, H., Bratovic, M., Le Rhun, A. & Charpentier, E. The CRISPR-associated DNA-cleaving enzyme Cpf1 also processes precursor CRISPR RNA. *Nature* 532, 517-521 (2016).
9. Yamano, T. et al. Crystal Structure of Cpf1 in Complex with Guide RNA and Target DNA. *Cell* (2016).
10. Kleinstiver, B. P. et al. Genome-wide specificities of CRISPR-Cas Cpf1 nucleases in human cells. *Nat Biotechnol* 34, 869-874 (2016).
11. Kim, D. et al. Genome-wide analysis reveals specificities of Cpf1 endonucleases in human cells. *Nat Biotechnol* 34, 863-868 (2016).
12. Slaymaker, I. M. et al. Rationally engineered Cas9 nucleases with improved specificity. *Science* 351, 84-88 (2016).
13. Kleinstiver, B. P. et al. High-fidelity CRISPR-Cas9 nucleases with no detectable genome-wide off-target effects. Nature 529, 490-+(2016).
14. Hendel, A. et al. Chemically modified guide RNAs enhance CRISPR-Cas genome editing in human primary cells. *Nat Biotechnol* 33, 985-989 (2015).
15. Rahdar, M. et al. Synthetic CRISPR RNA-Cas9-guided genome editing in human cells. *Proc Natl Acad Sci USA* 112, E7110-7117 (2015).
16. Chen, B. et al. Dynamic imaging of genomic loci in living human cells by an optimized CRISPR/Cas system. *Cell* 155, 1479-1491 (2013).
17. Dang, Y. et al. Optimizing sgRNA structure to improve CRISPR-Cas9 knockout efficiency. *Genome Biol* 16, 280 (2015).
18. Watts, J. K., Deleavey, G. F. & Damha, M. J. Chemically modified siRNA: tools and applications. *Drug Discov Today* 13, 842-855 (2008).

19. Kariko, K., Muramatsu, H., Keller, J. M. & Weissman, D. Increased erythropoiesis in mice injected with submicrogram quantities of pseudouridine-containing mRNA encoding erythropoietin. *Mol Ther* 20, 948-953 (2012).
20. Andries, O. et al. N(1)-methylpseudouridine-incorporated mRNA outperforms pseudouridine-incorporated mRNA by providing enhanced protein expression and reduced immunogenicity in mammalian cell lines and mice. *J Control Release* 217, 337-344 (2015).
21. Li, B., Luo, X. & Dong, Y. Effects of Chemically Modified Messenger RNA on Protein Expression. *Bioconjug Chem* (2016).
22. Pinello, L. et al. Analyzing CRISPR genome-editing experiments with CRISPResso. *Nat Biotechnol* 34, 695-697 (2016).

Modification pattern and mass spectrometry data of crRNAs used are shown in Table 1 and FIG. 19.

TABLE 2

AsCpf1: A list of index sequences used for the 2$^{nd}$ round of PCR of targeted deep sequencing.

| Index No. | Sample name | Index 1 | Sequence | Index 2 | Sequence |
|---|---|---|---|---|---|
| 1 | AscrWT/AsCpf1 plasmid_1_OT1 | N701 | TAAGGCGA | N517 | GCGTAAGA |
| 2 | AscrWT/AsCpf1 plasmid_2_OT1 | N701 | TAAGGCGA | N502 | CTCTCTAT |
| 3 | AscrWT/AsCpf1 plasmid_3_OT1 | N701 | TAAGGCGA | N503 | TATCCTCT |
| 4 | AscrWT/AsCpf1 plasmid_1_OT2 | N701 | TAAGGCGA | N504 | AGAGTAGA |
| 5 | AscrWT/AsCpf1 plasmid_2_OT2 | N701 | TAAGGCGA | N505 | GTAAGGAG |
| 6 | AscrWT/AsCpf1 plasmid_3_OT2 | N701 | TAAGGCGA | N506 | ACTGCATA |
| 7 | AscrWT/AsCpf1 plasmid_1_OT3 | N701 | TAAGGCGA | N507 | AAGGAGTA |
| 8 | AscrWT/AsCpf1 plasmid_2_OT3 | N701 | TAAGGCGA | N508 | CTAAGCCT |
| 9 | AscrWT/AsCpf1 plasmid_3_OT3 | N702 | CGTACTAG | N517 | GCGTAAGA |
| 10 | AscrWT/AsCpf1 plasmid_1_OT4 | N702 | CGTACTAG | N502 | CTCTCTAT |
| 11 | AscrWT/AsCpf1 plasmid_2_OT4 | N702 | CGTACTAG | N503 | TATCCTCT |
| 12 | AscrWT/AsCpf1 plasmid_3_OT4 | N702 | CGTACTAG | N504 | AGAGTAGA |
| 13 | Ascr3'5F/AsCpf1 ψ mRNA_1_OT1 | N702 | CGTACTAG | N505 | GTAAGGAG |
| 14 | Ascr3'5F/AsCpf1 ψ mRNA_2_OT1 | N702 | CGTACTAG | N506 | ACTGCATA |
| 15 | Ascr3'5F/AsCpf1 ψ mRNA_3_OT1 | N702 | CGTACTAG | N507 | AAGGAGTA |
| 16 | Ascr3'5F/AsCpf1 ψ mRNA_1_OT2 | N702 | CGTACTAG | N508 | CTAAGCCT |
| 17 | Ascr3'5F/AsCpf1 ψ mRNA_2_OT2 | N703 | AGGCAGAA | N517 | GCGTAAGA |
| 18 | Ascr3'5F/AsCpf1 ψ mRNA_3_OT2 | N703 | AGGCAGAA | N502 | CTCTCTAT |
| 19 | Ascr3'5F/AsCpf1 ψ mRNA_1_OT3 | N703 | AGGCAGAA | N503 | TATCCTCT |
| 20 | Ascr3'5F/AsCpf1 mRNA_2_OT3 | N703 | AGGCAGAA | N504 | AGAGTAGA |
| 21 | Ascr3'5F/AsCpf1 mRNA_3_OT3 | N703 | AGGCAGAA | N505 | GTAAGGAG |
| 22 | Ascr3'5F/AsCpf1 ψ mRNA_1_OT4 | N703 | AGGCAGAA | N506 | ACTGCATA |
| 23 | Ascr3'5F/AsCpf1 ψ mRNA_2_OT4 | N703 | AGGCAGAA | N507 | AAGGAGTA |
| 24 | Ascr3'5F/AsCpf1 ψ mRNA_3_OT4 | N703 | AGGCAGAA | N508 | CTAAGCCT |
| 25 | AscrWT/AsCpf1 plasmid_1_On target | N704 | TCCTGAGC | N517 | GCGTAAGA |
| 26 | AscrWT/AsCpf1 plasmid_2_On target | N704 | TCCTGAGC | N502 | CTCTCTAT |
| 27 | AscrWT/AsCpf1 plasmid_3_On target | N704 | TCCTGAGC | N503 | TATCCTCT |
| 28 | Ascr3'5F/AsCpf1 ψ mRNA_1_On target | N704 | TCCTGAGC | N504 | AGAGTAGA |

TABLE 2-continued

AsCpf1: A list of index sequences used for the 2$^{nd}$ round of PCR of targeted deep sequencing.

| Index No. | Sample name | Index 1 | Sequence | Index 2 | Sequence |
|---|---|---|---|---|---|
| 29 | Ascr3'5F/AsCpf1 ψ mRNA_2_On target | N704 | TCCTGAGC | N505 | GTAAGGAG |
| 30 | Ascr3'5F/AsCpf1 ψ mRNA_3_On target | N704 | TCCTGAGC | N506 | ACTGCATA |

TABLE 3

LbCpf1: A list of index sequences used for the 2$^{nd}$ round of PCR of targeted deep sequencing.

| Index No. | Sample name | Index 1 | Sequence | Index 2 | Sequence |
|---|---|---|---|---|---|
| 1 | LbcrWT/LbCpf1 plasmid_1_OT1 | N701 | TAAGGCGA | N517 | GCGTAAGA |
| 2 | LbcrWT/LbCpf1 plasmid_2_OT1 | N701 | TAAGGCGA | N502 | CTCTCTAT |
| 3 | LbcrWT/LbCpf1 plasmid_3_OT1 | N701 | TAAGGCGA | N503 | TATCCTCT |
| 4 | LbcrWT/LbCpf1 plasmid_1_OT2 | N701 | TAAGGCGA | N504 | AGAGTAGA |
| 5 | LbcrWT/LbCpf1 plasmid_2_OT2 | N701 | TAAGGCGA | N505 | GTAAGGAG |
| 6 | LbcrWT/LbCpf1 plasmid_3_OT2 | N701 | TAAGGCGA | N506 | ACTGCATA |
| 7 | LbcrWT/LbCpf1 plasmid_1_OT3 | N701 | TAAGGCGA | N507 | AAGGAGTA |
| 8 | LbcrWT/LbCpf1 plasmid_2_OT3 | N701 | TAAGGCGA | N508 | CTAAGCCT |
| 9 | LbcrWT/LbCpf1 plasmid_3_OT3 | N702 | CGTACTAG | N517 | GCGTAAGA |
| 10 | LbcrWT/LbCpf1 plasmid_1_OT4 | N702 | CGTACTAG | N502 | CTCTCTAT |
| 11 | LbcrWT/LbCpf1 plasmid_2_OT4 | N702 | CGTACTAG | N503 | TATCCTCT |
| 12 | LbcrWT/LbCpf1 plasmid_3_OT4 | N702 | CGTACTAG | N504 | AGAGTAGA |
| 13 | Lbcr3'5F/LbCpf1 ψ mRNA_1_OT1 | N702 | CGTACTAG | N505 | GTAAGGAG |
| 14 | Lbcr3'5F/LbCpf1 ψ mRNA_2_OT1 | N702 | CGTACTAG | N506 | ACTGCATA |
| 15 | Lbcr3'5F/LbCpf1 ψ mRNA_3_OT1 | N702 | CGTACTAG | N507 | AAGGAGTA |
| 16 | Lbcr3'5F/LbCpf1 ψ mRNA_1_OT2 | N702 | CGTACTAG | N508 | CTAAGCCT |
| 17 | Lbcr3'5F/LbCpf1 ψ mRNA_2_OT2 | N703 | AGGCAGAA | N517 | GCGTAAGA |
| 18 | Lbcr3'5F/LbCpf1 ψ mRNA_3_OT2 | N703 | AGGCAGAA | N502 | CTCTCTAT |
| 19 | Lbcr3'5F/LbCpf1 ψ mRNA_1_OT3 | N703 | AGGCAGAA | N503 | TATCCTCT |
| 20 | Lbcr3'5F/LbCpf1 ψ mRNA_2_OT3 | N703 | AGGCAGAA | N504 | AGAGTAGA |
| 21 | Lbcr3'5F/LbCpf1 ψ mRNA_3_OT3 | N703 | AGGCAGAA | N505 | GTAAGGAG |
| 22 | Lbcr3'5F/LbCpf1 ψ mRNA_1_OT4 | N703 | AGGCAGAA | N506 | ACTGCATA |
| 23 | Lbcr3'5F/LbCpf1 ψ mRNA_2_OT4 | N703 | AGGCAGAA | N507 | AAGGAGTA |
| 24 | Lbcr3'5F/LbCpf1 ψ mRNA_3_OT4 | N703 | AGGCAGAA | N508 | CTAAGCCT |
| 25 | LbcrWT/LbCpf1 plasmid_1_On target | N704 | TCCTGAGC | N517 | GCGTAAGA |
| 26 | LbcrWT/LbCpf1 plasmid_2_On target | N704 | TCCTGAGC | N502 | CTCTCTAT |
| 27 | LbcrWT/LbCpf1 plasmid_3_On target | N704 | TCCTGAGC | N503 | TATCCTCT |
| 28 | Lbcr3'5F/LbCpf1 ψ mRNA_1_On target | N704 | TCCTGAGC | N504 | AGAGTAGA |

TABLE 3-continued

LbCpf1: A list of index sequences used for the 2$^{nd}$ round of PCR of targeted deep sequencing.

| Index No. | Sample name | Index 1 | Sequence | Index 2 | Sequence |
|---|---|---|---|---|---|
| 29 | Lbcr3'5F/LbCpf1 ψ mRNA_2_On target | N704 | TCCTGAGC | N505 | GTAAGGAG |
| 30 | Lbcr3'5F/LbCpf1 ψ mRNA_3_On target | N704 | TCCTGAGC | N506 | ACTGCATA |
| 31 | Untreated_1_OT1 | N705 | GGACTCCT | N517 | GCGTAAGA |
| 32 | Untreated_2_OT1 | N705 | GGACTCCT | N502 | CTCTCTAT |
| 33 | Untreated_3_OT1 | N705 | GGACTCCT | N503 | TATCCTCT |
| 34 | Untreated_1_On target | N705 | GGACTCCT | N504 | AGAGTAGA |
| 35 | Untreated_2_On target | N705 | GGACTCCT | N505 | GTAAGGAG |
| 36 | Untreated_3_On target | N705 | GGACTCCT | N506 | ACTGCATA |

Amplicons Used for Targeted MiSeq Analysis.

DNMT1-3 on-target sense (245 bp)
>NC_000007.14 Homo sapiens chromosome 7, GRCh38.p7 Primary Assembly
(SEQ ID NO: 105)
AAGTCACTCTGGGGAACACGCCCGGTGTCACGCCACTTGACAGGCGA

GTAACAGACATGGACCATCAGGAAACATTAACGTACTGATGTTAACA

GCTGACCCAATAAGTGGCAGAGTGCTAAGGGAACGTTCACGGAGACT

GAACACTCCTCAAACGGTCCCCAGAGGGTTCTAGACCCAGAGGCTCA

AGTGAGCAGCTGAGGCAGGTGCCTGCTGAGCCAAATTCACCGAGCAG

GAGTGAGGGA

DNMT1-3 off-target 1 (OT1, 243 bp)
>NC_000007.14 Homo sapiens chromosome 7, GRCh38.p7 Primary Assembly
(SEQ ID NO: 106)
GGGAGGGGGTCAGCATGAAAGGAGCAGTGTGAAATGGACAATTCACA

CACCTTCCATGTTTCTCAACAATGTCAGTCCCTGCTGTTGCCACGGC

CGCTATGGTCTTCTCACAACAAGAAGAGTATTAGACATGGACCAGCA

GGAAAGCACACGTTCACAGGCACGTGCCCATGCTCACAAACACACAC

ATGTGTGCATGCACACATGCACACTCCCTACACCCCTTCTCCACGCC

CAAAAGGT

DNMT1-3 off-target 2 (OT2, 230 bp)
>NC_000016.10 Homo sapiens chromosome 16, GRCh38.p7 Primary Assembly
(SEQ ID NO: 107)
CTCCCCCACCCCCTAGGAAAGTCAGGTGATGGTTCAGCAAGTATCAC

ATCGCCTCTGTAAAGGTGATAAACTGGCTGCCAGGGCCAGGGAGAGG

CCATTTTCTGATGGTCCATACCTGTTACACTAAAGTGTTAATTGAAT

GCAGATGCCAGGGAGGAGCAACTTCCAGGGCATGTGCATCAAGAGAC

AAAACAGTGGAATATGTCCTGGGGACACTCCACCAGAAAGGG

DNMT1-3 off-target (OT3, 226 bp)
>NC_000011.10 Homo sapiens chromosome 11, GRCh38.p7 Primary Assembly
(SEQ ID NO: 108)
AGACGACCTTAGATGGAGTGTTGTGTATTTCAAACAGAGTTACCATT

GTGCTTTATCGTGATCAGTCCCCTTCTTGACACGTGAGAGTTACAGA

CATGTACAATAAGAAAATTAGGAAAATTTCGGACAAAAACATCTGAA

TATATAAGAATTTGAATTGAATTTCCTATCTCTCTTATTAAAAACAA

ACATAAACCTTAAGCCCAAAACCTCTCCTATACCTTCA

DNMT1-3 off-target 4 (OT2, 230 bp)
>NC_000023.11 Homo sapiens chromosome X, GRCh38.p7 Primary Assembly
(SEQ ID NO: 109)
TGCCAGTGGAAGGAGGGAGTGTTACAGGTAGTTAAGCAGGCATGAGC

TGGGCTGGAGAGGGCTGTCCTCCACCCACTAGGAATGTCAGGTGATG

GCTCAGCAATTATCACATTGACTCTCTAAAAGTGACAAATTGGCAGC

CAGTGCCAGGGAGAAGCCATTTCCTGATGGTCCACACCTGTTACACT

AAAGGGTTAATTGAATGCAGATGCCAGGGAGAAGCAACTTCCTGGGC

A

Sequencing Data Analysis.

CRISPResso was utilized to analyze the deep sequencing data. 22 nt (T rather than U) from 3' of the PAM (TTTN) is designated as crRNA sequences. The amplicon containing the PAM was used for alignment. To quantify mutation events and avoid false positives, the reading size is set up as 10 (10 nt before and after each side of the predicted cleavage site). Minimum average reading quality (phred33 scale) and minimum single bp quality (phred33 scale) is greater than 30 and 20 (recommended values), respectively. Default values were used for other parameters.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A genome editing system having enhanced gene editing efficiency comprising:
   a) a guide RNA that hybridizes with a target sequence of a DNA molecule in a eukaryotic cell that contains the DNA molecule, and
   b) an mRNA encoding a CRISPR from *Prevotella* and *Francisella* 1 ("Cpf1") protein;
   wherein the guide RNA comprises five 2'fluoro (2'F) ribose at the 3'termini (cr3'5), and wherein the mRNA encoding the Cpf1 protein is fully substituted with pseudouridine (Ψ).

2. The system of claim 1, wherein the Ψ-substituted mRNA encoding a Cpf1 protein confers increased Cpf1 protein levels as compared to a corresponding mRNA encoding a Cpf1 protein not having a chemically modified nucleotide.

3. The system of claim 1, wherein the Ψ-substituted mRNA encoding a Cpf1 protein confers increased Cpf1 nuclease activity as compared to a corresponding mRNA encoding a Cpf1 protein not having a chemically modified nucleotide.

4. The system of claim 1, wherein the Ψ-substituted mRNA encoding a Cpf1 protein confers reduced toxicity as compared to a corresponding mRNA encoding a Cpf1 protein not having a chemically modified nucleotide.

5. A genome editing system having enhanced gene editing efficiency comprising:
  a) a guide RNA that hybridizes with a target sequence of a DNA molecule in a eukaryotic cell that contains the DNA molecule, and
  b) a DNA vector comprising a regulatory element operable in a eukaryotic cell operably linked to a nucleotide sequence encoding a CRISPR from *Prevotella* and *Francisella* 1 ("Cpf1") protein; or an mRNA encoding a Cpf1 protein, wherein the nucleotide sequence encoding a Cpf1 protein or mRNA encoding a Cpf1 protein is fully substituted with pseudouridine (Ψ);
  wherein the guide RNA comprises five 2'fluoro (2'F) ribose at the 3'termini (cr3'5), and
  wherein the guide RNA hybridizes with the target sequence and the Cpf1 protein cleaves the DNA molecule.

6. A genome editing system having enhanced gene editing efficiency comprising:
  a) an engineered guide RNA that hybridizes with a target sequence of a DNA molecule in a eukaryotic cell that contains the DNA molecule, and
  b) a DNA vector comprising a regulatory element operable in a eukaryotic cell operably linked to a nucleotide sequence encoding a CRISPR from *Prevotella* and *Francisella* 1 ("Cpf1") protein; or an mRNA encoding a Cpf1 protein, wherein the nucleotide sequence encoding a Cpf1 protein or mRNA encoding a Cpf1 protein is fully substituted with pseudouridine (Ψ);
  wherein the engineered guide RNA comprises at least one nucleotide insertion or deletion, and wherein the engineered guide RNA further comprises five 2'fluoro (2'F) ribose at the 3'termini (cr3'5).

* * * * *

SEQUENCE LISTING

```
<160> NUMBER OF SEQ ID NOS: 109

<210> SEQ ID NO 1
<211> LENGTH: 4020
<212> TYPE: DNA
<213> ORGANISM: Artificial Sequence
<220> FEATURE:
<223> OTHER INFORMATION: synthetic construct

<400> SEQUENCE: 1 atggcccaa agaagaagcg aaggtcggt atccacggag tcccagcagc cacacagttc    60
gagggcttta ccaacctgta tcaggtgagc aagacactgc ggtttgagct gatcccacag   120
ggcaagaccc tgaagcacat ccaggagcag ggcttcatcg aggaggacaa ggcccgcaat   180
gatcactaca aggagctgaa gcccatcatc gatcggatct acaagaccta tgccgaccag   240
tgcctgcagc tggtgcagct ggattgggag aacctgagcg ccgccatcga ctcctataga   300
aaggagaaaa ccgaggagac aaggaacgcc ctgatcgagg agcaggccac atatcgcaat   360
gccatccacg actacttcat cggccggaca gacaacctga ccgatgccat caataagaga   420
cacgccgaga tctacaaggg cctgttcaag gccgagctgt taatggcaa ggtgctgaag   480 cagctgggca ccgtgaccac aaccgagcac gagaacgccc tgctgcggag cttcgacaag   540
tttacaacct acttctccgg cttttatgag aacaggaaga acgtgttcag cgccgaggat   600
atcagcacag ccatcccaca ccgcatcgtg caggacaact ccccaagtt taaggagaat   660 tgtcacatct tcacacgcct gatcaccgcc gtgcccagcc tgcgggagca ctttgagaac   720
gtgaagaagg ccatcggcat cttcgtgagc acctccatcg aggaggtgtt ttccttccct   780 tttataacc agctgctgac acagacccag atcgacctgt ataaccagct gctgggagga   840
atctctcggg aggcaggcac cgagaagatc aagggcctga acgaggtgct gaatctggcc   900
atccagaaga tgatgagac agcccacatc atcgcctccc tgccacacag attcatcccc   960 ctgttaagc agatcctgtc cgataggaac accctgtctt tcatcctgga ggagtttaag  1020
agcgacgagg aagtgatcca gtccttctgc aagtacaaga cactgctgag aaacgagaac  1080
gtgctggaga cagccgaggc cctgttaac gagctgaaca gcatcgacct gacacacatc  1140
ttcatcagcc acaagaagct ggagacaatc agcagcgccc tgtgcgacca ctgggataca  1200
ctgaggaatg ccctgtatga gcggagaatc tccgagctga caggcaagat caccaagtct  1260
gccaaggaga aggtgcagcg cagcctgaag cacgaggata tcaacctgca ggagatcatc  1320
tctgccgcag gcaaggagct gagcgaggcc ttcaagcaga aaaccagcga gatcctgtcc  1380
cacgcacacg ccgccctgga tcagccactg cctacaaccc tgaagaagca ggaggagaag  1440
gagatcctga agtctcagct ggacagcctg ctgggcctgt accacctgct ggactggttt  1500
gccgtggatg agtccaacga ggtggaccc gagttctctg ccggctgac cggcatcaag  1560 ctggagatgg agccttctct gagcttctac aacaaggcca gaattatgc caccaagaag  1620 ccctactccg tggagaagtt caagctgaac tttcagatgc ctacactgcc ctctggctgg  1680
gacgtgaata aggagaagaa caatggcgcc atcctgtttg tgaagaacgg cctgtactat  1740
ctgggcatca tgccaaagca agggcagg tataaggccc tgagcttcga gcccacagag  1800 aaaccagcg agggctttga taagatgtac tatgactact cccctgatgc cgccaagatg  1860
```

```
atcccaaagt gcagcaccca gctgaaggcc gtgacagccc actttcagac ccacacaacc    1920
cccatcctgc tgtccaacaa tttcatcgag cctctggaga tcacaaagga gatctacgac    1980
ctgaacaatc ctgagaagga gccaaagaag tttcagacag cctacgccaa gaaaaccggc    2040
gaccagaagg gctacagaga ggccctgtgc aagtggatcg acttcacaag ggattttctg    2100
tccaagtata ccaagacaac ctctatcgat ctgtctagcc tgcggccatc ctctcagtat    2160
aaggacctgg gcgagtacta tgccgagctg aatcccctgc tgtaccacat cagcttccag    2220
agaatcgccg agaaggagat catggatgcc gtggagacag caagctgta cctgttccag    2280
atctataaca aggactttgc caagggccac cacggcaagc ctaatctgca cacactgtat    2340
tggaccggcc tgttttctcc agagaacctg ccaagacaa gcatcaagct gaatggccag    2400
gccgagctgt ctaccgccc taagtccagg atgaagagga tggcacaccg gctgggagag    2460
aagatgctga caagaagct gaaggatcag aaaaccccaa tccccgacac cctgtaccag    2520
gagctgtacg actatgtgaa tcacagactg tcccacgacc tgtctgatga ggccagggcc    2580
ctgctgccca cgtgatcac caaggaggtg tctcacgaga tcatcaagga taggcgcttt    2640
accagcgaca agttcttttt ccacgtgcct atcacactga actatcaggc cgccaattcc    2700
ccatctaagt tcaaccagag ggtgaatgcc tacctgaagg agcaccccga cacctatc    2760
atcggcatcg atcggggcga gagaaacctg atctatatca cagtgatcga ctccaccggc    2820
aagatcctgg agcagcggag cctgaacacc atccagcagt ttgattacca agaagaagctg    2880
gacaacaggg agaaggagag ggtggcagca aggcaggcct ggtctgtggt gggcacaatc    2940
aaggatctga gcagggcta tctgagccag gtcatccacg agatcgtgga cctgatgatc    3000
cactaccagg ccgtggtggt gctggagaac ctgaatttcg gctttaagag caagaggacc    3060
ggcatcgccg agaaggccgt gtaccagcag ttcgagaaga tgctgatcga taagctgaat    3120
tgcctggtgc tgaaggacta tccagcagag aaagtgggag cgtgctgaa cccataccag    3180
ctgacagacc agttcacctc ctttgccaag atgggcaccc agtctggctt cctgttttac    3240
gtgcctgccc catatacatc taagatcgat cccctgaccg gcttcgtgga ccccttcgtg    3300
tggaaaacca tcaagaatca cgagagccgc aagcacttcc tggagggctt cgactttctg    3360
cactacgacg tgaaaaccgg cgacttcatc ctgcacttta agatgaacag aaatctgtcc    3420
ttccagaggg gcctgcccgg ctttatgcct gcatgggata tcgtgttcga gaagaacgag    3480
acacagtttg acgccaaggg caccccttc atcgccggca agagaatcgt gccagtgatc    3540
gagaatcaca gattcaccgg cagataccgg gacctgtatc ctgccaacga gctgatcgcc    3600
ctgctggagg agaagggcat cgtgttcagg gatggctcca acatcctgcc aaagctgctg    3660
gagaatgacg attctcacgc catcgacacc atggtggccc tgatccgcag cgtgctgcag    3720
atgcggaact ccaatgccgc cacaggcgag gactatatca cagcccgt gcgcgatctg    3780
aatgcgtgt gcttcgactc ccggtttcag aacccagagt ggcccatgga cgccgatgcc    3840
aatggcgcct accacatcgc cctgaagggc cagctgctgc tgaatcacct gaaggagagc    3900
aaggatctga agctgcagaa cggcatctcc aatcaggact ggctggccta catccaggag    3960
ctgcgcaaca agcgtcctgc tgctactaag aaagctggtc aagctaagaa aaagaaataa    4020
```

<210> SEQ ID NO 2
<211> LENGTH: 3783
<212> TYPE: DNA
<213> ORGANISM: Artificial Sequence
<220> FEATURE:

<223> OTHER INFORMATION: synthetic construct

<400> SEQUENCE: 2

```
atggcccaa agaagaagcg aaggtcggt atccacggag tcccagcagc cagcaagctg      60
gagaagttta caaactgcta ctccctgtct aagaccctga ggttcaaggc catccctgtg     120
ggcaagaccc aggagaacat cgacaataag cggctgctgg tggaggacga aagagagcc     180
gaggattata agggcgtgaa gaagctgctg atcgctact atctgtcttt tatcaacgac     240
gtgctgcaca gcatcaagct gaagaatctg aacaattaca tcagcctgtt ccggaagaaa    300
accagaaccg agaaggagaa taaggagctg gagaacctgg agaacctgg agatcaatct gcggaaggag     360
atcgccaagg ccttcaaggg caacgagggc tacaagtccc tgtttaagaa ggatatcatc     420
gagacaatcc tgccagagtt cctggacgat aaggacgaga tcgccctggt gaacagcttc     480
aatggcttta ccacagcctt caccggcttc tttgataaca gagagaatat gttttccgag    540
gaggccaaga gcacatccat cgccttcagg tgtatcaacg agaatctgac ccgctacatc     600
tctaatatgg acatcttcga aaggtgtgac gccatctttg ataagcacga ggtgcaggag     660
atcaaggaga agatcctgaa cagcgactat gatgtggagg attttcttga gggcgagttc     720
tttaacttg tgctgacaca gggagcatc gacgtgtata cgccatcat cggcggcttc     780
gtgaccgaga gcggcgagaa gatcaaggc ctgaacgagt acatcaacct gtataatcag     840
aaaccaagc agaagctgcc taagtttaag ccactgtata gcaggtgct gagcgatcgg     900
gagtctctga gcttctacgg cgagggctat acatccgatg aggaggtgct ggaggtgttt     960
agaaacaccc tgaacaagaa cagcgagatc ttcagctcca tcaagaagct ggagaagctg    1020
ttcaagaatt ttgacgagta ctctagcgcc ggcatctttg tgaagaacgg cccgccatc    1080
agcacaatct ccaaggatat cttcggcgag tggaacgtga tccgggacaa gtggaatgcc    1140
gagtatgacg atatccacct gaagaagaag gccgtggtga ccgagaagta cgaggacgat    1200
cggaaagt ccttcaagaa gatcggctcc tttctctgg agcagctgca ggagtacgcc    1260
gacgccgatc tgtctgtggt ggagaagctg aaggagatca tcatccagaa ggtggatgag    1320
atctacaagg tgtatggctc ctctgagaag ctgttcgacg ccgattttgt gctggagaag    1380
agcctgaaga gaacgacgc cgtggtggcc atcatgaagg acctgctgga ttctgtgaag    1440
agcttcgaga attacatcaa ggccttcttt ggcgagggca aggagacaaa cagggacgag    1500
tccttctatg cgattttgt gctggcctac gacatcctgc tgaaggtgga ccacatctac    1560
gatgccatcc gcaattatgt gacccagaag cctactcta aggataagtt caagctgtat    1620
tttcagaacc ctcagttcat gggcggctgg acaaggata aggagacaga ctatcgggcc    1680
accatcctga atacggctc caagtactat ctggccatca tggataagaa gtacgccaag    1740
tgcctgcaga agatcgacaa ggacgatgtg aacggcaatt acgagaagat caactataag    1800
ctgctgccg ccctaataa gatgctgcca aaggtgttct tttctaagaa gtggatggcc    1860
tactataacc cagcgagga catccagaag atctacaaga tggcacatt caagaagggc    1920
gatatgttta acctgaatga ctgtcacaag ctgatcgact tctttaagga tagcatctcc    1980
cggtatccaa agtggccaa tgcctacgat ttcaactttt ctgagacaga gaagtataag    2040
gacatcgccg gcttttacag agaggtggag gagcagggct ataaggtgag cttcgagtct    2100
gccagcaaga aggaggtgga taagctggtg gaggagggca gctgtatat gttccagatc    2160
tataacaagg acttttccga taagtctcac ggcacaccca atctgcacac catgtacttc    2220
aagctgctgt ttgacgagaa caatcacgga cagatcaggc tgagcggagg agcagagctg    2280
```

```
ttcatgaggc gcgcctccct gaagaaggag gagctggtgg tgcacccagc caactcccct    2340
atcgccaaca agaatccaga taatcccaag aaaaccacaa ccctgtccta cgacgtgtat    2400
aaggataaga ggttttctga ggaccagtac gagctgcaca tcccaatcgc catcaataag    2460
tgccccaaga acatcttcaa gatcaataca gaggtgcgcg tgctgctgaa gcacgacgat    2520 aaccccatg tgatcggcat cgataggggc gagcgcaatc tgctgtatat cgtggtggtg    2580
gacggcaagg gcaacatcgt ggagcagtat tccctgaacg agatcatcaa caacttcaac    2640
ggcatcagga tcaagacaga ttaccactct ctgctggaca agaaggagaa ggagaggttc    2700
gaggcccgcc agaactggac ctccatcgag aatatcaagg agctgaaggc cggctatatc    2760
tctcaggtgg tgcacaagat ctgcgagctg gtggagaagt acgatgccgt gatcgccctg    2820
gaggacctga actctggctt taagaatagc gcgtgaagg tggagaagca ggtgtatcag    2880
aagttcgaga gatgctgat cgataagctg aactacatgg tggacaagaa gtctaatcct    2940
tgtgcaacag gcggcgccct gaagggctat cagatcacca ataagttcga gagctttaag    3000
tccatgtcta cccagaacgg cttcatcttt tacatccctg cctggctgac atccaagatc    3060
gatccatcta ccggctttgt gaacctgctg aaaaccaagt ataccagcat cgccgattcc    3120
aagaagttca tcagctcctt tgacaggatc atgtacgtgc ccgaggagga tctgttcgag    3180
tttgccctgg actataagaa cttctctcgc acagacgccg attacatcaa gaagtggaag    3240
ctgtactcct acggcaaccg gatcagaatc ttccggaatc taagaagaa caacgtgttc    3300 gactgggagg aggtgtgcct gaccagcgcc tataaggagc tgttcaacaa gtacggcatc    3360
aattatcagc agggcgatat cagagccctg ctgtgcgagc agtccgacaa ggccttctac    3420
tctagcttta tggccctgat gagcctgatg ctgcagatgc ggaacagcat cacaggccgc    3480
accgacgtgg attttctgat cagccctgtg aagaactccg acggcatctt ctacgatagc    3540
cggaactatg aggcccagga gaatgccatc ctgccaaaga acgccgacgc caatggcgcc    3600
tataacatcg ccagaaaggt gctgtgggcc atcggccagt caagaaggc cgaggacgag    3660 aagctggata aggtgaagat cgccatctct aacaaggagt ggctggagta cgcccagacc    3720
agcgtgaagc acaagcgtcc tgctgctact aagaaagctg gtcaagctaa gaaaagaaa    3780 taa                                                                  3783
```

\<210\> SEQ ID NO 3
\<211\> LENGTH: 43
\<212\> TYPE: RNA
\<213\> ORGANISM: Artificial Sequence
\<220\> FEATURE:
\<223\> OTHER INFORMATION: synthetic construct

\<400\> SEQUENCE: 3

```
uaauuucuac ucuuguagau cugauggucc augucuguua cuc                       43
```

\<210\> SEQ ID NO 4
\<211\> LENGTH: 23
\<212\> TYPE: DNA
\<213\> ORGANISM: Artificial Sequence
\<220\> FEATURE:
\<223\> OTHER INFORMATION: synthetic construct

\<400\> SEQUENCE: 4

```
gctctagaat taccacagtt atc                                             23
```

\<210\> SEQ ID NO 5

```
<211> LENGTH: 23
<212> TYPE: DNA
<213> ORGANISM: Artificial Sequence
<220> FEATURE:
<223> OTHER INFORMATION: synthetic construct

<400> SEQUENCE: 5
aaatcagtta tggttccttt ggt                                              23

<210> SEQ ID NO 6
<211> LENGTH: 20
<212> TYPE: DNA
<213> ORGANISM: Artificial Sequence
<220> FEATURE:
<223> OTHER INFORMATION: synthetic construct

<400> SEQUENCE: 6
acgtaaacgg ccacaagttc                                                  20

<210> SEQ ID NO 7
<211> LENGTH: 20
<212> TYPE: DNA
<213> ORGANISM: Artificial Sequence
<220> FEATURE:
<223> OTHER INFORMATION: synthetic construct

<400> SEQUENCE: 7
aagtcgtgct gcttcatgtg                                                  20

<210> SEQ ID NO 8
<211> LENGTH: 43
<212> TYPE: RNA
<213> ORGANISM: Artificial Sequence
<220> FEATURE:
<223> OTHER INFORMATION: synthetic construct

<400> SEQUENCE: 8
aauuucuacu aaguguagau cugauggucc augucuguua cuc                        43

<210> SEQ ID NO 9
<211> LENGTH: 43
<212> TYPE: RNA
<213> ORGANISM: Artificial Sequence
<220> FEATURE:
<223> OTHER INFORMATION: synthetic construct

<400> SEQUENCE: 9
uaauuucuac ucuuguagau cuuacgaugg agccagagag gau                        43

<210> SEQ ID NO 10
<211> LENGTH: 43
<212> TYPE: RNA
<213> ORGANISM: Artificial Sequence
<220> FEATURE:
<223> OTHER INFORMATION: synthetic construct

<400> SEQUENCE: 10
uaauuucuac ucuuguagau gucggcaugg ccccauucgc acg                        43

<210> SEQ ID NO 11
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
```

<222> LOCATION: (1)..(43)
<223> OTHER INFORMATION: phosphodiester linkage is phosphorothioate

<400> SEQUENCE: 11
uaauuucuac ucuuguagau cugauggucc augucuguua cuc                    43

<210> SEQ ID NO 12
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(3)
<223> OTHER INFORMATION: 2'-fluoro ribose and phosphodiester linkage is
      phosphorothioate
<220> FEATURE:
<221> NAME/KEY: modified_base
<222> LOCATION: (41)..(43)
<223> OTHER INFORMATION: 2'-fluoro ribose and phosphodiester linkage is
      phosphorothioate

<400> SEQUENCE: 12
uaauuucuac ucuuguagau cugauggucc augucuguua cuc                    43

<210> SEQ ID NO 13
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(20)
<223> OTHER INFORMATION: 2'-O-methyl ribose

<400> SEQUENCE: 13
uaauuucuac ucuuguagau cugauggucc augucuguua cuc                    43

<210> SEQ ID NO 14
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(10)
<223> OTHER INFORMATION: 2'-O-methyl ribose

<400> SEQUENCE: 14
uaauuucuac ucuuguagau cugauggucc augucuguua cuc                    43

<210> SEQ ID NO 15
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(5)
<223> OTHER INFORMATION: 2'-O-methyl ribose

<400> SEQUENCE: 15
uaauuucuac ucuuguagau cugauggucc augucuguua cuc                    43

<210> SEQ ID NO 16

```
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(20)
<223> OTHER INFORMATION: 2'-fluoro ribose

<400> SEQUENCE: 16
uaauuucuac ucuuguagau cugauggucc augucuguua cuc                     43

<210> SEQ ID NO 17
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(10)
<223> OTHER INFORMATION: 2'-fluoro ribose

<400> SEQUENCE: 17
uaauuucuac ucuuguagau cugauggucc augucuguua cuc                     43

<210> SEQ ID NO 18
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(5)
<223> OTHER INFORMATION: 2'-fluoro ribose

<400> SEQUENCE: 18
uaauuucuac ucuuguagau cugauggucc augucuguua cuc                     43

<210> SEQ ID NO 19
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (21)..(23)
<223> OTHER INFORMATION: 2'-O-methyl ribose and phosphodiester linkage
      is phosphorothioate

<400> SEQUENCE: 19
uaauuucuac ucuuguagau cugauggucc augucuguua cuc                     43

<210> SEQ ID NO 20
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (21)..(23)
<223> OTHER INFORMATION: 2'-fluoro ribose

<400> SEQUENCE: 20
uaauuucuac ucuuguagau cugauggucc augucuguua cuc                     43
```

```
<210> SEQ ID NO 21
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (21)..(22)
<223> OTHER INFORMATION: 2'-fluoro ribose

<400> SEQUENCE: 21
uaauuucuac ucuuguagau cugauggucc augucuguua cuc                43

<210> SEQ ID NO 22
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (21)..(21)
<223> OTHER INFORMATION: 2'-fluoro ribose

<400> SEQUENCE: 22
uaauuucuac ucuuguagau cugauggucc augucuguua cuc                43

<210> SEQ ID NO 23
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (34)..(43)
<223> OTHER INFORMATION: 2'-O-methyl ribose

<400> SEQUENCE: 23
uaauuucuac ucuuguagau cugauggucc augucuguua cuc                43

<210> SEQ ID NO 24
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (39)..(43)
<223> OTHER INFORMATION: 2'-O-methyl ribose

<400> SEQUENCE: 24
uaauuucuac ucuuguagau cugauggucc augucuguua cuc                43

<210> SEQ ID NO 25
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (34)..(43)
<223> OTHER INFORMATION: 2'-fluoro ribose

<400> SEQUENCE: 25
uaauuucuac ucuuguagau cugauggucc augucuguua cuc                43
```

```
<210> SEQ ID NO 26
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (39)..(43)
<223> OTHER INFORMATION: 2'-fluoro ribose

<400> SEQUENCE: 26
uaauuucuac ucuuguagau cugauggucc augucuguua cuc                43

<210> SEQ ID NO 27
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (39)..(43)
<223> OTHER INFORMATION: 2'-fluoro ribose and phosphodiester linkage is
      phosphorothioate

<400> SEQUENCE: 27
uaauuucuac ucuuguagau cugauggucc augucuguua cuc                43

<210> SEQ ID NO 28
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (39)..(43)
<223> OTHER INFORMATION: unlocked nucleotide

<400> SEQUENCE: 28
uaauuucuac ucuuguagau cugauggucc augucuguua cuc                43

<210> SEQ ID NO 29
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (39)..(43)
<223> OTHER INFORMATION: locked nucleotide

<400> SEQUENCE: 29
uaauuucuac ucuuguagau cugauggucc augucuguua cuc                43

<210> SEQ ID NO 30
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (5)..(6)
<223> OTHER INFORMATION: 2'-fluoro ribose
<220> FEATURE:
<221> NAME/KEY: modified_base
```

<222> LOCATION: (9)..(10)
<223> OTHER INFORMATION: 2'-fluoro ribose
<220> FEATURE:
<221> NAME/KEY: modified_base
<222> LOCATION: (12)..(14)
<223> OTHER INFORMATION: 2'-fluoro ribose
<220> FEATURE:
<221> NAME/KEY: modified_base
<222> LOCATION: (16)..(19)
<223> OTHER INFORMATION: 2'-fluoro ribose
<220> FEATURE:
<221> NAME/KEY: modified_base
<222> LOCATION: (29)..(33)
<223> OTHER INFORMATION: 2'-fluoro ribose
<220> FEATURE:
<221> NAME/KEY: modified_base
<222> LOCATION: (37)..(37)
<223> OTHER INFORMATION: 2'-fluoro ribose
<220> FEATURE:
<221> NAME/KEY: modified_base
<222> LOCATION: (39)..(43)
<223> OTHER INFORMATION: 2'-fluoro ribose

<400> SEQUENCE: 30
uaauuucuac ucuuguagau cugauggucc augucuguua cuc                43

<210> SEQ ID NO 31
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (5)..(6)
<223> OTHER INFORMATION: 2'-O-methyl ribose
<220> FEATURE:
<221> NAME/KEY: modified_base
<222> LOCATION: (9)..(10)
<223> OTHER INFORMATION: 2'-O-methyl ribose
<220> FEATURE:
<221> NAME/KEY: modified_base
<222> LOCATION: (12)..(14)
<223> OTHER INFORMATION: 2'-O-methyl ribose
<220> FEATURE:
<221> NAME/KEY: modified_base
<222> LOCATION: (16)..(19)
<223> OTHER INFORMATION: 2'-O-methyl ribose
<220> FEATURE:
<221> NAME/KEY: modified_base
<222> LOCATION: (29)..(32)
<223> OTHER INFORMATION: 2'-O-methyl ribose
<220> FEATURE:
<221> NAME/KEY: modified_base
<222> LOCATION: (37)..(37)
<223> OTHER INFORMATION: 2'-O-methyl ribose
<220> FEATURE:
<221> NAME/KEY: modified_base
<222> LOCATION: (39)..(43)
<223> OTHER INFORMATION: 2'-fluoro ribose

<400> SEQUENCE: 31
uaauuucuac ucuuguagau cugauggucc augucuguua cuc                43

<210> SEQ ID NO 32
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (5)..(6)
<223> OTHER INFORMATION: 2'-O-methyl ribose and phosphodiester linkage
    is phosphorothioate <220> FEATURE:
<221> NAME/KEY: modified_base
<222> LOCATION: (9)..(10)
<223> OTHER INFORMATION: 2'-O-methyl ribose and phosphodiester linkage is phosphorothioate
<220> FEATURE:
<221> NAME/KEY: modified_base
<222> LOCATION: (12)..(14)
<223> OTHER INFORMATION: 2'-O-methyl ribose and phosphodiester linkage is phosphorothioate
<220> FEATURE:
<221> NAME/KEY: modified_base
<222> LOCATION: (16)..(19)
<223> OTHER INFORMATION: 2'-O-methyl ribose and phosphodiester linkage is phosphorothioate
<220> FEATURE:
<221> NAME/KEY: modified_base
<222> LOCATION: (29)..(32)
<223> OTHER INFORMATION: 2'-O-methyl ribose and phosphodiester linkage is phosphorothioate
<220> FEATURE:
<221> NAME/KEY: modified_base
<222> LOCATION: (37)..(37)
<223> OTHER INFORMATION: 2'-O-methyl ribose and phosphodiester linkage is phosphorothioate
<220> FEATURE:
<221> NAME/KEY: modified_base
<222> LOCATION: (39)..(43)
<223> OTHER INFORMATION: 2'-fluoro ribose

<400> SEQUENCE: 32
uaauuucuac ucuuguagau cugauggucc augucuguua cuc                43

<210> SEQ ID NO 33
<211> LENGTH: 12
<212> TYPE: RNA
<213> ORGANISM: Artificial Sequence
<220> FEATURE:
<223> OTHER INFORMATION: synthetic construct

<400> SEQUENCE: 33
uaauuucuac uc                                                  12

<210> SEQ ID NO 34
<211> LENGTH: 31
<212> TYPE: RNA
<213> ORGANISM: Artificial Sequence
<220> FEATURE:
<223> OTHER INFORMATION: synthetic construct

<400> SEQUENCE: 34
uuguagaucu gaugguccau gucuguuacu c                             31

<210> SEQ ID NO 35
<211> LENGTH: 41
<212> TYPE: RNA
<213> ORGANISM: Artificial Sequence
<220> FEATURE:
<223> OTHER INFORMATION: synthetic construct

<400> SEQUENCE: 35
uaauucuacu cuuguagucu gaugguccau gucuguuacu c                  41

<210> SEQ ID NO 36
<211> LENGTH: 39
<212> TYPE: RNA
<213> ORGANISM: Artificial Sequence
<220> FEATURE:
<223> OTHER INFORMATION: synthetic construct

<400> SEQUENCE: 36
uaauuucuuc uuagaucuga ugguccaugu cuguuacuc                    39

<210> SEQ ID NO 37
<211> LENGTH: 35
<212> TYPE: RNA
<213> ORGANISM: Artificial Sequence
<220> FEATURE:
<223> OTHER INFORMATION: synthetic construct

<400> SEQUENCE: 37
uaauuuucuu aucugauggu ccaugucugu uacuc                        35

<210> SEQ ID NO 38
<211> LENGTH: 47
<212> TYPE: RNA
<213> ORGANISM: Artificial Sequence
<220> FEATURE:
<223> OTHER INFORMATION: synthetic construct

<400> SEQUENCE: 38
uaauuucuac acucuugugu agaucugaug guccaugucu guuacuc            47

<210> SEQ ID NO 39
<211> LENGTH: 47
<212> TYPE: RNA
<213> ORGANISM: Artificial Sequence
<220> FEATURE:
<223> OTHER INFORMATION: synthetic construct

<400> SEQUENCE: 39
uaauuucuac ucucuugugu agaucugaug guccaugucu guuacuc            47

<210> SEQ ID NO 40
<211> LENGTH: 49
<212> TYPE: RNA
<213> ORGANISM: Artificial Sequence
<220> FEATURE:
<223> OTHER INFORMATION: synthetic construct

<400> SEQUENCE: 40
uaauuucuac ugcucuugcu guagaucuga ugguccaugu cuguuacuc          49

<210> SEQ ID NO 41
<211> LENGTH: 51
<212> TYPE: RNA
<213> ORGANISM: Artificial Sequence
<220> FEATURE:
<223> OTHER INFORMATION: synthetic construct

<400> SEQUENCE: 41
uaauuucuac acacucuugu guguagaucu gauggccau gucuguuacu c        51

<210> SEQ ID NO 42
<211> LENGTH: 55
<212> TYPE: RNA
<213> ORGANISM: Artificial Sequence
<220> FEATURE:
<223> OTHER INFORMATION: synthetic construct

<400> SEQUENCE: 42
uaauuucuac acacacucuu gugugugag aucgauggu ccaugucugu uacuc    55

<210> SEQ ID NO 43
<211> LENGTH: 43
<212> TYPE: RNA

<213> ORGANISM: Artificial Sequence
<220> FEATURE:
<223> OTHER INFORMATION: synthetic construct

<400> SEQUENCE: 43
uaauuucuac uguuguagau cugauggucc augucuguua cuc    43

<210> SEQ ID NO 44
<211> LENGTH: 44
<212> TYPE: RNA
<213> ORGANISM: Artificial Sequence
<220> FEATURE:
<223> OTHER INFORMATION: synthetic construct

<400> SEQUENCE: 44
uaauuucuac guucuguaga ucgauggguc caugucuguu acuc    44

<210> SEQ ID NO 45
<211> LENGTH: 44
<212> TYPE: RNA
<213> ORGANISM: Artificial Sequence
<220> FEATURE:
<223> OTHER INFORMATION: synthetic construct

<400> SEQUENCE: 45
uaauuucuac guaauguaga ucgauggguc caugucuguu acuc    44

<210> SEQ ID NO 46
<211> LENGTH: 43
<212> TYPE: RNA
<213> ORGANISM: Artificial Sequence
<220> FEATURE:
<223> OTHER INFORMATION: synthetic construct

<400> SEQUENCE: 46
uaauuucuac uuuuguagau cgauggguccc augucuguua cuc    43

<210> SEQ ID NO 47
<211> LENGTH: 44
<212> TYPE: RNA
<213> ORGANISM: Artificial Sequence
<220> FEATURE:
<223> OTHER INFORMATION: synthetic construct

<400> SEQUENCE: 47
uaauuucuac acgcgguaga ucgauggguc caugucuguu acuc    44

<210> SEQ ID NO 48
<211> LENGTH: 43
<212> TYPE: RNA
<213> ORGANISM: Artificial Sequence
<220> FEATURE:
<223> OTHER INFORMATION: synthetic construct

<400> SEQUENCE: 48
uaauuucuac uauuguagau cgauggguccc augucuguua cuc    43

<210> SEQ ID NO 49
<211> LENGTH: 44
<212> TYPE: RNA
<213> ORGANISM: Artificial Sequence
<220> FEATURE:
<223> OTHER INFORMATION: synthetic construct

<400> SEQUENCE: 49
uaauuucuac ucuuuguaga ucgauggguc caugucuguu acuc    44

<210> SEQ ID NO 50
<211> LENGTH: 42
<212> TYPE: RNA
<213> ORGANISM: Artificial Sequence
<220> FEATURE:
<223> OTHER INFORMATION: synthetic construct

<400> SEQUENCE: 50
uaauuucuac uuuguagauc ugauggucca ugucuguuac uc                          42

<210> SEQ ID NO 51
<211> LENGTH: 44
<212> TYPE: RNA
<213> ORGANISM: Artificial Sequence
<220> FEATURE:
<223> OTHER INFORMATION: synthetic construct

<400> SEQUENCE: 51
uaauuucuac uguuuguaga ucgauggguc caugucuguu acuc                        44

<210> SEQ ID NO 52
<211> LENGTH: 43
<212> TYPE: RNA
<213> ORGANISM: Artificial Sequence
<220> FEATURE:
<223> OTHER INFORMATION: synthetic construct

<400> SEQUENCE: 52
uaauuucuac uucgguagau cugauggucc augucuguua cuc                         43

<210> SEQ ID NO 53
<211> LENGTH: 43
<212> TYPE: RNA
<213> ORGANISM: Artificial Sequence
<220> FEATURE:
<223> OTHER INFORMATION: synthetic construct

<400> SEQUENCE: 53
aauuucuacu aaguguagau cugauggucc augucuguua cuc                         43

<210> SEQ ID NO 54
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (39)..(43)
<223> OTHER INFORMATION: 2'-fluoro ribose

<400> SEQUENCE: 54
uaauuucuac ucuuguagau cuuacgaugg agccagagag gau                         43

<210> SEQ ID NO 55
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (39)..(43)
<223> OTHER INFORMATION: 2'-fluoro ribose

<400> SEQUENCE: 55
uaauuucuac ucuuguagau gucggcaugg ccccauucgc acg    43

<210> SEQ ID NO 56
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (39)..(43)
<223> OTHER INFORMATION: 2'-fluoro ribose

<400> SEQUENCE: 56
aauuucuacu aaguguagau cugauggucc augucuguua cuc    43

<210> SEQ ID NO 57
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (5)..(6)
<223> OTHER INFORMATION: 2'-O-methyl ribose
<220> FEATURE:
<221> NAME/KEY: modified_base
<222> LOCATION: (9)..(10)
<223> OTHER INFORMATION: 2'-O-methyl ribose
<220> FEATURE:
<221> NAME/KEY: modified_base
<222> LOCATION: (12)..(14)
<223> OTHER INFORMATION: 2'-O-methyl ribose
<220> FEATURE:
<221> NAME/KEY: modified_base
<222> LOCATION: (16)..(19)
<223> OTHER INFORMATION: 2'-O-methyl ribose
<220> FEATURE:
<221> NAME/KEY: modified_base
<222> LOCATION: (29)..(32)
<223> OTHER INFORMATION: 2'-O-methyl ribose
<220> FEATURE:
<221> NAME/KEY: modified_base
<222> LOCATION: (37)..(37)
<223> OTHER INFORMATION: 2'-O-methyl ribose
<220> FEATURE:
<221> NAME/KEY: modified_base
<222> LOCATION: (39)..(43)
<223> OTHER INFORMATION: 2'-fluoro ribose

<400> SEQUENCE: 57
uaauuucuac ucuuguagau cugauggucc augucuguua cuc    43

<210> SEQ ID NO 58
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (5)..(6)
<223> OTHER INFORMATION: 2'-O-methyl ribose and phosphodiester linkage
      is phosphorothioate
<220> FEATURE:
<221> NAME/KEY: modified_base
<222> LOCATION: (9)..(10)
<223> OTHER INFORMATION: 2'-O-methyl ribose and phosphodiester linkage
      is phosphorothioate
<220> FEATURE:
<221> NAME/KEY: modified_base
<222> LOCATION: (12)..(14)
<223> OTHER INFORMATION: 2'-O-methyl ribose and phosphodiester linkage

```
      is phosphorothioate
<220> FEATURE:
<221> NAME/KEY: modified_base
<222> LOCATION: (16)..(19)
<223> OTHER INFORMATION: 2'-O-methyl ribose and phosphodiester linkage
      is phosphorothioate
<220> FEATURE:
<221> NAME/KEY: modified_base
<222> LOCATION: (29)..(32)
<223> OTHER INFORMATION: 2'-O-methyl ribose and phosphodiester linkage
      is phosphorothioate
<220> FEATURE:
<221> NAME/KEY: modified_base
<222> LOCATION: (37)..(37)
<223> OTHER INFORMATION: 2'-O-methyl ribose
<220> FEATURE:
<221> NAME/KEY: modified_base
<222> LOCATION: (39)..(43)
<223> OTHER INFORMATION: 2'-fluoro ribose

<400> SEQUENCE: 58
uaauuucuac ucuuguagau cugauggucc augucuguua cuc                          43

<210> SEQ ID NO 59
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (5)..(6)
<223> OTHER INFORMATION: phosphodiester linkage is phosphorothioate
<220> FEATURE:
<221> NAME/KEY: modified_base
<222> LOCATION: (9)..(10)
<223> OTHER INFORMATION: phosphodiester linkage is phosphorothioate
<220> FEATURE:
<221> NAME/KEY: modified_base
<222> LOCATION: (12)..(14)
<223> OTHER INFORMATION: phosphodiester linkage is phosphorothioate
<220> FEATURE:
<221> NAME/KEY: modified_base
<222> LOCATION: (16)..(19)
<223> OTHER INFORMATION: phosphodiester linkage is phosphorothioate
<220> FEATURE:
<221> NAME/KEY: modified_base
<222> LOCATION: (29)..(32)
<223> OTHER INFORMATION: phosphodiester linkage is phosphorothioate
<220> FEATURE:
<221> NAME/KEY: modified_base
<222> LOCATION: (39)..(43)
<223> OTHER INFORMATION: 2'-fluoro ribose

<400> SEQUENCE: 59
uaauuucuac ucuuguagau cugauggucc augucuguua cuc                          43

<210> SEQ ID NO 60
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (5)..(6)
<223> OTHER INFORMATION: 2'-fluoro ribose
<220> FEATURE:
<221> NAME/KEY: modified_base
<222> LOCATION: (9)..(10)
<223> OTHER INFORMATION: 2'-fluoro ribose
<220> FEATURE:
<221> NAME/KEY: modified_base
<222> LOCATION: (12)..(14)
<223> OTHER INFORMATION: 2'-fluoro ribose
```

```
<220> FEATURE:
<221> NAME/KEY: modified_base
<222> LOCATION: (16)..(19)
<223> OTHER INFORMATION: 2'-fluoro ribose
<220> FEATURE:
<221> NAME/KEY: modified_base
<222> LOCATION: (29)..(32)
<223> OTHER INFORMATION: 2'-fluoro ribose
<220> FEATURE:
<221> NAME/KEY: modified_base
<222> LOCATION: (37)..(37)
<223> OTHER INFORMATION: 2'-fluoro ribose
<220> FEATURE:
<221> NAME/KEY: modified_base
<222> LOCATION: (39)..(43)
<223> OTHER INFORMATION: 2'-fluoro ribose

<400> SEQUENCE: 60
uaauuucuac ucuuguagau cugauggucc augucuguua cuc                43

<210> SEQ ID NO 61
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (29)..(32)
<223> OTHER INFORMATION: 2'-fluoro ribose
<220> FEATURE:
<221> NAME/KEY: modified_base
<222> LOCATION: (37)..(37)
<223> OTHER INFORMATION: 2'-fluoro ribose
<220> FEATURE:
<221> NAME/KEY: modified_base
<222> LOCATION: (39)..(43)
<223> OTHER INFORMATION: 2'-fluoro ribose

<400> SEQUENCE: 61
uaauuucuac ucuuguagau cugauggucc augucuguua cuc                43

<210> SEQ ID NO 62
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (41)..(43)
<223> OTHER INFORMATION: 2'-fluoro ribose

<400> SEQUENCE: 62
uaauuucuac ucuuguagau cugauggucc augucuguua cuc                43

<210> SEQ ID NO 63
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (43)..(43)
<223> OTHER INFORMATION: 2'-fluoro ribose

<400> SEQUENCE: 63
uaauuucuac ucuuguagau cugauggucc augucuguua cuc                43

<210> SEQ ID NO 64
```

```
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (5)..(6)
<223> OTHER INFORMATION: Deoxyribose
<220> FEATURE:
<221> NAME/KEY: modified_base
<222> LOCATION: (9)..(10)
<223> OTHER INFORMATION: Deoxyribose
<220> FEATURE:
<221> NAME/KEY: modified_base
<222> LOCATION: (12)..(14)
<223> OTHER INFORMATION: Deoxyribose
<220> FEATURE:
<221> NAME/KEY: modified_base
<222> LOCATION: (16)..(19)
<223> OTHER INFORMATION: Deoxyribose
<220> FEATURE:
<221> NAME/KEY: modified_base
<222> LOCATION: (29)..(32)
<223> OTHER INFORMATION: Deoxyribose
<220> FEATURE:
<221> NAME/KEY: modified_base
<222> LOCATION: (37)..(37)
<223> OTHER INFORMATION: Deoxyribose
<220> FEATURE:
<221> NAME/KEY: modified_base
<222> LOCATION: (39)..(43)
<223> OTHER INFORMATION: Deoxyribose

<400> SEQUENCE: 64
uaauuucuac ucuuguagau cugauggucc augucuguua cuc                43

<210> SEQ ID NO 65
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (29)..(32)
<223> OTHER INFORMATION: Deoxyribose
<220> FEATURE:
<221> NAME/KEY: modified_base
<222> LOCATION: (37)..(37)
<223> OTHER INFORMATION: Deoxyribose
<220> FEATURE:
<221> NAME/KEY: modified_base
<222> LOCATION: (39)..(43)
<223> OTHER INFORMATION: Deoxyribose

<400> SEQUENCE: 65
uaauuucuac ucuuguagau cugauggucc augucuguua cuc                43

<210> SEQ ID NO 66
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (39)..(43)
<223> OTHER INFORMATION: Deoxyribose

<400> SEQUENCE: 66
uaauuucuac ucuuguagau cugauggucc augucuguua cuc                43
```

```
<210> SEQ ID NO 67
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: pseudouridine
<220> FEATURE:
<221> NAME/KEY: modified_base
<222> LOCATION: (4)..(6)
<223> OTHER INFORMATION: pseudouridine
<220> FEATURE:
<221> NAME/KEY: modified_base
<222> LOCATION: (8)..(8)
<223> OTHER INFORMATION: pseudouridine
<220> FEATURE:
<221> NAME/KEY: modified_base
<222> LOCATION: (11)..(11)
<223> OTHER INFORMATION: pseudouridine
<220> FEATURE:
<221> NAME/KEY: modified_base
<222> LOCATION: (13)..(14)
<223> OTHER INFORMATION: pseudouridine
<220> FEATURE:
<221> NAME/KEY: modified_base
<222> LOCATION: (16)..(16)
<223> OTHER INFORMATION: pseudouridine
<220> FEATURE:
<221> NAME/KEY: modified_base
<222> LOCATION: (20)..(20)
<223> OTHER INFORMATION: pseudouridine
<220> FEATURE:
<221> NAME/KEY: modified_base
<222> LOCATION: (22)..(22)
<223> OTHER INFORMATION: pseudouridine
<220> FEATURE:
<221> NAME/KEY: modified_base
<222> LOCATION: (25)..(25)
<223> OTHER INFORMATION: pseudouridine
<220> FEATURE:
<221> NAME/KEY: modified_base
<222> LOCATION: (28)..(28)
<223> OTHER INFORMATION: pseudouridine
<220> FEATURE:
<221> NAME/KEY: modified_base
<222> LOCATION: (33)..(33)
<223> OTHER INFORMATION: pseudouridine
<220> FEATURE:
<221> NAME/KEY: modified_base
<222> LOCATION: (34)..(34)
<223> OTHER INFORMATION: pseudouridine
<220> FEATURE:
<221> NAME/KEY: modified_base
<222> LOCATION: (36)..(36)
<223> OTHER INFORMATION: pseudouridine
<220> FEATURE:
<221> NAME/KEY: modified_base
<222> LOCATION: (38)..(39)
<223> OTHER INFORMATION: pseudouridine
<220> FEATURE:
<221> NAME/KEY: modified_base
<222> LOCATION: (42)..(42)
<223> OTHER INFORMATION: pseudouridine

<400> SEQUENCE: 67
uaauuucuac ucuuguagau cugauggucc augucuguua cuc                 43

<210> SEQ ID NO 68
<211> LENGTH: 43
<212> TYPE: RNA
<213> ORGANISM: Artificial Sequence
<220> FEATURE:
<223> OTHER INFORMATION: synthetic construct
<220> FEATURE:
```

```
<221> NAME/KEY: modified_base
<222> LOCATION: (7)..(7)
<223> OTHER INFORMATION: 5-methylcytidine
<220> FEATURE:
<221> NAME/KEY: modified_base
<222> LOCATION: (10)..(10)
<223> OTHER INFORMATION: 5-methylcytidine
<220> FEATURE:
<221> NAME/KEY: modified_base
<222> LOCATION: (12)..(12)
<223> OTHER INFORMATION: 5-methylcytidine
<220> FEATURE:
<221> NAME/KEY: modified_base
<222> LOCATION: (12)..(12)
<223> OTHER INFORMATION: 5-methylcytidine
<220> FEATURE:
<221> NAME/KEY: modified_base
<222> LOCATION: (21)..(21)
<223> OTHER INFORMATION: 5-methylcytidine
<220> FEATURE:
<221> NAME/KEY: modified_base
<222> LOCATION: (29)..(30)
<223> OTHER INFORMATION: 5-methylcytidine
<220> FEATURE:
<221> NAME/KEY: modified_base
<222> LOCATION: (35)..(35)
<223> OTHER INFORMATION: 5-methylcytidine
<220> FEATURE:
<221> NAME/KEY: modified_base
<222> LOCATION: (41)..(41)
<223> OTHER INFORMATION: 5-methylcytidine
<220> FEATURE:
<221> NAME/KEY: modified_base
<222> LOCATION: (43)..(43)
<223> OTHER INFORMATION: 5-methylcytidine

<400> SEQUENCE: 68
uaauuucuac ucuuguagau cugauggucc augucuguua cuc                    43

<210> SEQ ID NO 69
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: 5-methoxycytidine
<220> FEATURE:
<221> NAME/KEY: modified_base
<222> LOCATION: (4)..(6)
<223> OTHER INFORMATION: 5-methoxycytidine
<220> FEATURE:
<221> NAME/KEY: modified_base
<222> LOCATION: (8)..(8)
<223> OTHER INFORMATION: 5-methoxycytidine
<220> FEATURE:
<221> NAME/KEY: modified_base
<222> LOCATION: (11)..(11)
<223> OTHER INFORMATION: 5-methoxycytidine
<220> FEATURE:
<221> NAME/KEY: modified_base
<222> LOCATION: (13)..(14)
<223> OTHER INFORMATION: 5-methoxycytidine
<220> FEATURE:
<221> NAME/KEY: modified_base
<222> LOCATION: (16)..(16)
<223> OTHER INFORMATION: 5-methoxycytidine
<220> FEATURE:
<221> NAME/KEY: modified_base
<222> LOCATION: (20)..(20)
<223> OTHER INFORMATION: 5-methoxycytidine
<220> FEATURE:
<221> NAME/KEY: modified_base
<222> LOCATION: (22)..(22)
<223> OTHER INFORMATION: 5-methoxycytidine
```

```
<220> FEATURE:
<221> NAME/KEY: modified_base
<222> LOCATION: (25)..(25)
<223> OTHER INFORMATION: 5-methoxycytidine
<220> FEATURE:
<221> NAME/KEY: modified_base
<222> LOCATION: (28)..(28)
<223> OTHER INFORMATION: 5-methoxycytidine
<220> FEATURE:
<221> NAME/KEY: modified_base
<222> LOCATION: (32)..(32)
<223> OTHER INFORMATION: 5-methoxycytidine
<220> FEATURE:
<221> NAME/KEY: modified_base
<222> LOCATION: (34)..(34)
<223> OTHER INFORMATION: 5-methoxycytidine
<220> FEATURE:
<221> NAME/KEY: modified_base
<222> LOCATION: (36)..(36)
<223> OTHER INFORMATION: 5-methoxycytidine
<220> FEATURE:
<221> NAME/KEY: modified_base
<222> LOCATION: (38)..(39)
<223> OTHER INFORMATION: 5-methoxycytidine
<220> FEATURE:
<221> NAME/KEY: modified_base
<222> LOCATION: (42)..(42)
<223> OTHER INFORMATION: 5-methoxycytidine

<400> SEQUENCE: 69
uaauuucuac ucuuguagau cugauggucc augucuguua cuc               43

<210> SEQ ID NO 70
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (2)..(3)
<223> OTHER INFORMATION: N6-methyladenosine
<220> FEATURE:
<221> NAME/KEY: modified_base
<222> LOCATION: (9)..(9)
<223> OTHER INFORMATION: N6-methyladenosine
<220> FEATURE:
<221> NAME/KEY: modified_base
<222> LOCATION: (17)..(17)
<223> OTHER INFORMATION: N6-methyladenosine
<220> FEATURE:
<221> NAME/KEY: modified_base
<222> LOCATION: (19)..(19)
<223> OTHER INFORMATION: N6-methyladenosine
<220> FEATURE:
<221> NAME/KEY: modified_base
<222> LOCATION: (24)..(24)
<223> OTHER INFORMATION: N6-methyladenosine
<220> FEATURE:
<221> NAME/KEY: modified_base
<222> LOCATION: (31)..(31)
<223> OTHER INFORMATION: N6-methyladenosine
<220> FEATURE:
<221> NAME/KEY: modified_base
<222> LOCATION: (40)..(40)
<223> OTHER INFORMATION: N6-methyladenosine

<400> SEQUENCE: 70
uaauuucuac ucuuguagau cugauggucc augucuguua cuc               43

<210> SEQ ID NO 71
<211> LENGTH: 43
<212> TYPE: RNA
<213> ORGANISM: Artificial Sequence
<220> FEATURE:
```

```
<223> OTHER INFORMATION: synthetic construct
<220> FEATURE:
<221> NAME/KEY: modified_base
<222> LOCATION: (5)..(6)
<223> OTHER INFORMATION: 2'-fluoro ribose and phosphodiester linkage is
      phosphorothioate
<220> FEATURE:
<221> NAME/KEY: modified_base
<222> LOCATION: (9)..(10)
<223> OTHER INFORMATION: 2'-fluoro ribose and phosphodiester linkage is
      phosphorothioate
<220> FEATURE:
<221> NAME/KEY: modified_base
<222> LOCATION: (12)..(14)
<223> OTHER INFORMATION: 2'-fluoro ribose and phosphodiester linkage is
      phosphorothioate
<220> FEATURE:
<221> NAME/KEY: modified_base
<222> LOCATION: (16)..(19)
<223> OTHER INFORMATION: 2'-fluoro ribose and phosphodiester linkage is
      phosphorothioate
<220> FEATURE:
<221> NAME/KEY: modified_base
<222> LOCATION: (29)..(32)
<223> OTHER INFORMATION: 2'-fluoro ribose
<220> FEATURE:
<221> NAME/KEY: modified_base
<222> LOCATION: (37)..(37)
<223> OTHER INFORMATION: 2'-fluoro ribose
<220> FEATURE:
<221> NAME/KEY: modified_base
<222> LOCATION: (39)..(43)
<223> OTHER INFORMATION: 2'-fluoro ribose

<400> SEQUENCE: 71
uaauuucuac ucuuguagau cugauggucc augucuguua cuc                        43

<210> SEQ ID NO 72
<211> LENGTH: 43
<212> TYPE: RNA
<213> ORGANISM: Artificial Sequence
<220> FEATURE:
<223> OTHER INFORMATION: synthetic construct
<220> FEATURE:
<221> NAME/KEY: modified_base
<222> LOCATION: (5)..(6)
<223> OTHER INFORMATION: 2'-fluoro ribose
<220> FEATURE:
<221> NAME/KEY: modified_base
<222> LOCATION: (9)..(10)
<223> OTHER INFORMATION: 2'-fluoro ribose
<220> FEATURE:
<221> NAME/KEY: modified_base
<222> LOCATION: (12)..(14)
<223> OTHER INFORMATION: 2'-fluoro ribose
<220> FEATURE:
<221> NAME/KEY: modified_base
<222> LOCATION: (16)..(19)
<223> OTHER INFORMATION: 2'-fluoro ribose
<220> FEATURE:
<221> NAME/KEY: modified_base
<222> LOCATION: (29)..(32)
<223> OTHER INFORMATION: 2'-fluoro ribose and phosphodiester linkage is
      phosphorothioate
<220> FEATURE:
<221> NAME/KEY: modified_base
<222> LOCATION: (37)..(37)
<223> OTHER INFORMATION: 2'-fluoro ribose
<220> FEATURE:
<221> NAME/KEY: modified_base
<222> LOCATION: (39)..(43)
<223> OTHER INFORMATION: 2'-fluoro ribose

<400> SEQUENCE: 72
uaauuucuac ucuuguagau cugauggucc augucuguua cuc                        43
```

-continued

<210> SEQ ID NO 73
<211> LENGTH: 48
<212> TYPE: RNA
<213> ORGANISM: Artificial Sequence
<220> FEATURE:
<223> OTHER INFORMATION: synthetic construct

<400> SEQUENCE: 73
uaauuucuac ucuuguagau cugauggucc augucuguua cucgccug        48

<210> SEQ ID NO 74
<211> LENGTH: 27
<212> TYPE: DNA
<213> ORGANISM: Artificial Sequence
<220> FEATURE:
<223> OTHER INFORMATION: synthetic construct

<400> SEQUENCE: 74
tttcctgatg gtccatgtct gttactc        27

<210> SEQ ID NO 75
<211> LENGTH: 27
<212> TYPE: DNA
<213> ORGANISM: Homo sapiens

<400> SEQUENCE: 75
tttcctgctg gtccatgtct aatactc        27

<210> SEQ ID NO 76
<211> LENGTH: 27
<212> TYPE: DNA
<213> ORGANISM: Homo sapiens

<400> SEQUENCE: 76
ttttctgatg gtccatacct gttacac        27

<210> SEQ ID NO 77
<211> LENGTH: 27
<212> TYPE: DNA
<213> ORGANISM: Homo sapiens

<400> SEQUENCE: 77
ttttcttatt gtacatgtct gtaactc        27

<210> SEQ ID NO 78
<211> LENGTH: 27
<212> TYPE: DNA
<213> ORGANISM: Homo sapiens

<400> SEQUENCE: 78
tttcctgatg gtccacacct gttacac        27

<210> SEQ ID NO 79
<211> LENGTH: 27
<212> TYPE: DNA
<213> ORGANISM: Homo sapiens

<400> SEQUENCE: 79
tttgcttacg atggagccag agaggat        27

<210> SEQ ID NO 80
<211> LENGTH: 27
<212> TYPE: DNA
<213> ORGANISM: Homo sapiens

```
<400> SEQUENCE: 80
tttggtcggc atggccccat tcgcacg                                          27

<210> SEQ ID NO 81
<211> LENGTH: 20
<212> TYPE: DNA
<213> ORGANISM: Homo sapiens

<400> SEQUENCE: 81
ctgggactca ggcgggtcac                                                  20

<210> SEQ ID NO 82
<211> LENGTH: 21
<212> TYPE: DNA
<213> ORGANISM: Artificial Sequence
<220> FEATURE:
<223> OTHER INFORMATION: synthetic construct

<400> SEQUENCE: 82
cctcagccag aagtcccgtg c                                                21

<210> SEQ ID NO 83
<211> LENGTH: 23
<212> TYPE: DNA
<213> ORGANISM: Artificial Sequence
<220> FEATURE:
<223> OTHER INFORMATION: synthetic construct

<400> SEQUENCE: 83
aggaaagcca tgccagagac tca                                              23

<210> SEQ ID NO 84
<211> LENGTH: 21
<212> TYPE: DNA
<213> ORGANISM: Artificial Sequence
<220> FEATURE:
<223> OTHER INFORMATION: synthetic construct

<400> SEQUENCE: 84
caccgccact ctgtttccaa g                                                21

<210> SEQ ID NO 85
<211> LENGTH: 24
<212> TYPE: DNA
<213> ORGANISM: Artificial Sequence
<220> FEATURE:
<223> OTHER INFORMATION: synthetic construct

<400> SEQUENCE: 85
gttgggacat gaaggtcaag tgtg                                             24

<210> SEQ ID NO 86
<211> LENGTH: 24
<212> TYPE: DNA
<213> ORGANISM: Artificial Sequence
<220> FEATURE:
<223> OTHER INFORMATION: synthetic construct

<400> SEQUENCE: 86
tttgtctcct gttgccttca ggcc                                             24

<210> SEQ ID NO 87
<211> LENGTH: 24
<212> TYPE: DNA
```

```
<213> ORGANISM: Artificial Sequence
<220> FEATURE:
<223> OTHER INFORMATION: synthetic construct

<400> SEQUENCE: 87
gaggcatagc aaggtcatgc cttt                                              24

<210> SEQ ID NO 88
<211> LENGTH: 20
<212> TYPE: DNA
<213> ORGANISM: Artificial Sequence
<220> FEATURE:
<223> OTHER INFORMATION: synthetic construct

<400> SEQUENCE: 88
tgcttccctt ggtggagctg                                                   20

<210> SEQ ID NO 89
<211> LENGTH: 21
<212> TYPE: DNA
<213> ORGANISM: Artificial Sequence
<220> FEATURE:
<223> OTHER INFORMATION: synthetic construct

<400> SEQUENCE: 89
tttccatgta ggcccatgcc c                                                 21

<210> SEQ ID NO 90
<211> LENGTH: 23
<212> TYPE: DNA
<213> ORGANISM: Artificial Sequence
<220> FEATURE:
<223> OTHER INFORMATION: synthetic construct

<400> SEQUENCE: 90
ccaggttacc agcaacagat ctc                                               23

<210> SEQ ID NO 91
<211> LENGTH: 20
<212> TYPE: DNA
<213> ORGANISM: Artificial Sequence
<220> FEATURE:
<223> OTHER INFORMATION: synthetic construct

<400> SEQUENCE: 91
gggctggcta ctggcCttat                                                   20

<210> SEQ ID NO 92
<211> LENGTH: 20
<212> TYPE: DNA
<213> ORGANISM: Artificial Sequence
<220> FEATURE:
<223> OTHER INFORMATION: synthetic construct

<400> SEQUENCE: 92
atggcatctt ccagggggtcc                                                  20

<210> SEQ ID NO 93
<211> LENGTH: 20
<212> TYPE: DNA
<213> ORGANISM: Artificial Sequence
<220> FEATURE:
<223> OTHER INFORMATION: synthetic construct

<400> SEQUENCE: 93
agctccgcct gggtcttcat                                                   20
```

<210> SEQ ID NO 94
<211> LENGTH: 20
<212> TYPE: DNA
<213> ORGANISM: Artificial Sequence
<220> FEATURE:
<223> OTHER INFORMATION: synthetic construct

<400> SEQUENCE: 94
gcggagacgt tcatgactgg                                          20

<210> SEQ ID NO 95
<211> LENGTH: 55
<212> TYPE: DNA
<213> ORGANISM: Artificial Sequence
<220> FEATURE:
<223> OTHER INFORMATION: synthetic construct

<400> SEQUENCE: 95
tcgtcggcag cgtcagatgt gtataagaga cagtccctca ctcctgctcg gtgaa   55

<210> SEQ ID NO 96
<211> LENGTH: 56
<212> TYPE: DNA
<213> ORGANISM: Artificial Sequence
<220> FEATURE:
<223> OTHER INFORMATION: synthetic construct

<400> SEQUENCE: 96
gtctcgtggg ctcggagatg tgtataagag acagaagtca ctctggggaa cacgcc  56

<210> SEQ ID NO 97
<211> LENGTH: 55
<212> TYPE: DNA
<213> ORGANISM: Artificial Sequence
<220> FEATURE:
<223> OTHER INFORMATION: synthetic construct

<400> SEQUENCE: 97
tcgtcggcag cgtcagatgt gtataagaga cagacctttt gggcgtggag aaggg   55

<210> SEQ ID NO 98
<211> LENGTH: 56
<212> TYPE: DNA
<213> ORGANISM: Artificial Sequence
<220> FEATURE:
<223> OTHER INFORMATION: synthetic construct

<400> SEQUENCE: 98
gtctcgtggg ctcggagatg tgtataagag acaggggagg gggtcagcat gaaagg  56

<210> SEQ ID NO 99
<211> LENGTH: 55
<212> TYPE: DNA
<213> ORGANISM: Artificial Sequence
<220> FEATURE:
<223> OTHER INFORMATION: synthetic construct

<400> SEQUENCE: 99
tcgtcggcag cgtcagatgt gtataagaga cagctccccc accccctagg aaagt   55

<210> SEQ ID NO 100
<211> LENGTH: 56
<212> TYPE: DNA
<213> ORGANISM: Artificial Sequence
<220> FEATURE:

<223> OTHER INFORMATION: synthetic construct

<400> SEQUENCE: 100
gtctcgtggg ctcggagatg tgtataagag acagcccttt ctggtggagt gtcccc      56

<210> SEQ ID NO 101
<211> LENGTH: 59
<212> TYPE: DNA
<213> ORGANISM: Artificial Sequence
<220> FEATURE:
<223> OTHER INFORMATION: synthetic construct

<400> SEQUENCE: 101
tcgtcggcag cgtcagatgt gtataagaga cagtgaaggt ataggagagg ttttgggct    59

<210> SEQ ID NO 102
<211> LENGTH: 60
<212> TYPE: DNA
<213> ORGANISM: Artificial Sequence
<220> FEATURE:
<223> OTHER INFORMATION: synthetic construct

<400> SEQUENCE: 102
gtctcgtggg ctcggagatg tgtataagag acagagacga ccttagatgg agtgttgtgt   60

<210> SEQ ID NO 103
<211> LENGTH: 55
<212> TYPE: DNA
<213> ORGANISM: Artificial Sequence
<220> FEATURE:
<223> OTHER INFORMATION: synthetic construct

<400> SEQUENCE: 103
tcgtcggcag cgtcagatgt gtataagaga cagtgccagt ggaaggaggg agtgt         55

<210> SEQ ID NO 104
<211> LENGTH: 56
<212> TYPE: DNA
<213> ORGANISM: Artificial Sequence
<220> FEATURE:
<223> OTHER INFORMATION: synthetic construct

<400> SEQUENCE: 104
gtctcgtggg ctcggagatg tgtataagag acagtgccca ggaagttgct tctccc       56

<210> SEQ ID NO 105
<211> LENGTH: 245
<212> TYPE: DNA
<213> ORGANISM: Artificial Sequence
<220> FEATURE:
<223> OTHER INFORMATION: synthetic construct

<400> SEQUENCE: 105
aagtcactct ggggaacacg cccggtgtca cgccacttga caggcgagta acagacatgg   60
accatcagga aacattaacg tactgatgtt aacagctgac ccaataagtg gcagagtgct  120
aagggaacgt tcacggagac tgaacactcc tcaaacggtc cccagagggt tctagaccca  180
gaggctcaag tgagcagctg aggcaggtgc ctgctgagcc aaattcaccg agcaggagtg  240
aggga                                                              245

<210> SEQ ID NO 106
<211> LENGTH: 243
<212> TYPE: DNA
<213> ORGANISM: Homo sapiens

```
<400> SEQUENCE: 106 gggaggggt   cagcatgaaa  ggagcagtgt  gaaatggaca  attcacacac  cttccatgtt      60
tctcaacaat  gtcagtccct  gctgttgcca  cggccgctat  ggtcttctca  caacaagaag     120
agtattagac  atggaccagc  aggaaagcac  acgttcacag  gcacgtgccc  atgctcacaa     180
acacacacat  gtgtgcatgc  acacatgcac  actccctaca  ccccttctcc  acgcccaaaa     240
ggt                                                                        243

<210> SEQ ID NO 107
<211> LENGTH: 230
<212> TYPE: DNA
<213> ORGANISM: Homo sapiens

<400> SEQUENCE: 107
ctcccccacc  ccctaggaaa  gtcaggtgat  ggttcagcaa  gtatcacatc  gcctctgtaa      60
aggtgataaa  ctggctgcca  gggccaggga  gaggccattt  tctgatggtc  catacctgtt     120
acactaaagt  gttaattgaa  tgcagatgcc  agggaggagc  aacttccagg  gcatgtgcat     180
caagagacaa  aacagtggaa  tatgtcctgg  ggacactcca  ccagaaaggg                  230

<210> SEQ ID NO 108
<211> LENGTH: 226
<212> TYPE: DNA
<213> ORGANISM: Homo sapiens

<400> SEQUENCE: 108
agacgacctt  agatggagtg  ttgtgtattt  caaacagagt  taccattgtg  ctttatcgtg      60
atcagtcccc  ttcttgacac  gtgagagtta  cagacatgta  caataagaaa  attaggaaaa     120
tttcggacaa  aaacatctga  atatataaga  atttgaattg  aatttcctat  ctctcttatt     180
aaaaacaaac  ataaaccttta agcccaaaac  ctctcctata  ccttca                     226

<210> SEQ ID NO 109
<211> LENGTH: 236
<212> TYPE: DNA
<213> ORGANISM: Homo sapiens

<400> SEQUENCE: 109
tgccagtgga  aggagggagt  gttacaggta  gttaagcagg  catgagctgg  gctggagagg      60
gctgtcctcc  acccactagg  aatgtcaggt  gatggctcag  caattatcac  attgactctc     120
taaaagtgac  aaattggcag  ccagtgccag  ggagaagcca  tttcctgatg  gtccacacct     180
gttacactaa  agggttaatt  gaatgcagat  gccagggaga  agcaacttcc  tgggca         236
```